United States Patent
Lee et al.

(10) Patent No.: US 12,304,905 B2
(45) Date of Patent: May 20, 2025

(54) PHARMACEUTICAL SALTS OF BENZOTHIAZOL COMPOUNDS, POLYMORPHS AND METHODS FOR PREPARATION THEREOF

(71) Applicant: 1ST Biotherapeutics, Inc., Gyeonggi-do (KR)

(72) Inventors: Jinhwa Lee, Gyeonggi-do (KR); Suyeon Jo, Gyeonggi-do (KR)

(73) Assignee: 1ST Biotherapeutics, Inc., Gyeonggi-do (KR)

( * ) Notice: Subject to any disclaimer, the term of this patent is extended or adjusted under 35 U.S.C. 154(b) by 868 days.

(21) Appl. No.: 17/442,754

(22) PCT Filed: Mar. 27, 2020

(86) PCT No.: PCT/IB2020/052931
§ 371 (c)(1),
(2) Date: Sep. 24, 2021

(87) PCT Pub. No.: WO2020/194260
PCT Pub. Date: Oct. 1, 2020

(65) Prior Publication Data
US 2022/0177463 A1    Jun. 9, 2022

Related U.S. Application Data

(60) Provisional application No. 62/825,102, filed on Mar. 28, 2019.

(51) Int. Cl.
*C07D 417/04* (2006.01)

(52) U.S. Cl.
CPC ........ *C07D 417/04* (2013.01); *C07B 2200/13* (2013.01)

(58) Field of Classification Search
CPC .................. C07D 417/04; C07B 2200/13
See application file for complete search history.

(56) References Cited

U.S. PATENT DOCUMENTS

| 9,505,784 | B2 | 11/2016 | Choi et al. |
| 10,385,046 | B1 | 8/2019 | Lee et al. |
| 2019/0100500 | A1* | 4/2019 | Lee ..................... A61K 31/437 |

FOREIGN PATENT DOCUMENTS

| JP | 2004-525970 A | 8/2004 |
| JP | 2012-512881 A | 6/2012 |
| JP | 2012-512885 A | 6/2012 |
| JP | 2018-108981 A | 7/2018 |
| WO | WO-2007/095588 A1 | 8/2007 |
| WO | WO-2009/133127 A1 | 11/2009 |
| WO | WO-2010/008847 A2 | 1/2010 |
| WO | WO-2010/100144 A1 | 9/2010 |

OTHER PUBLICATIONS

Office Action from corresponding Japanese Patent Application No. 2021-557547, dated Apr. 9, 2024.
International Search Report from corresponding PCT Application No. PCT/IB2020/052931, dated Jun. 24, 2020.

* cited by examiner

*Primary Examiner* — Rayna Rodriguez
*Assistant Examiner* — Christopher L Johnson
(74) *Attorney, Agent, or Firm* — Harness, Dickey & Pierce, P.L.C.

(57) ABSTRACT

The present disclosure provides polymorphic forms and salts of (1S,2S)-2-fluoro-N-(6-(4-methylpyridin-3-yl)benzo[d]thiazol-2-yl)cyclopropane-1-carboxamide, pharmaceutical compositions comprising the compounds, processes for preparation of the compounds, and methods for treating neurodegenerative disorders.

10 Claims, 41 Drawing Sheets

PHARMACEUTICAL SALTS OF BENZOTHIAZOL COMPOUNDS, POLYMORPHS AND METHODS FOR PREPARATION THEREOF

CROSS-REFERENCE TO RELATED APPLICATIONS

This application is a National Phase entry of PCT/IB2020/052931, filed on 27 Mar. 2020, which claims the benefits of, and priority to, U.S. provisional application Ser. No. 62/825,102 filed on 28 Mar. 2019. The entire disclosures of the applications identified in this paragraph are incorporated herein by references.

FIELD

The present disclosure generally relates to salts and polymorphs of a compound having enzyme inhibitory activity, methods for preparing the compounds, and methods of using the compounds for treating disorders.

BACKGROUND

α-Synuclein is part of a large family of proteins including β- and γ-synuclein and synoretin. α-Synuclein is expressed in the normal state associated with synapses and is believed to play a role in neural plasticity, learning and memory. Several studies have implicated α-synuclein with a central role in Parkinson disease pathogenesis. Molecular changes in the α-synuclein protein that increase protein misfolding and aggregation have a direct role in disease pathogenesis. Aggregation of α-synuclein contributes to the formation of Lewy bodies and neutrites, the pathologic hallmarks of Parkinson disease and α-synucleinopathies. Activation of tyrosine kinase c-abl contributes to α-synuclein-induced neurodegeneration.

The tyrosine kinase c-abl is tightly regulated non-receptor protein tyrosine kinase involved in a wide range of cellular processes, including growth, survival and stress response (*Nat Rev Mol Cell Biol*, 2004, 5:33-44) and c-abl involved in regulation several cellular processes and has implicated in the development of the central nervous system by controlling neurogenesis. More recently, increasing evidence from various experimental model systems has also revealed that c-abl is activated in neurodegenerative disease such as Alzheimer's disease, Parkinson's disease, Niemann-Pick type C diseases and tauopathies. (*Human Molecular Genetics*, 2014, Vol. 23, No. 11)

The stress-signaling non-receptor tyrosine kinase c-abl links parkin to sporadic forms of Parkinson's disease via tyrosine phosphorylation. Tyrosine phosphorylation of parkin by c-abl is a major post-translational modification that leads to loss of parkin function and disease progression in sporadic Parkinson disease. Inhibition of c-abl offers new therapeutic opportunities for blocking Parkinson disease progression. (*The Journal of Neuroscience*, 2011, 31(1):157-163) Amyotrophic lateral sclerosis (ALS) is a fatal neurodegenerative disease characterized by progressive death of motor neurons. Knockdown of c-abl with small interfering RNAs (siRNAs) also rescued ALS motor neuron degeneration. (Imamura et al., *Sci. Transl. Med.* 9, 2017) Multiple System Atrophy (MSA) is a rare, rapidly progressive neurodegenerative disease without any current treatment. In MSA there is accumulation of α-synuclein in the neurons and oligodendrocytes of the substantia nigra, striatum, olivopontocerebellar structures and spinal cord. (*J Neural Transm Vienna Austria* 1996. 2016; 123(6))

Administration of the tyrosine kinase inhibitor nilotinib decreases c-abl activity and ameliorates autophagic clearance of α-synuclein in transgenic and lentiviral gene transfer models. Activation of c-abl in the mouse forebrain induces neurodegeneration in the hippocampus and striatum. Therefore, an increase in c-abl activity via phosphorylation may be associated with the α-synuclein pathology detected in Parkinson disease and other neurodegenerative disease. (*Hum Mol Genet.* 2013 Aug. 15).

U.S. Ser. No. 16/148,265 describes benzothiazole compounds as a c-abl inhibitor that is useful for the treatment of a disease or disorders such as α-synucleinopathy, Parkinson disease, Alzheimer disease, ALS, Dementia with Lewy body and MSA. The present disclosure describes novel salt and polymorph of benzothiazole compound which may improve the physicochemical properties and solubility of the compound.

SUMMARY

The present disclosure provides crystalline forms of a compound of Formula (I) and salts thereof:

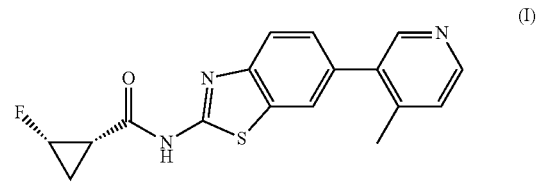 [SMILES: Cc1ccncc1-c1ccc2nc(NC(=O)[C@@H]3C[C@@H]3F)sc2c1]

and preparation processes for the compounds. The compounds are suitable for pharmaceutical development and industrial process.

In one embodiment, the present disclosure provides the hydrochloride, sulfate, L-aspartate, maleate, phosphate, L-(+)-tartrate, fumarate, citrate, L-malate and methane sulfate salts of the compound of Formula (I) and crystalline forms thereof.

In another embodiment, the present disclosure provides a method of preparing a variety of crystalline salts of the compound of Formula (I) comprising the step of: reacting (1S,2S)-2-fluoro-N-(6-(4-methylpyridin-3-yl)benzo[d]thiazol-2-yl)cyclopropane-1-carboxamide free base with an acid in a solvent.

The crystalline forms can be characterized by the inter-lattice plane intervals determined by an X-ray powder diffraction pattern (XRPD). The diffractogram of XRPD is typically represented by a diagram plotting the intensity of the peaks versus the location of the peaks, i.e., diffraction angle 2θ (two-theta) in degrees. The intensities are often given in parenthesis with the following abbreviations: very strong=vst; strong=st; medium=m; weak=w; and very weak=vw. The characteristic peaks of a given XRPD can be selected according to the peak locations and their relative intensity to conveniently distinguish this crystalline structure from others.

DETAILED DESCRIPTION

Figure 1:
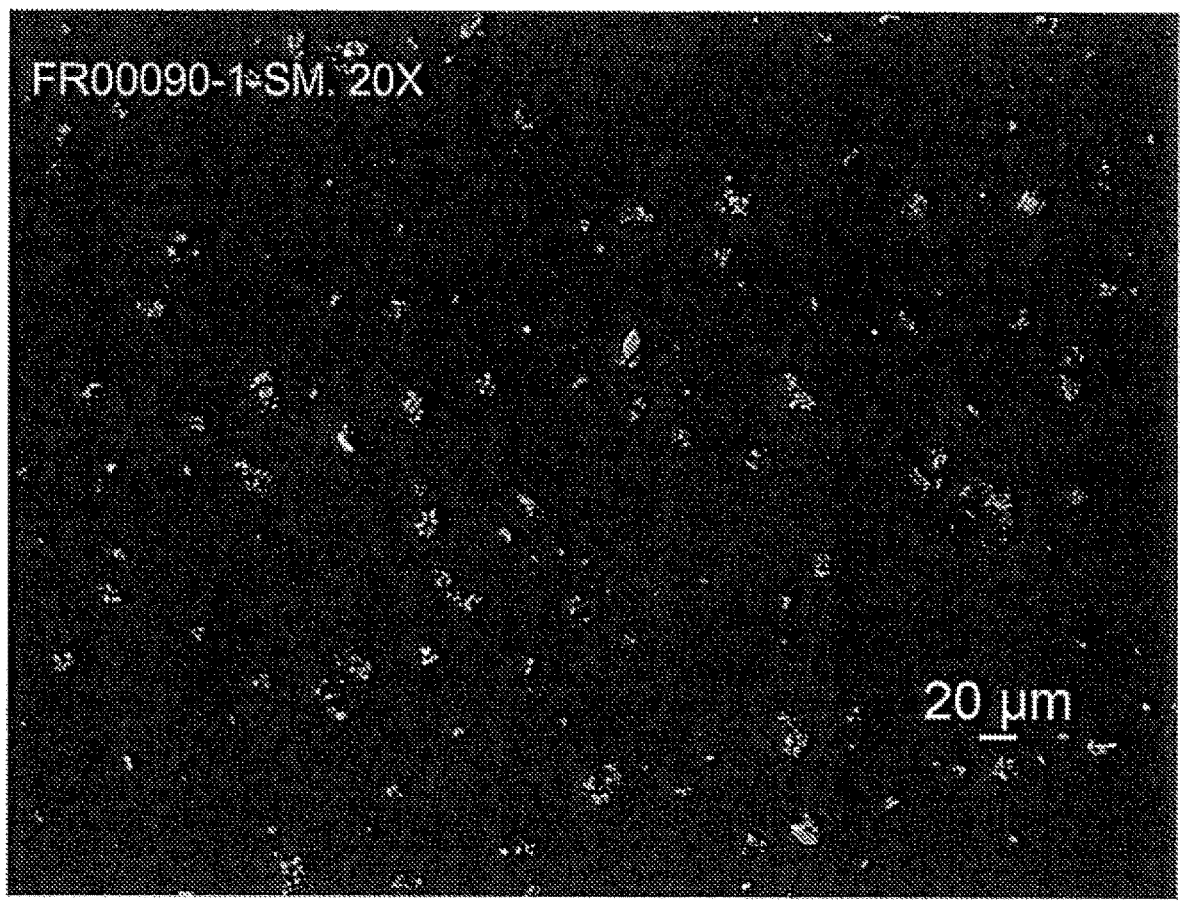
FIG. 1 shows the optical micrograph of crystalline Form of Formula (I).

The following description is merely exemplary in nature and is not intended to limit the present disclosure, application, or uses.

Definitions

As used herein, the term "pharmaceutically acceptable carrier" refers to a diluent, adjuvant, excipient, or carrier, or other ingredient which is pharmaceutically-acceptable and with which a compound of the invention is administered.

As used herein, the term "pharmaceutically acceptable salt" refers to a salt which may enhance desired pharmacological activity. Examples of pharmaceutically-acceptable salts include acid addition salts formed with inorganic or organic acids, metal salts and amine salts. Examples of acid addition salts formed with inorganic acids include salts with hydrochloric acid, hydrobromic acid, sulfuric acid, nitric acid and phosphoric acid. Examples of acid addition salts formed with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxy-benzoyl)-benzoic acid, cinnamic acid, mandelic acid, methanesulfonic acid, ethanesulfonic acid, 1,2-ethanedisulfonic acid, 2-hydroxyethane-sulfonic acid, benzenesulfonic acid, p-chlorobenzenesulfonic acid, 2-naphthalenesulfonic acid, p-toluenesulfonic acid, camphorsulfonic acid, 4-methyl-bicyclo

[2.2.2]oct-2-ene1-carboxylic acid, gluco-heptonic acid, 4,4'-methylenebis(3-hydroxy-2-naphthoic) acid, 3-phenylpropionic acid, trimethyl-acetic acid, tertiary butylacetic acid, lauryl sulfuric acid, gluconic acid, glutamic acid, hydroxy-naphthoic acids, salicylic acid, stearic acid and muconic acid. Examples of metal salts include salts with sodium, potassium, calcium, magnesium, aluminum, iron, and zinc ions. Examples of amine salts include salts with ammonia and organic nitrogenous bases strong enough to form salts with carboxylic acids.

As used herein, the term "therapeutically effective amount" means when applied to a compound of the invention is intended to denote an amount of the compound that is sufficient to ameliorate, palliate, stabilize, reverse, slow or delay the progression of a disorder or disease state, or of a symptom of the disorder or disease. In an embodiment, the method of the present invention provides for administration of combinations of compounds. In such instances, the "therapeutically effective amount" is the amount of a compound of the present invention in the combination sufficient to cause the intended biological effect.

As used herein, the term "treatment" or "treating" as used herein means ameliorating or reversing the progress or severity of a disease or disorder, or ameliorating or reversing one or more symptoms or side effects of such disease or disorder. "Treatment" or "treating", as used herein, also means to inhibit or block, as in retard, arrest, restrain, impede or obstruct, the progress of a system, condition or state of a disease or disorder. For purposes of this invention, "treatment" or "treating" further means an approach for obtaining beneficial or desired clinical results, where "beneficial or desired clinical results" include, without limitation, alleviation of a symptom, diminishment of the extent of a disorder or disease, stabilized (i.e., not worsening) disease or disorder state, delay or slowing of a disease or disorder state, amelioration or palliation of a disease or disorder state, and remission of a disease or disorder, whether partial or total.

In another embodiment, the compounds of Formula (I) are used for modulating the activity of a protein kinase c-abl.

As used herein, the term "modulating", or "modulation" refers to the alteration of the catalytic activity of a protein kinase. In particular, modulating refers to the activation or inhibition of the catalytic activity of a protein kinase, depending on the concentration of the compound or salt to which the protein kinase is exposed or, more preferably, the inhibition of the catalytic activity of a protein kinase. The term "catalytic activity" as used herein refers to the rate of phosphorylation of tyrosine, serine or threonine under the influence, direct or indirect, of a protein kinase.

As used herein, the phrase "compound(s) of this/the disclosure" includes any compound(s) of Formula (I), as well as clathrates, hydrates, solvates, or polymorphs thereof. And, even if the term "compound(s) of the disclosure" does not mention its pharmaceutically acceptable sat, the term includes salts thereof. In one embodiment, the compounds of this disclosure include stereochemically pure compounds, e.g., those substantially free (e.g., greater than 85% ee, greater than 90% ee, greater than 95% ee, greater than 97% ee, or greater than 99% ee) of other stereoisomers. That is, if the compounds of Formula (I) according to the present disclosure or salts thereof are tautomeric isomers and/or stereoisomers (e.g., geometrical isomers and conformational isomers), such isolated isomers and their mixtures also are included in the scope of this disclosure. If the compounds of the present disclosure or salts thereof have an asymmetric carbon in their structures, their active optical isomers and their racemic mixtures also are included in the scope of this disclosure.

As used herein, the term "polymorph" refers to solid crystalline forms of a compound of this disclosure or complex thereof. Different polymorphs of the same compound can exhibit different physical, chemical and/or spectroscopic properties. Different physical properties include, but are not limited to stability (e.g., to heat or light), compressibility and density (important in formulation and product manufacturing), and dissolution rates (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to, for example, the shape or size distribution of particles of it.

As used herein, the term "X-ray powder diffraction pattern" or "XRPD pattern" refers to the experimentally observed diffractogram or parameters derived therefrom. X-ray powder diffraction patterns are typically characterized by peak position (abscissa) and peak intensities (ordinate). The term "peak intensities" refers to relative signal intensities within a given X-ray diffraction pattern. Factors which can affect the relative peak intensities are sample thickness and preferred orientation (i.e., the crystalline particles are not distributed randomly).

As used herein, the term "peak positions" as used herein refers to X-ray reflection positions as measured and observed in X-ray powder diffraction experiments. Peak positions are directly related to the dimensions of the unit cell. The peaks, identified by their respective peak positions, have been extracted from the diffraction patterns for the various polymorphic forms of salts of Formula (I).

As used herein, the term "2 theta value" refers to the peak position in degrees based on the experimental setup of the X-ray diffraction experiment and is a common abscissa unit in diffraction patterns. In general, the experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific polymorphic form is intended to mean the 2θ values (in degrees) as measured using the X-ray diffraction experimental conditions as described herein.

As used herein, the term "amorphous" refers to any solid substance which (i) lacks order in three dimensions, or (ii) exhibits order in less than three dimensions, order only over short distances (e.g., less than 10 Å), or both. Thus, amorphous substances include partially crystalline materials and crystalline mesophases with, e.g. one- or two-dimensional translational order (liquid crystals), orientational disorder (orientationally disordered crystals), or conformational disorder (conformationally disordered crystals). Amorphous solids may be characterized by known techniques, including X-ray powder diffraction (XRPD) crystallography, solid state nuclear magnet resonance (ssNMR) spectroscopy, differential scanning calorimetry (DSC), or some combination of these techniques. Amorphous solids give diffuse XRPD patterns, typically comprised of one or two broad peaks (i.e., peaks having base widths of about 5° 2θ or greater).

As used herein, the term "crystalline" refers to any solid substance exhibiting three-dimensional order, which in contrast to an amorphous solid substance, gives a distinctive XRPD pattern with sharply defined peaks.

As used herein, the term "crystalline purity" refer to percentage of a crystalline compound in a sample which may contain an amorphous form of the same compound, at least one other crystalline form of the compound or a mixture thereof.

As used herein, the term "substantial crystalline purity" refer to crystalline purity at least about 95% crystalline purity, preferably about 97% crystalline purity, more preferably about 99% crystalline purity, and most preferably about 100% crystalline purity As used herein, the term "detectable amount" refers to an amount or amount per unit volume that can be detected using conventional techniques, such as X-ray powder diffraction, differential scanning calorimetry, HPLC, Fourier Transform Infrared Spectroscopy (FT-IR), Raman spectroscopy, and the like.

As used herein, the term "sample" includes any compound(s), as well as clathrates, hydrates, solvates, polymorphs or intermediate compounds thereof.

As used herein, the term "solvent" refer to a substance, preferably a liquid or a miscible, partially miscible or immiscible mixture of two or more liquids, which is capable of completely dissolving, partially dissolving, dispersing or partially dispersing another substance, preferably a solid or a mixture of solids. It is meant to be understood that, because many solvents and anti-solvents contain impurities, the level of impurities in solvents and anti-solvents for the practice of this invention, if present, are at a low enough concentration that they do not interfere with the intended use of the solvent in which they are present.

As used herein, the term "solvate" means a compound or its salt according to this disclosure that further includes a stoichiometric or non-stoichiometric amount of a solvent bound by non-covalent intermolecular forces. Preferred solvents are volatile, non-toxic, and/or acceptable for administration to humans in trace amounts.

As used herein, the term "hydrate" means a compound or its salt according to this disclosure that further includes a stoichiometric or non-stoichiometric amount of water bound by non-covalent intermolecular forces.

As used herein, the term "relative humidity" refers to the ratio of the amount of water vapor in air at a given temperature to the maximum amount of water vapor that can be held at that temperature and pressure, expressed as a percentage.

As used herein, the term "slurry" refers to a solid substance suspended in a liquid medium, typically water or an organic solvent.

As used herein, the term "under vacuum" refers to typical pressures obtainable by a laboratory oil or oil-free diaphragm vacuum pump.

As used herein, the term "clathrate" means a compound or its salt in the form of a crystal lattice that contains spaces (e.g., channels) that have a guest molecule (e.g., a solvent or water) trapped within.

Compounds of the Present Disclosure

In an embodiment, the present disclosure provides a salt of the compound of Formula (I):

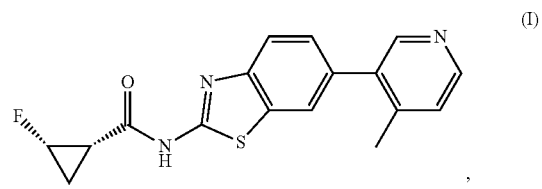 [SMILES: Cc1ccncc1-c1ccc2nc(NC(=O)[C@@H]3C[C@@H]3F)sc2c1]

wherein the salt is an acid addition salt and the acid is selected from the group consisting of hydrochloride, sulfate, L-aspartate, maleate, phosphate, L-(+)-tartrate, fumarate, citrate, L-malate and methane sulfate.

In a particular embodiment, the salt is a mono-hydrochloride salt that possesses desirable properties such as high crystallinity and favorable non-hygroscopicity, while maintaining good solubility.

In some other embodiments, the present disclosure provides crystalline forms of the compound and preparation processes therefor, which are suitable for pharmaceutical development and industrial process.

In a particular embodiment, the present disclosure provides a crystalline form of (1S,2S)-2-fluoro-N-(6-(4-methylpyridin-3-yl)benzo[d]thiazol-2-yl)cyclopropane-1-carboxamide free base, named crystalline "Pattern A." Pattern A has been characterized by XRPD, DSC, TGA and solubility test as described herein. The crystalline Pattern A, which is characterized by a XRPD, has peaks at diffraction angle (2θ) of 9.8±0.2, 11.6±0.2, 13.2±0.2, 14.0±0.2, 16.7±0.2, 17.6±0.2, 20.6±0.2, 22.9±0.2, 26.2±0.2, 29.3±0.2, 30.7±0.2, 31.6±0.2 and by DSC an onset melting point of about 267° C. with a peak temperature of about 268° C.

In another embodiment, the present disclosure provides a hydrochloride salt of Formula (I) characterized by a XRPD having peaks at diffraction angle (2θ) of 6.0±0.2, 15.9±0.2, 18.1±0.2, 19.7±0.2, 24.6±0.2, 25.4±0.2, 26.7±0.2 and by DSC a melting point of 240° C.

In some embodiment, the present disclosure provides a method of preparing a variety of crystalline salts of the compound of Formula (I) comprising the step of: reacting (1S,2S)-2-fluoro-N-(6-(4-methylpyridin-3-yl)benzo[d]thiazol-2-yl)cyclopropane-1-carboxamide free base with an acid in a solvent.

New XRPD patterns was found in salt formation experiments with five different counter-ions, including hydrochloric acid (Pattern I), sulfuric acid (Pattern II), maleic acid (Pattern III), fumaric acid (Pattern IV) and methane sulfonic acid (Pattern V). Meanwhile, amorphous solids can be obtained after salt formation with phosphoric acid, which also indicates the formation of potential salt.

Those skilled in the art recognize that the measurements of the XRPD peak locations and/or intensity for a given crystalline form of the same compound will vary within a margin of error. The values of degree 2θ allow appropriate error margins. Typically, the error margins are represented by "±". For example, the degree 2θ of about "8.7±0.3" denotes a range from about 8.7+0.3, i.e., about 9.0, to about 8.7±0.3, i.e., about 8.4. Depending on the sample preparation techniques, the calibration techniques applied to the instruments, human operational variation, etc., those skilled in the art recognize that the appropriate error of margins for a XRPD can be ±0.5; ±0.4; ±0.3; ±0.2; ±0.1; ±0.05; or less. In certain embodiments of the invention, the XRPD margin of error is ±0.2. Additional details of the methods and equipment used for the XRPD analysis are described in the Examples section.

All these potential salts can be further characterized by characterized by DSC and TGA, especially, organic salts can also be characterized by 1H-NMR to confirm the formation of the salts and the stoichiometry of acid/base ratios.

To investigate the influence of ratio of hydrochloric acid on the salt formation process, salt formation experiments with different acid ratio (1.1 e.q. and 2.2 e.q.) can be carried out.

For (1S,2S)-2-fluoro-N-(6-(4-methylpyridin-3-yl)benzo[d]thiazol-2-yl)cyclopropane-1-carboxamide mono-hydrochloride with Pattern I, a polymorph screening study can be performed by slurry method, heating-cooling method, slow evaporation method and anti-solvent method.

Dry grinding and wet milling can also be carried out to test physical stability of mono-hydrochloride in the milling process. XRPD results showed the crystallinity of residual solids were decreased after dry grinding, while the crystalline form was not changed after dry grinding or wet granulation process.

In yet another embodiment, there is provided a pharmaceutical composition comprising a therapeutically effective amount of a compound of Formula (I), a pharmaceutically acceptable salt thereof, or a crystalline form thereof, and at least one pharmaceutically acceptable carrier.

In another embodiment, there is provided a method for treating a neurodegenerative disease or disorder comprising administering to a subject in need thereof a therapeutically effective amount of a compound of Formula (I), a pharmaceutically acceptable salt thereof, or a crystalline form thereof. That is, there is provided a medical use of Formula (I), a pharmaceutically acceptable salt thereof, or a crystalline form thereof, wherein Formula (I), a pharmaceutically acceptable salt thereof, or a crystalline form thereof is used as an active ingredient. In one embodiment, the medical-use is for treatment or prevention of the neurodegenerative disease or disorder such as α-synucleinopathy, Parkinson's disease, dementia with Lewy body, multiple system atrophy (MSA), Alzheimer's disease and/or amyotrophic lateral sclerosis (ALS).

Medical Uses and Methods of Treatment Using the Compounds According to the Present Disclosure The present disclosure further provides methods for treating a neurodegenerative disease or disorder in a subject having or susceptible to having such a disease or disorder, by administering to the subject a therapeutically effective amount of one or more compounds as described above. In one embodiment, the treatment is preventative treatment. In another embodiment, the treatment is palliative treatment. In another embodiment, the treatment is restorative treatment.

1. Diseases or Conditions

The compound of the present disclosure for inhibiting c-abl activity is useful for treatment or prevention of a neurodegenerative disease or disorder. The compound can be used for inhibiting or hindering c-abl kinase activity, and for treating a neurodegenerative disease or disorder, or for preventing aggravation of such disease. Thus, the present disclosure provides a method for inhibiting or hindering c-abl activity in a cell, wherein the cell is contacted with an effective amount of a compound of the present disclosure. In one embodiment, such cell is present in a subject (for example, Alzheimer patients). In another embodiment, there is provided a medical use for treating or preventing a neurodegenerative disease or disorder in a subject, using the compound according to the present disclosure. The method of the present disclosure comprises administering to a subject in need of treatment or prevention a pharmaceutical composition containing a therapeutically or prophylactically effective amount of c-abl inhibitor. The neurodegenerative disease or disorder includes, but is not limited to, α-synucleinopathy, Parkinson's disease, dementia with Lewy body, multiple system atrophy (MSA), Alzheimer's disease or amyotrophic lateral sclerosis (ALS).

2. Subjects

Suitable subjects to be treated according to the present disclosure include mammalian subjects. Mammals according to the present disclosure include, but are not limited to, human, canine, feline, bovine, caprine, equine, ovine, porcine, rodents, lagomorphs, primates, and the like, and encompass mammals in utero. Subjects may be of either gender and at any stage of development. In one embodiment, the suitable subject to be treated according to the present disclosure is human.

3. Administration and Dosing

The compounds of the present disclosure are generally administered in a therapeutically effective amount. The compounds of the present disclosure can be administered by any suitable route in the form of a pharmaceutical composition adapted to such a route, and in a dose effective for the treatment intended. An effective dosage is typically in the range of about 0.001 to about 100 mg per kg body weight per day, preferably about 0.01 to about 50 mg/kg/day, in single or divided doses. Depending on age, species and disease or condition being treated, dosage levels below the lower limit of this range may be suitable. In other cases, still larger doses may be used without harmful side effects. Larger doses may also be divided into several smaller doses, for administration throughout the day. Methods for determining suitable doses are well known in the art to which the present disclosure pertains. For example, Remington: The Science and Practice of Pharmacy, Mack Publishing Co., 20th ed., 2000 can be used.

Pharmaceutical Compositions, Dosage Forms and Administration Routes

For the treatment of the diseases or conditions referred to above, the compounds described herein or pharmaceutically acceptable salts thereof can be administered as follows:

Oral Administration

The compounds of the present disclosure may be administered orally, including by swallowing, so that the compound enters the gastrointestinal tract, or absorbed into the blood stream directly from the mouth (e.g., buccal or sublingual administration).

Suitable compositions for oral administration include solid, liquid, gel or powder formulations, and have a dosage form such as tablet, lozenge, capsule, granule or powder.

Compositions for oral administration may be formulated as immediate or modified release, including delayed or sustained release, optionally with enteric coating.

Liquid formulations can include solutions, syrups and suspensions, which can be used in soft or hard capsules. Such formulations may include a pharmaceutically acceptable carrier, for example, water, ethanol, polyethylene glycol, cellulose, or an oil. The formulation may also include one or more emulsifying agents and/or suspending agents.

In a tablet dosage form the amount of drug present may be from about 0.05% to about 95% by weight, more typically from about 2% to about 50% by weight of the dosage form. In addition, tablets may contain a disintegrant, comprising from about 0.5% to about 35% by weight, more typically from about 2% to about 25% of the dosage form. Examples of disintegrants include, but are not limited to, lactose, starch, sodium starch glycolate, crospovidone, croscarmellose sodium, maltodextrin, or mixtures thereof.

Suitable lubricants, for use in a tablet, may be present in amounts from about 0.1% to about 5% by weight, and include, but are not limited to, talc, silicon dioxide, stearic acid, calcium, zinc or magnesium stearate, sodium stearyl fumarate and the like.

Suitable binders, for use in a tablet, include, but are not limited to, gelatin, polyethylene glycol, sugars, gums, starch, polyvinyl pyrrolidone, hydroxypropyl cellulose, hydroxypropylmethyl cellulose and the like. Suitable diluents, for use in a tablet, include, but are not limited to, mannitol, xylitol, lactose, dextrose, sucrose, sorbitol, microcrystalline cellulose and starch.

Suitable solubilizers, for use in a tablet, may be present in amounts from about 0.1% to about 3% by weight, and include, but are not limited to, polysorbates, sodium lauryl sulfate, sodium dodecyl sulfate, propylene carbonate, diethyleneglycol monoethyl ether, dimethyl isosorbide, polyethylene glycol (natural or hydrogenated) castor oil, HCOR™ (Nikkol), oleyl ester, Gelucire™, caprylic/caprylic acid mono/diglyceride, sorbitan fatty acid esters, and Solutol HS™.

Parenteral Administration

Compounds of the present disclosure may be administered directly into the blood stream, muscle, or internal organs. Suitable means for parenteral administration include intravenous, intra-muscular, subcutaneous intraarterial, intraperitoneal, intrathecal, intracranial, and the like. Suitable devices for parenteral administration include injectors (including needle and needle-free injectors) and infusion methods.

Compositions for parenteral administration may be formulated as immediate or modified release, including delayed or sustained release. Most parenteral formulations are aqueous solutions containing excipients, including salts, buffering agents and isotonic agents. Parenteral formulations may also be prepared in a dehydrated form (e.g., by lyophilization) or as sterile non-aqueous solutions. These formulations can be used with a suitable vehicle, such as sterile water. Solubility-enhancing agents may also be used in preparation of parenteral solutions.

Transdermal Administration

Compounds of the present disclosure may be administered topically to the skin or transdermally. Formulations for this topical administration can include lotions, solutions, creams, gels, hydrogels, ointments, foams, implants, patches and the like. Pharmaceutically acceptable carriers for topical administration formulations can include water, alcohol, mineral oil, glycerin, polyethylene glycol and the like. Topical or transdermal administration can also be performed by electroporation, iontophoresis, phonophoresis and the like.

Compositions for topical administration may be formulated as immediate or modified release, including delayed or sustained release.

Combination Therapy

A pharmaceutical composition according to the present disclosure may contain one or more additional therapeutic agents, for example, to increase the efficacy or decrease the side effects. In some embodiments, accordingly, a pharmaceutical composition further contains one or more additional therapeutic agents selected from active ingredients useful to treat or inhibit diseases mediated directly or indirectly by c-abl kinase. Examples of such active ingredients are, without limitation, agents to treat a neurodegenerative disease or disorder.

References for Preparing Pharmaceutical Compositions

Methods for preparing pharmaceutical compositions for treating or preventing a disease or condition are well known in the art to which the present disclosure pertains. For example, based on *Handbook of Pharmaceutical Excipients* ($7^{th}$ ed.), *Remington: The Science and Practice of Pharmacy* (20th ed.), *Encyclopedia of Pharmaceutical Technology* ($3^{rd}$ ed.), or *Sustained and Controlled Release Drug Delivery Systems* (1978), pharmaceutically acceptable excipients, carriers, additives and so on can be selected and then mixed with the compounds of the present disclosure for making the pharmaceutical compositions.

The present disclosure provides a compound having various pharmacological effects by, for example, inhibiting c-abl activity, a pharmaceutical composition having the compound as an active ingredient, medical use, particularly for treating a neurodegenerative disease or disorder, of the compound, and a method of treatment or prevention comprising administering the compound to a subject in need of such treatment or prevention. The compounds of the present disclosure, pharmaceutically acceptable salts thereof, and/or crystalline forms thereof have good safety and high selectivity for c-abl, and thus exhibit superior property as a pharmaceutical drug.

EXAMPLES

The examples which follow will further illustrate the preparation and characterization of the distinct polymorphic salt forms of Formula (I) but are not intended to limit the scope of the invention as described herein or as claimed herein. Unless otherwise indicated, all temperatures are set forth in degrees Celsius and all parts and percentages are by weight.

It is meant to be understood that peak heights in a powder x-ray diffraction pattern may vary and will be dependent on variables such as the temperature, crystal size, crystal habit, sample preparation or sample height in the analysis well of the Scintagx2 Diffraction Pattern System.

It is also meant to be understood that peak positions may vary when measured with different radiation sources. For example, Cu—Kα1, Mo—Kα, Co—Kα and Fe—Kα radiation, having wavelengths of 1.54060 Å, 0.7107 Å, 1.7902 Å and 1.9373 Å, respectively, may provide peak positions which differ from those measured with Cu—Kα radiation.

While digital outputs from powder x-ray diffractometers may be set to express peak positions to the one-hundredth and one-thousandth of a degree past the decimal, diffractometers are incapable of accurate experimental determination beyond one-tenth of a degree. Accordingly, peak positions reported herein are rounded to one-tenth of a degree past the decimal.

Analytical Instruments and Methods (1) X-ray Powder Diffractometer (XRPD)

Samples were run on XRPD using below method:
Tube: Cu: K-Alpha ($\lambda$=1.54179 Å).
Generator: Voltage: 40 kV; Current: 40 mA.
Scan Scope: 3 to 40 deg;
Sample rotation speed: 15 rpm.

(2) Differential Scanning Calorimetric (DSC)

Details of DSC method used in the tests are mentioned below:
Samples (~1 mg) were tested using a hermetic aluminum pan with pinhole and heated from 25° C. to 300° C. at a rate of 10° C./min.

(3) Thermal Gravimetric Analysis (TGA)
Details of TGA method used in the tests are mentioned below:
  Samples (3-5 mg) were placed in an open platinum pan and heated from 30° C. to 300° C. or weight %<80% at a rate of 10° C./min under 25 mL/min of $N_2$.
(4) Polarized Light Microscope (PLM)
Details of polarized light microscope method used in the tests are mentioned below:
  Nikon LV100POL equipped with 5 megapixel CCD.
  Physical Lens: 10×/20×
(5) Dynamic Vapor Sorption (DVS)
  Samples (~10 mg) were transferred into a DVS instrument and recorded the weight change with respect to the atmospheric humidity at 25° C. using the following parameters:
  Equilibrium: dm/dt: 0.01%/min. (for min: 10 min and max: 180 min).
  Drying: 0% RH for 120 min
  RH (%) measurement step: 10%
  RH (%) measurement step scope: 0-90-0%
(6) Proton Nuclear Magnetic Resonance (1H NMR)
  400 MHz Bruker with DMSO-$d_6$ or MeOH-$d_4$ solvents
  Temperature: 27° C.

Example 1. Physical Properties of Formula (I)

Figure 2:
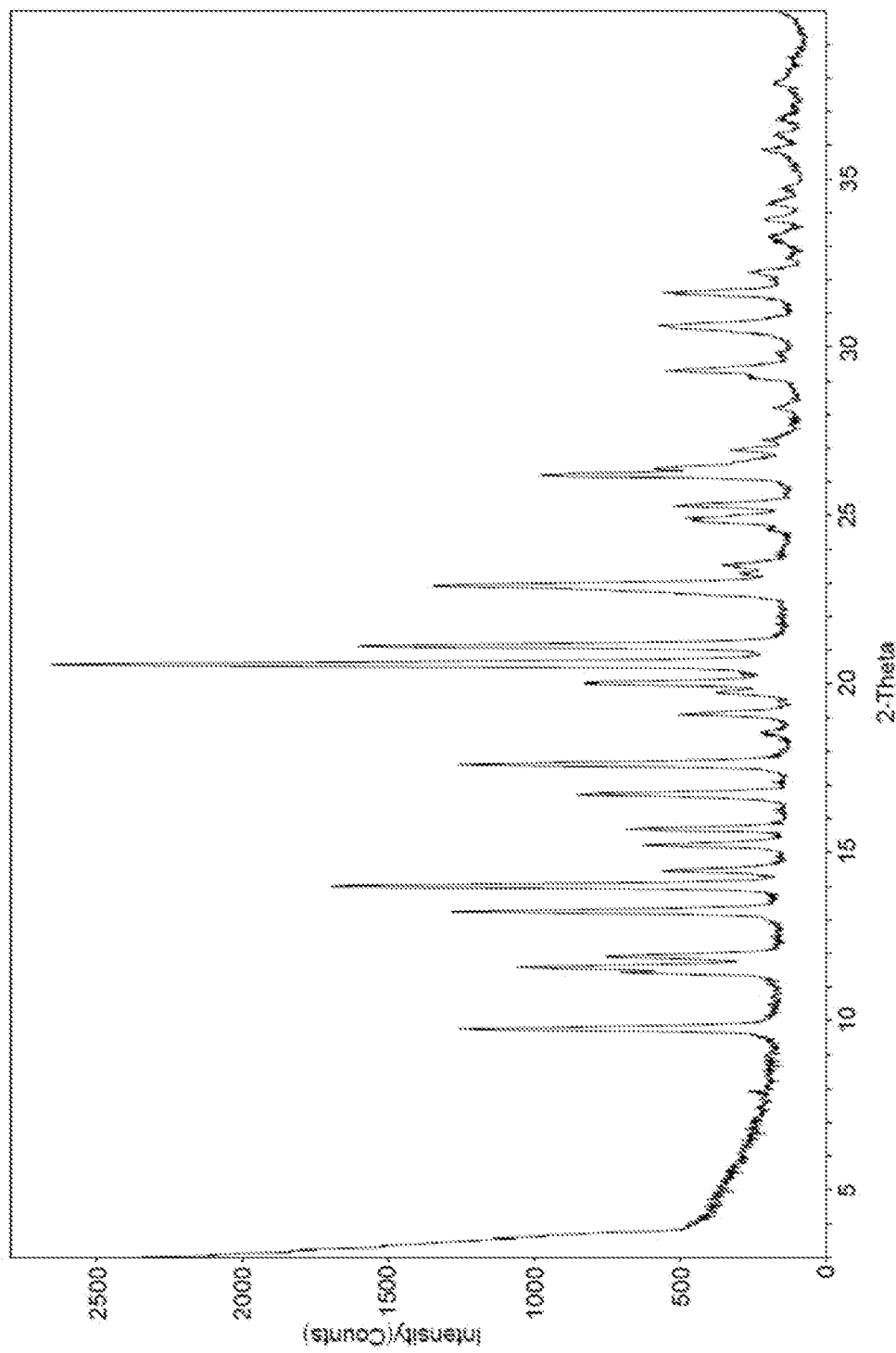
FIG. 2 shows the X-ray powder diffraction (XRPD) pattern of Formula (I).
Figure 3:
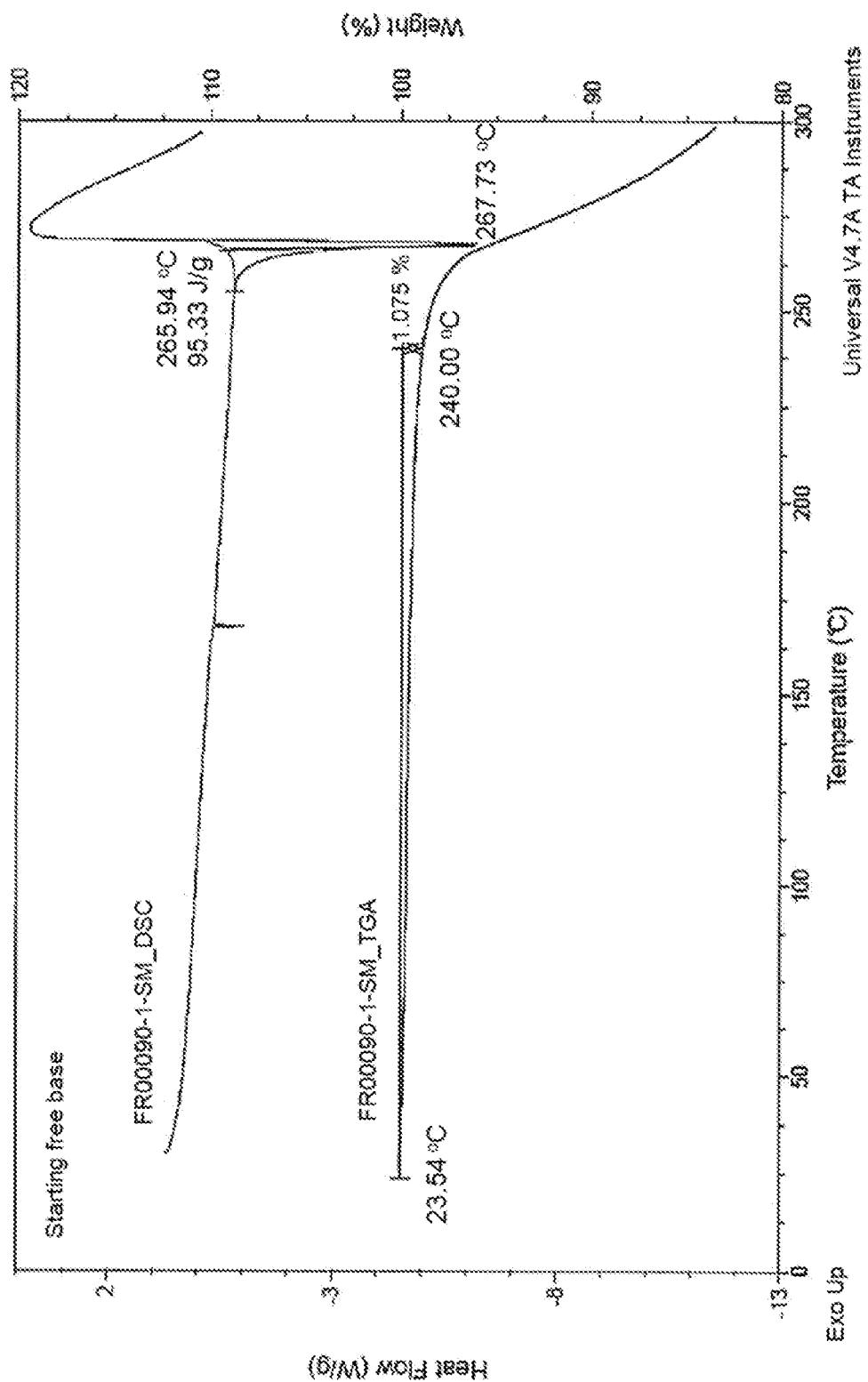
FIG. 3 shows differential scanning calorimeter (DSC) and thermogravimetry (TGA) of Formula (I).
Figure 4:
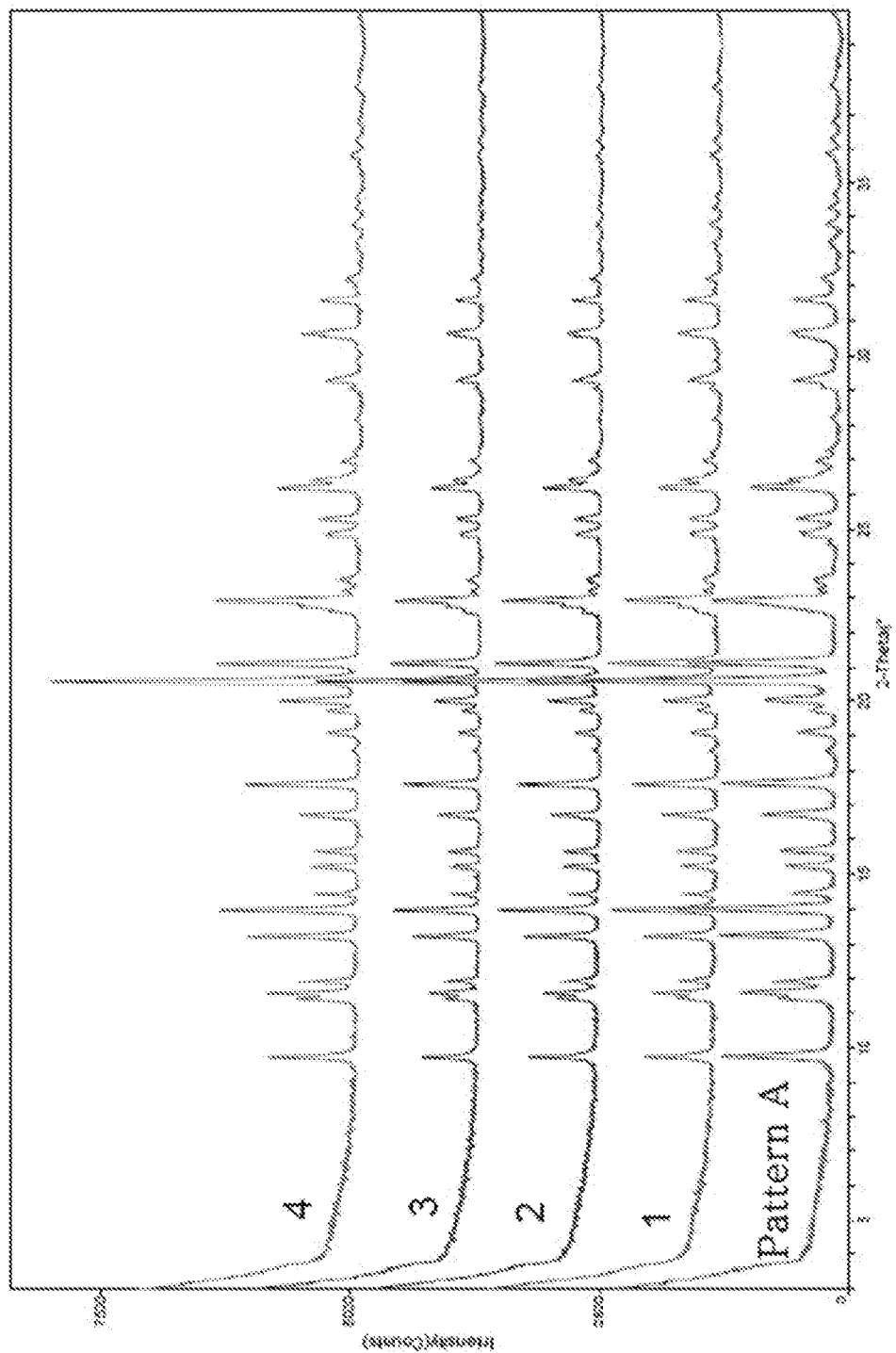
FIG. 4 shows XRPD spectra of Pattern A of Formula (I) in different solvents. 1—from acetone, 2—from ethyl acetate, 3—from acetonitrile, 4—isopropanol/water (95/5, v/v).
Figure 5:
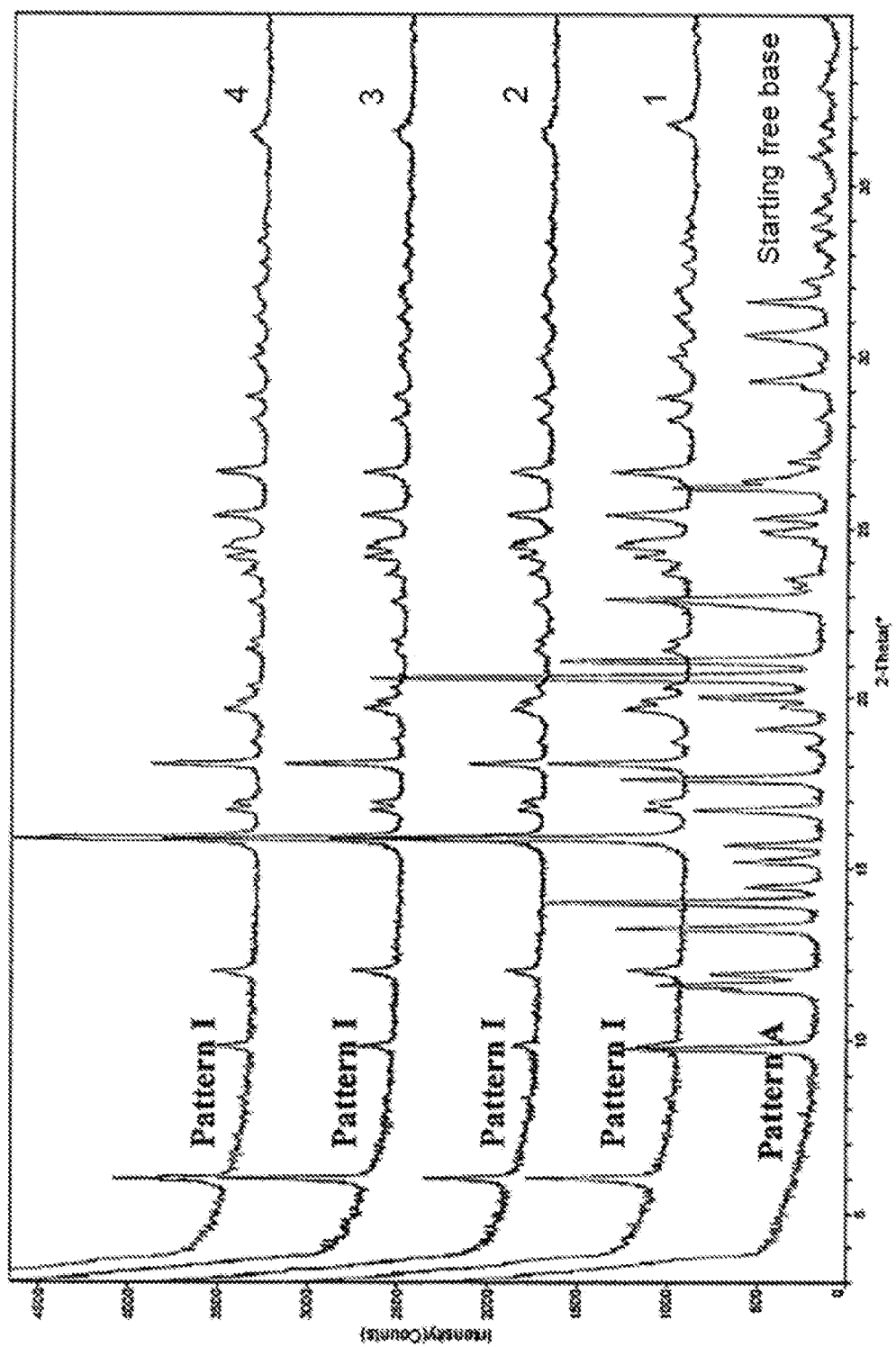
FIG. 5 shows an overlay of XRPD spectra of salt formation of Formula (I) with hydrochloric acid in different solvents. 1—from acetone, 2—from ethyl acetate, 3—from acetonitrile, 4—isopropanol/water (95/5, v/v).
Figure 6:
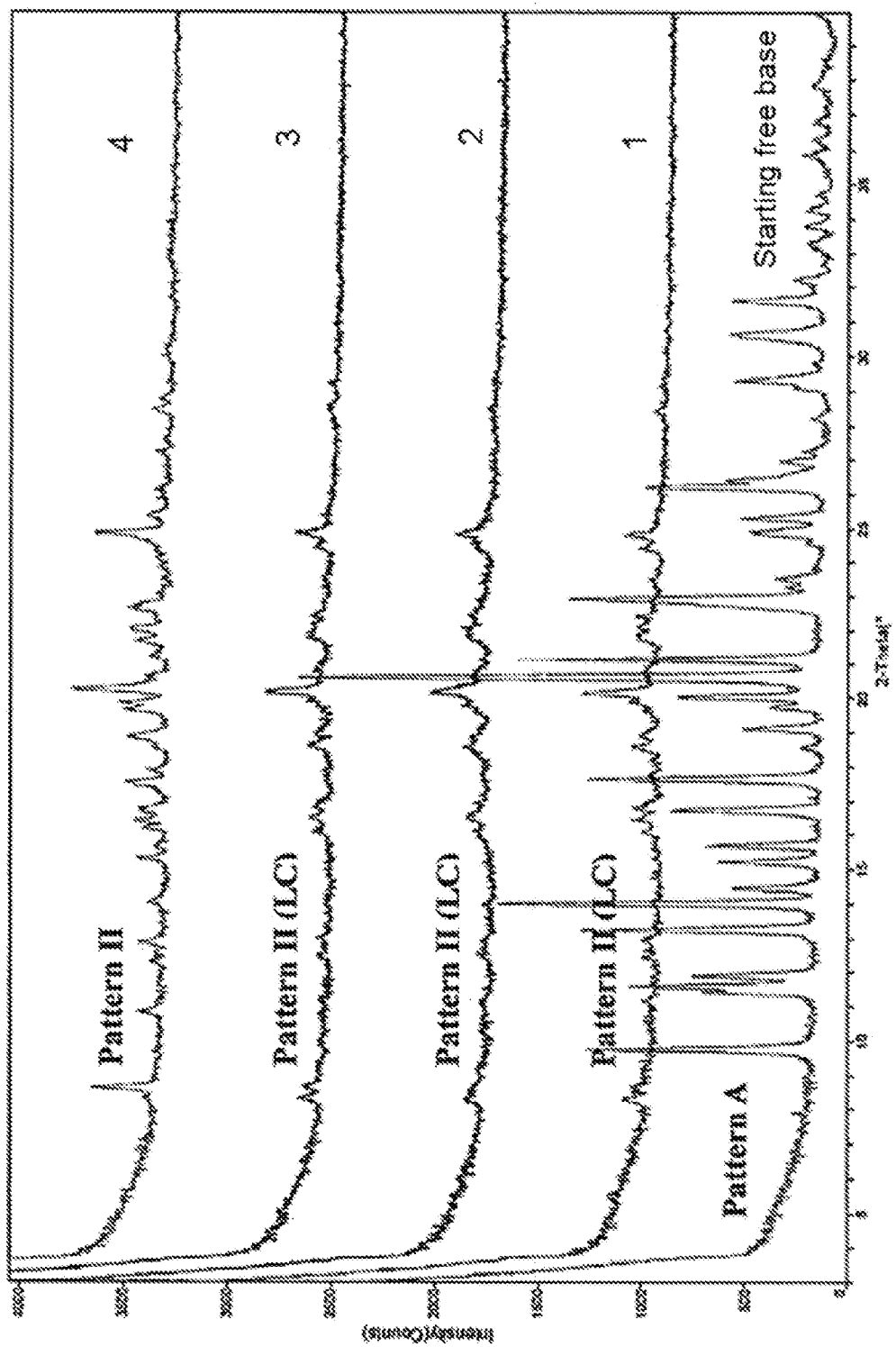
FIG. 6 shows an overlay of XRPD spectra of salt formation of Formula (I) with sulfuric acid in different solvents. 1—from acetone, 2—from ethyl acetate, 3—from acetonitrile, 4—isopropanol/water (95/5, v/v).
Figure 7:
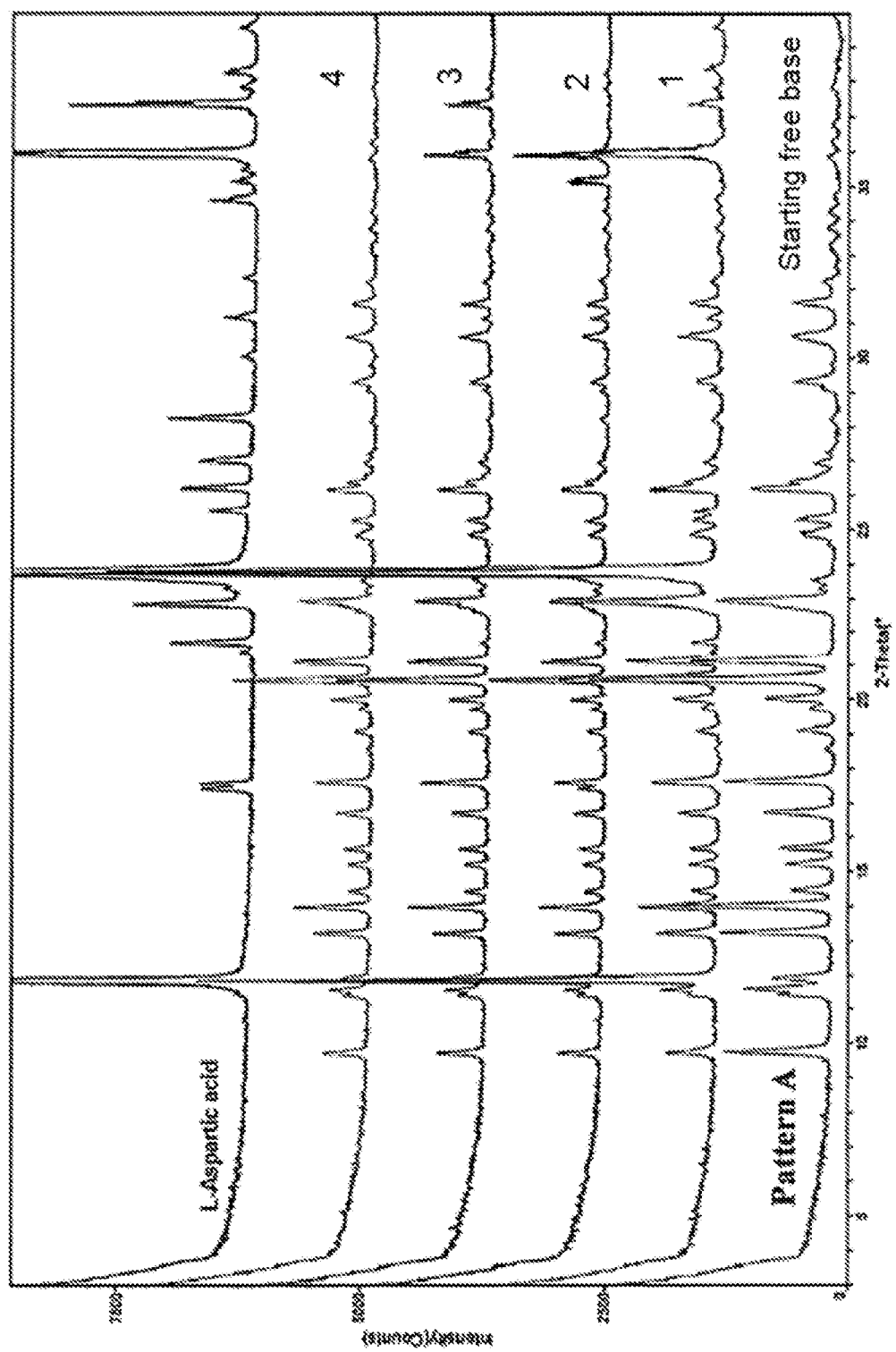
FIG. 7 shows an overlay of XRPD spectra of salt formation of Formula (I) with L-aspartic acid in different solvents. 1—from acetone, 2—from ethyl acetate, 3—from acetonitrile, 4—isopropanol/water (95/5, v/v).
Figure 8:
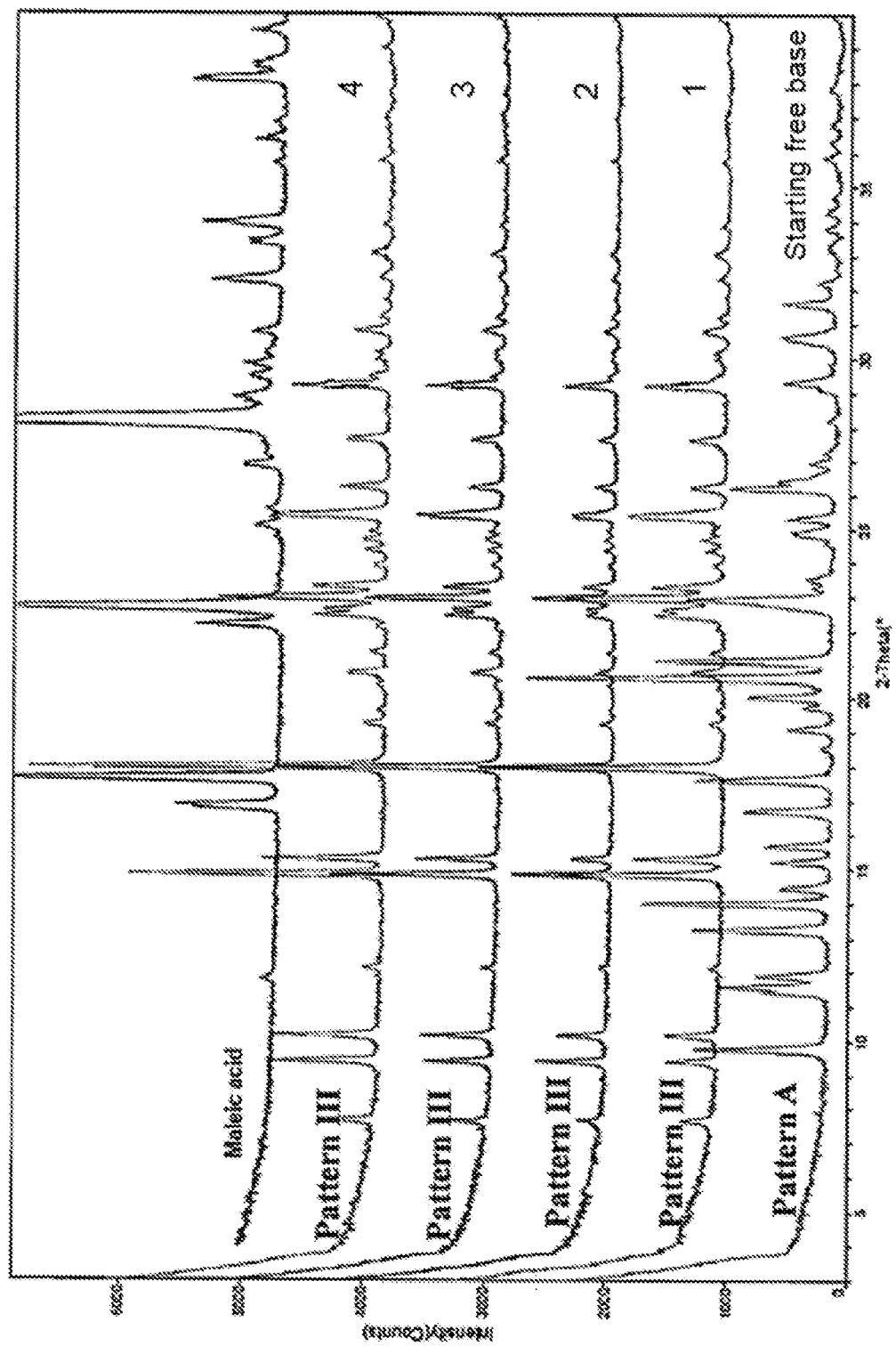
FIG. 8 shows an overlay of XRPD spectra of salt formation of Formula (I) with maleic acid in different solvents. 1—from acetone, 2—from ethyl acetate, 3—from acetonitrile, 4—isopropanol/water (95/5, v/v).
Figure 9:
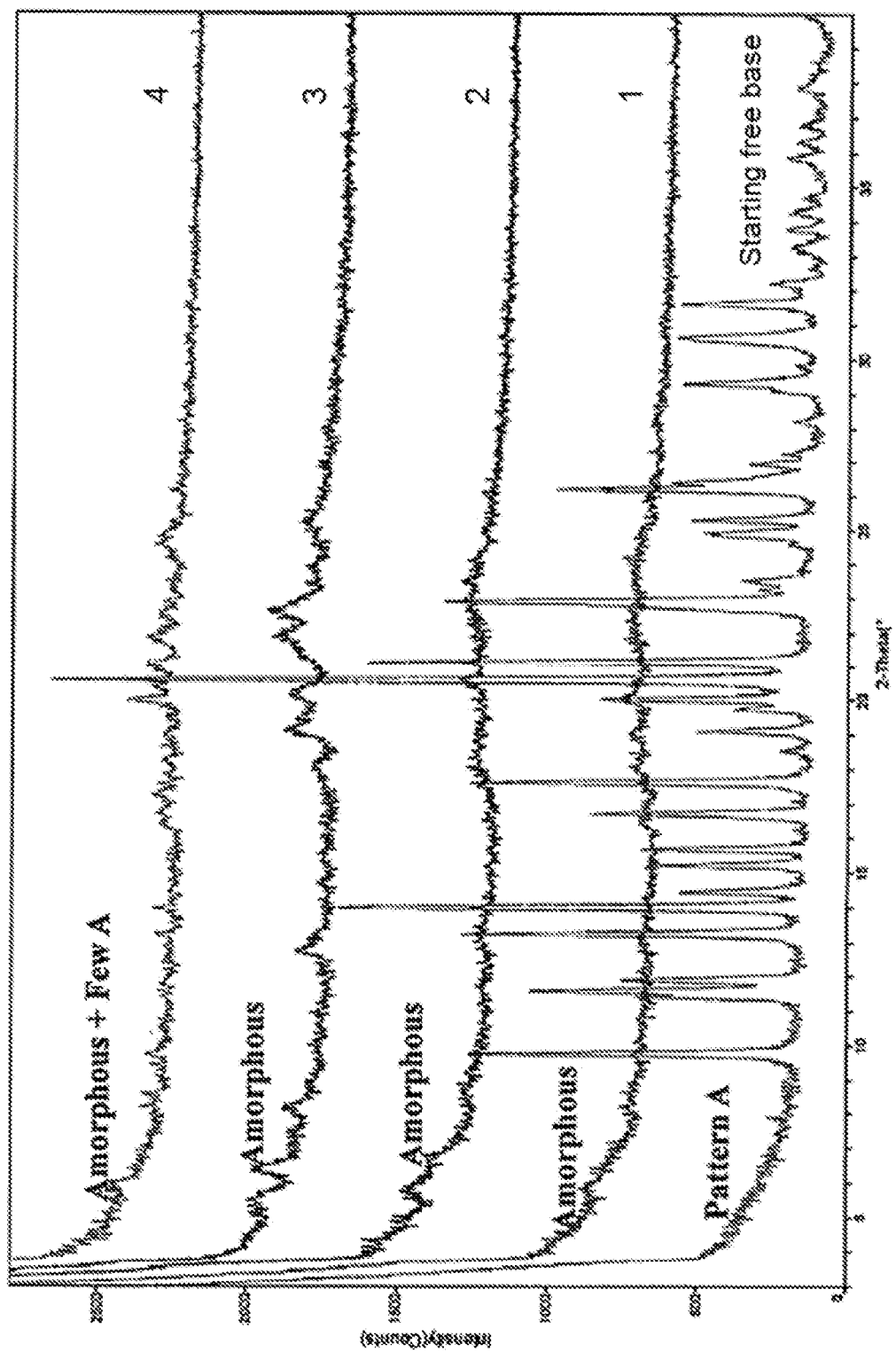
FIG. 9 shows an overlay of XRPD spectra of salt formation of Formula (I) with phosphoric acid in different solvents. 1—from acetone, 2—from ethyl acetate, 3—from acetonitrile, 4—isopropanol/water (95/5, v/v).
Figure 10:
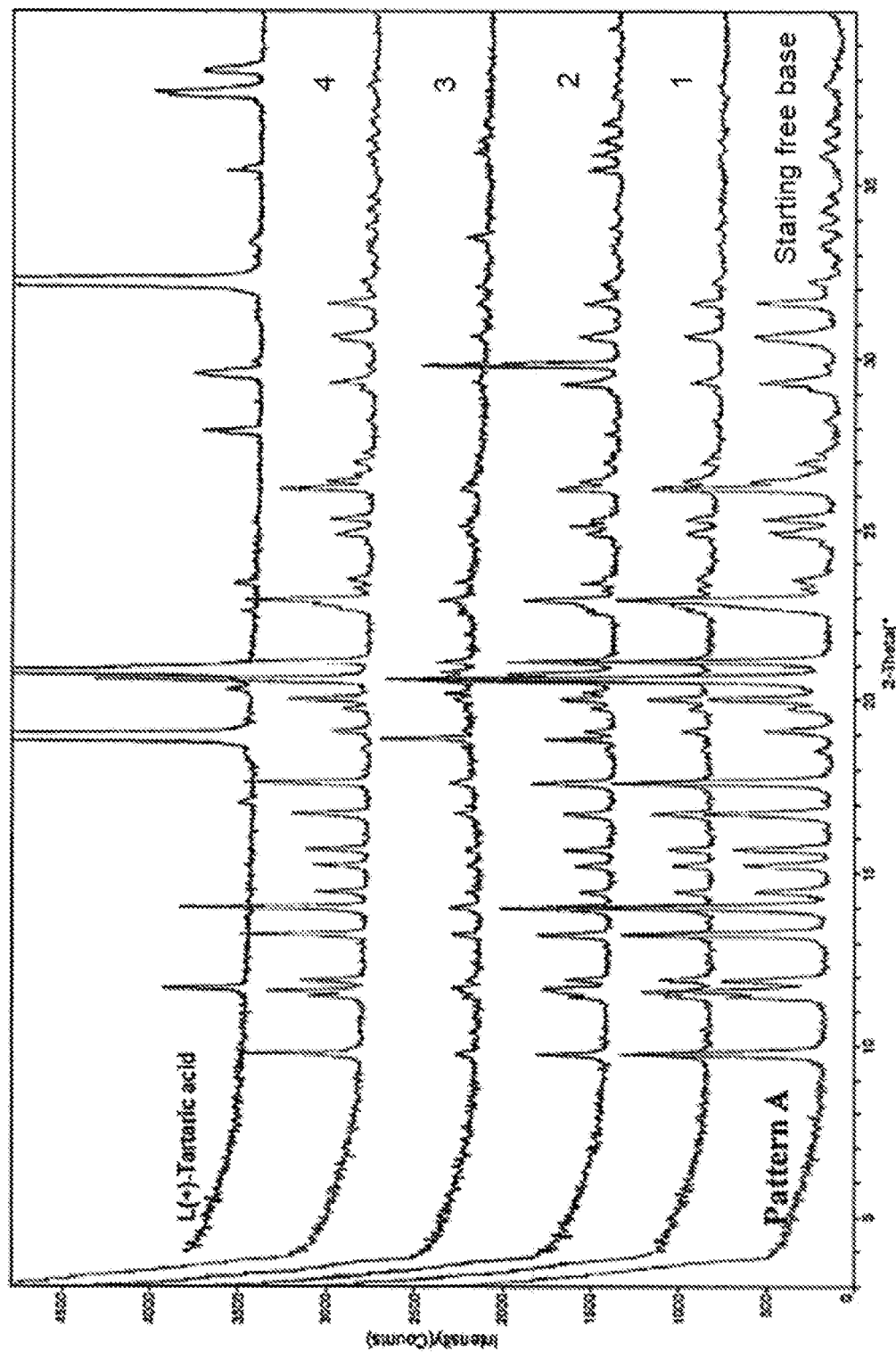
FIG. 10 shows an overlay of XRPD spectra of salt formation of Formula (I) with L(+)-tartaric acid in different solvents. 1—from acetone, 2—from ethyl acetate, 3—from acetonitrile, 4—isopropanol/water (95/5, v/v).
Figure 11:
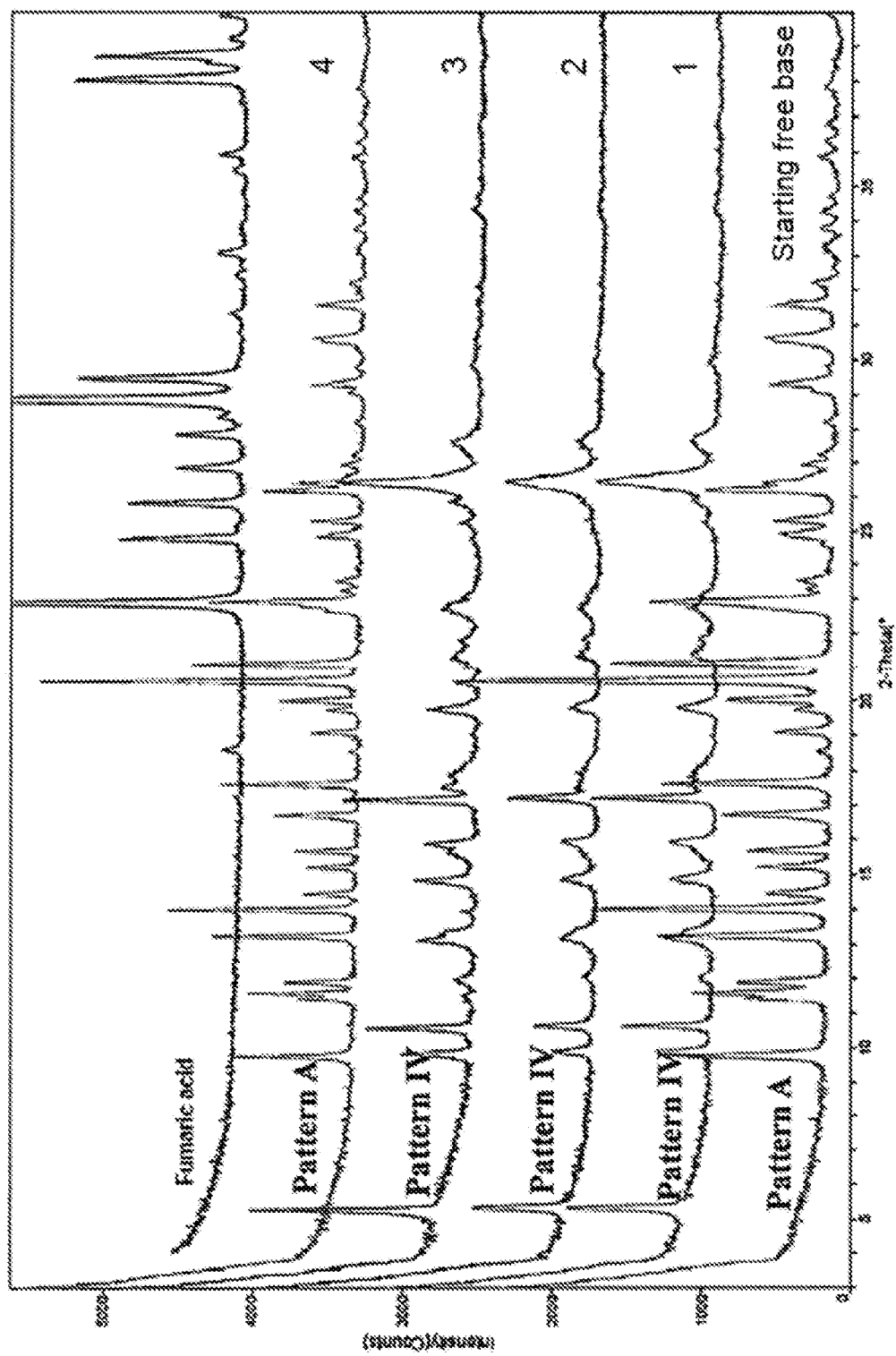
FIG. 11 shows an overlay of XRPD spectra of salt formation of Formula (I) with fumaric acid in different solvents. 1—from acetone, 2—from ethyl acetate, 3—from acetonitrile, 4—isopropanol/water (95/5, v/v).
Figure 12:
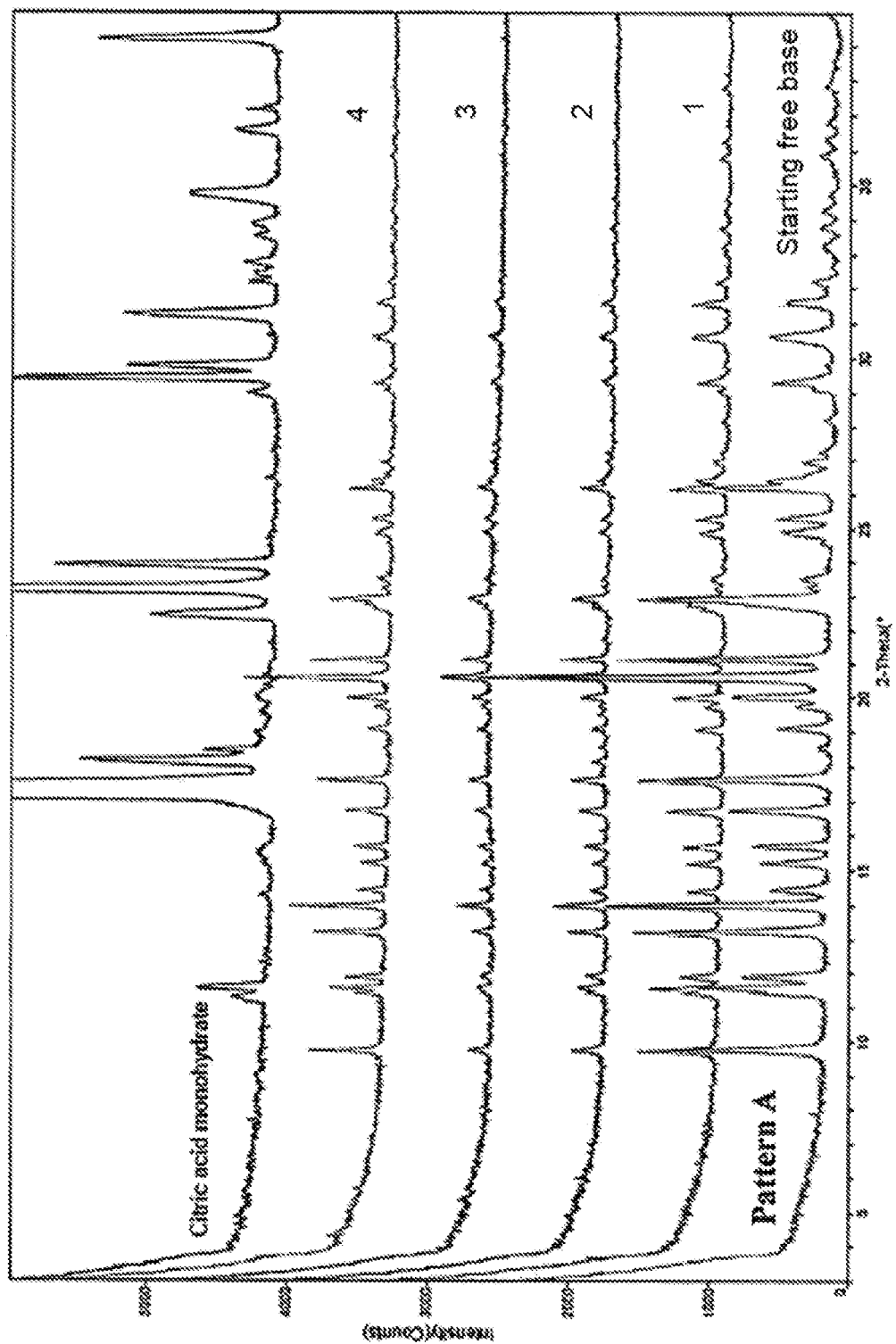
FIG. 12 shows an overlay of XRPD spectra of salt formation of Formula (I) with citric acid in different solvents. 1—from acetone, 2—from ethyl acetate, 3—from acetonitrile, 4—isopropanol/water (95/5, v/v).
Figure 13:
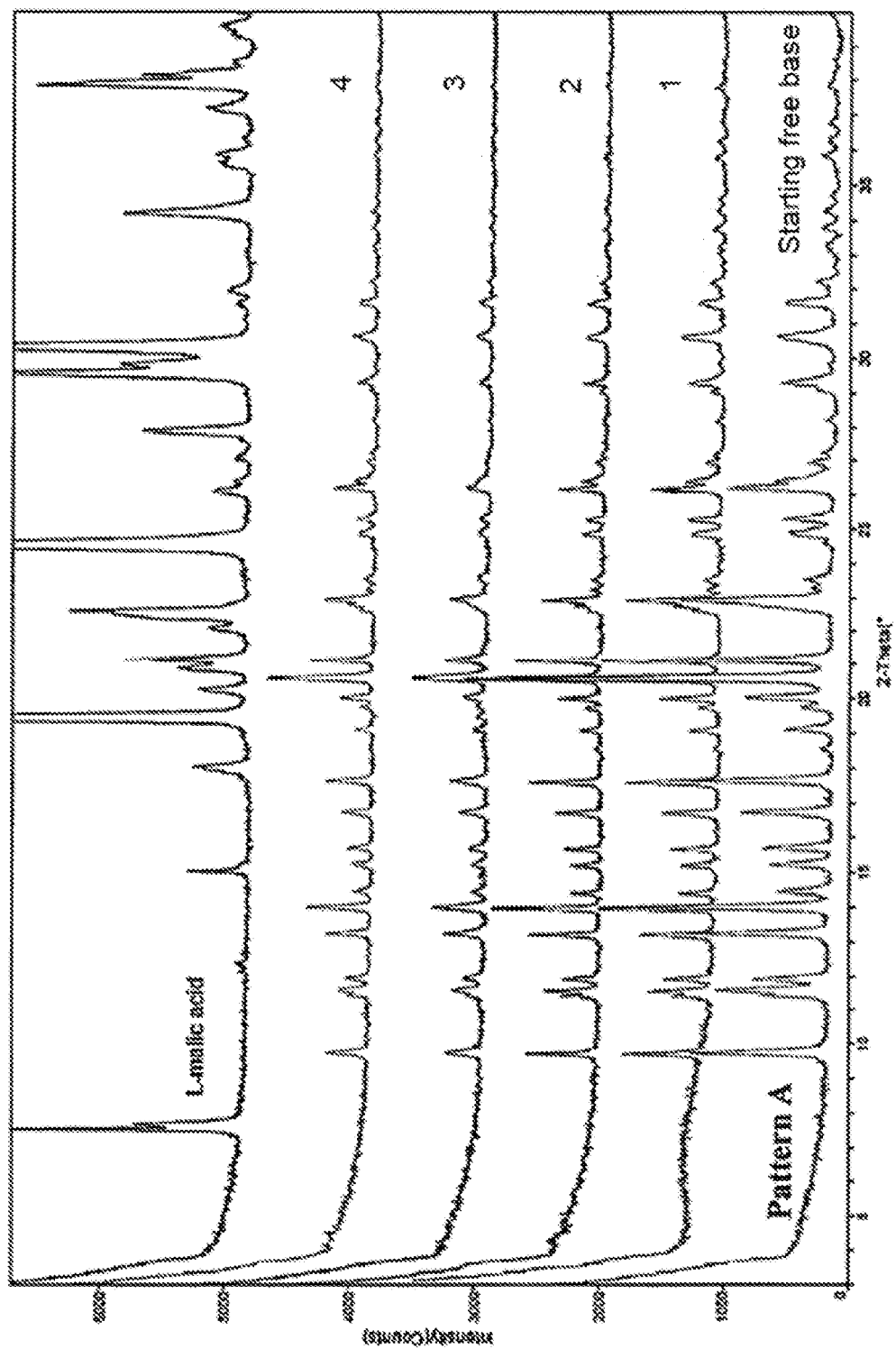
FIG. 13 shows an overlay of XRPD spectra of salt formation of Formula (I) with L-malic acid in different solvents. 1—from acetone, 2—from ethyl acetate, 3—from acetonitrile, 4—isopropanol/water (95/5, v/v).
Figure 14:
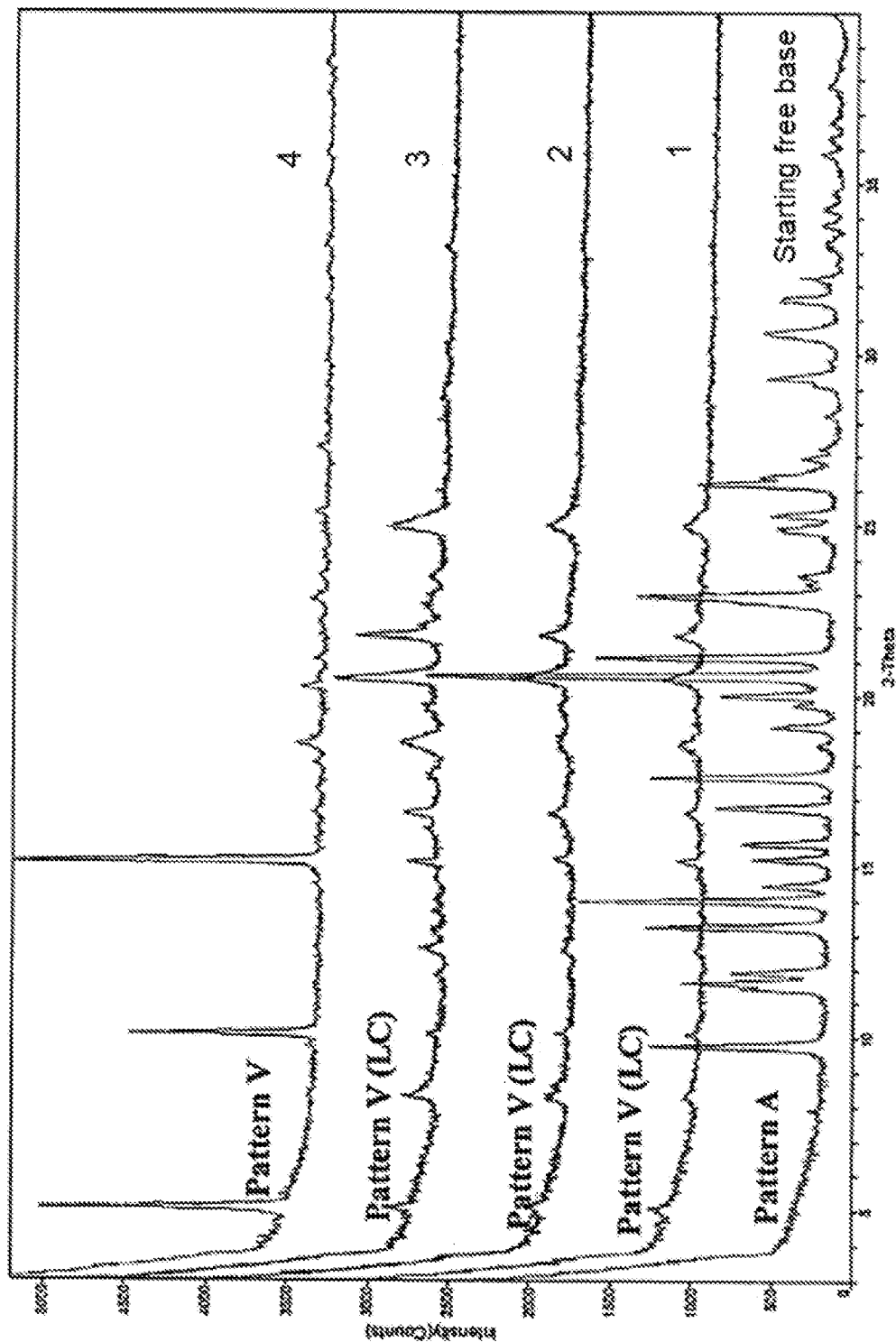
FIG. 14 shows an overlay of XRPD spectra of salt formation of Formula (I) with methane sulfonic acid in different solvents. 1—from acetone, 2—from ethyl acetate, 3—from acetonitrile, 4—isopropanol/water (95/5, v/v).
Figure 15:
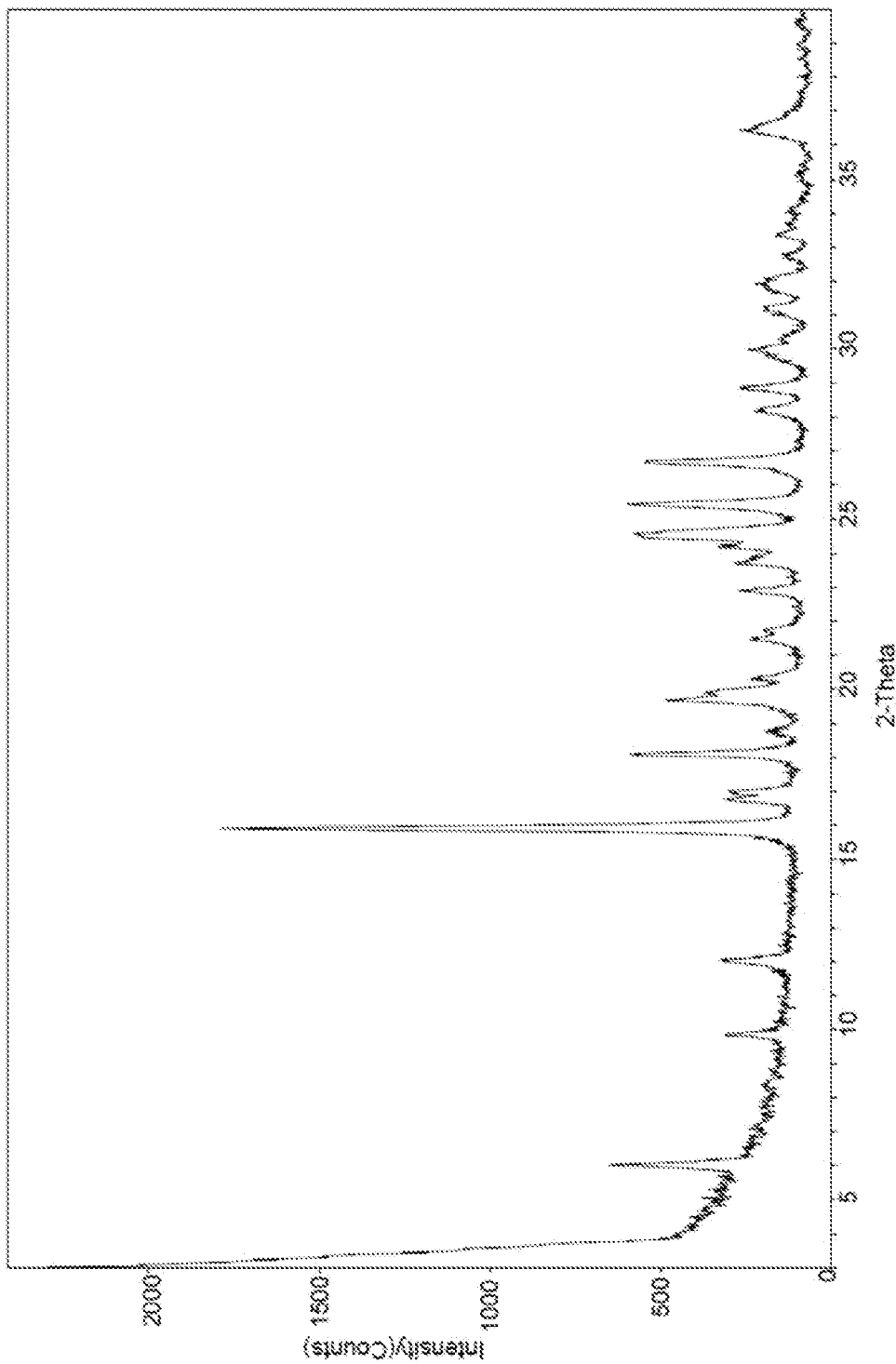
FIG. 15 shows XRPD pattern of hydrochloride salt of Formula (I). (Pattern I)
Figure 16:
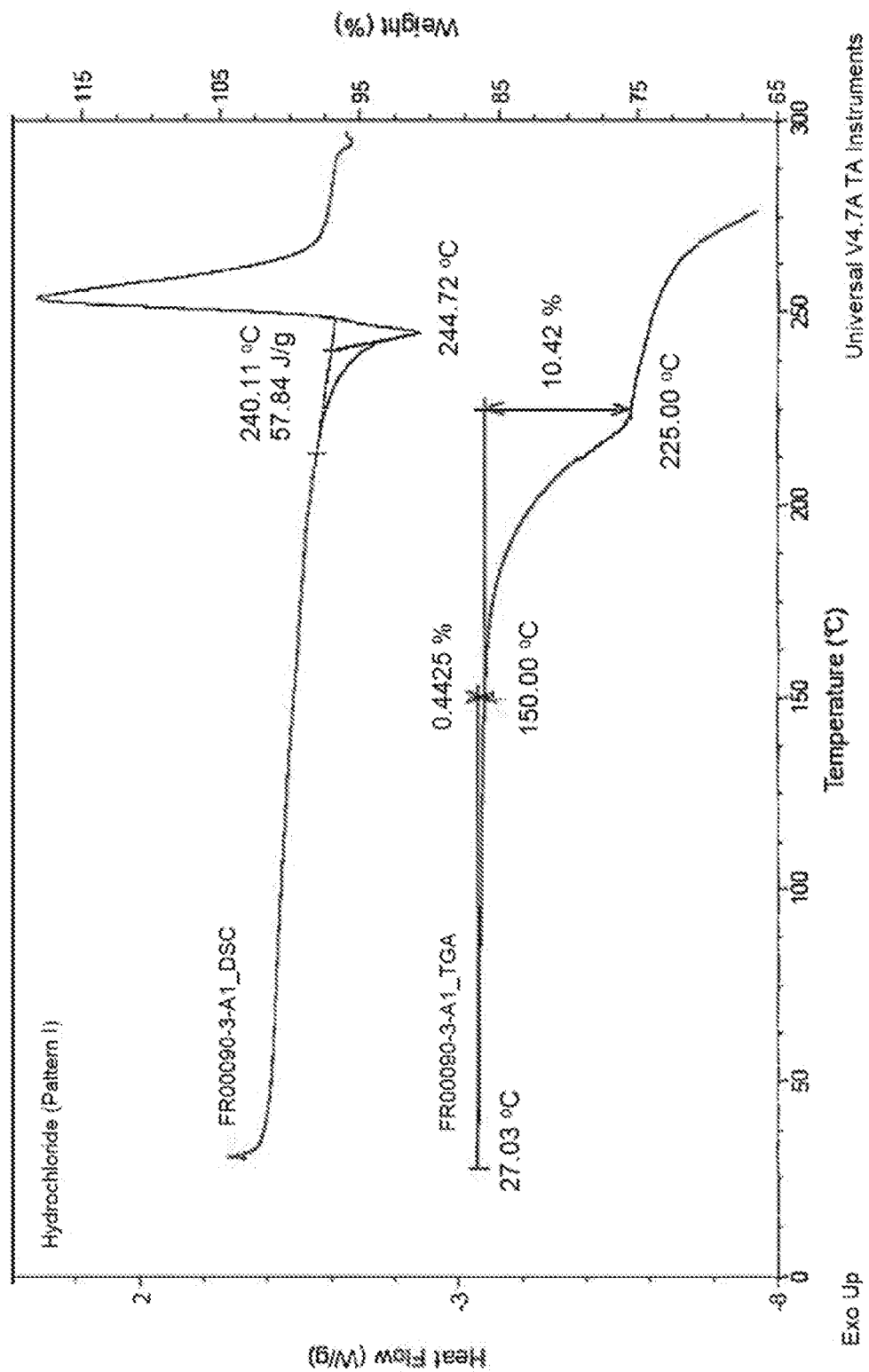
FIG. 16 shows an overlay of DSC and TGA spectra of hydrochloride salt of Formula (I). (Pattern I)
Figure 17:
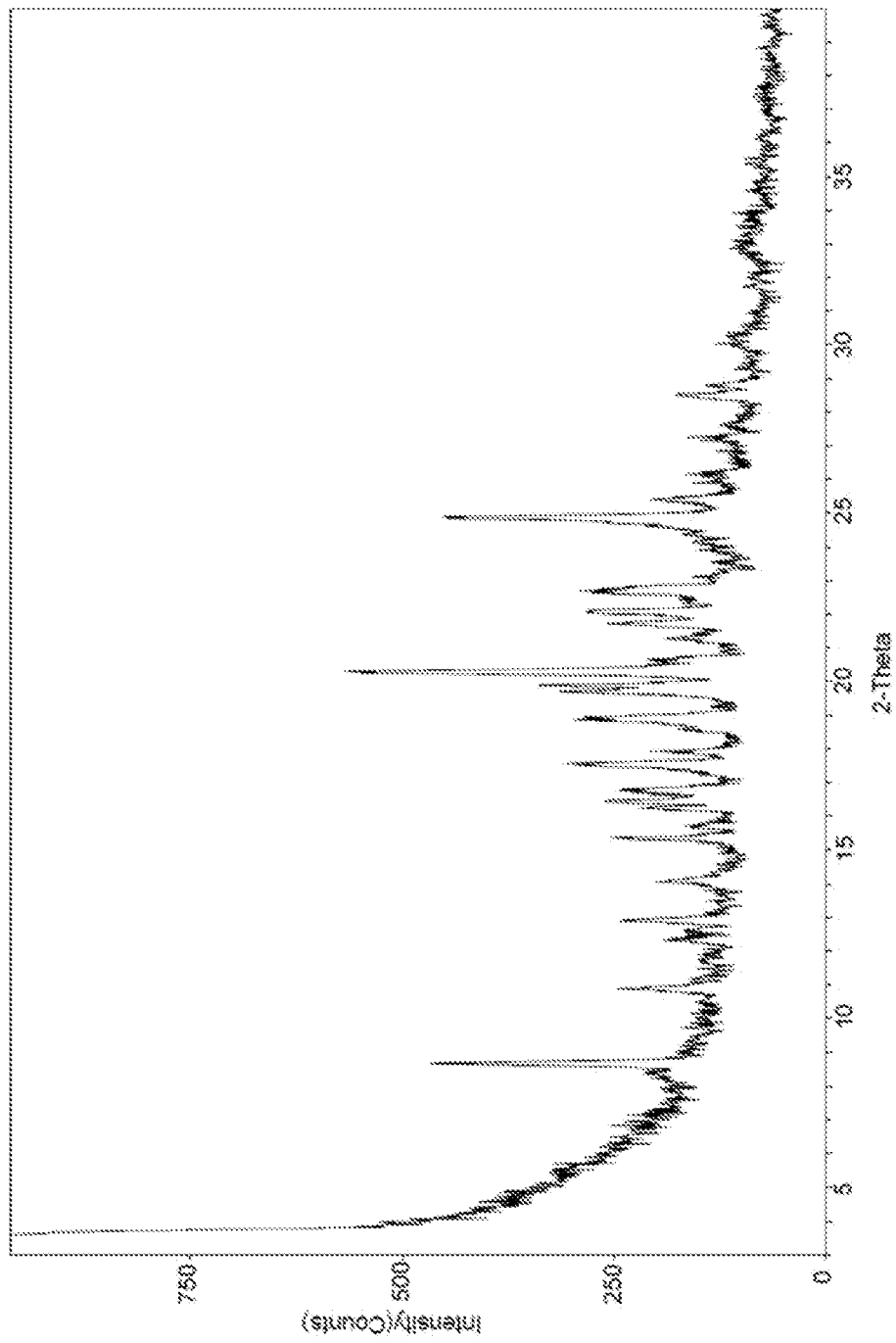
FIG. 17 shows XRPD pattern of sulfate salt of Formula (I). (Pattern II)
Figure 18:
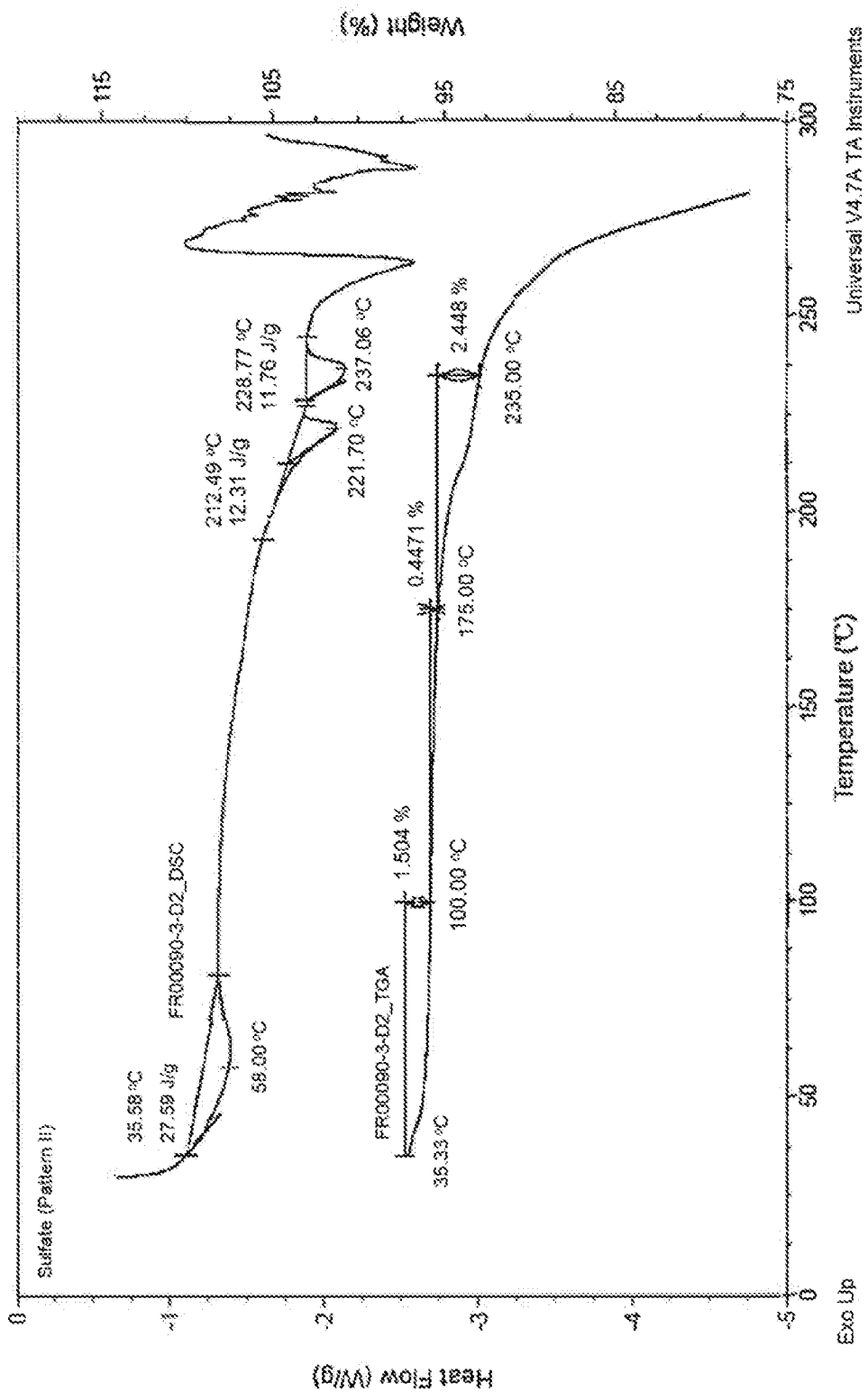
FIG. 18 shows an overlay of DSC and TGA spectra of sulfate salt of Formula (I). (Pattern II)
Figure 19:
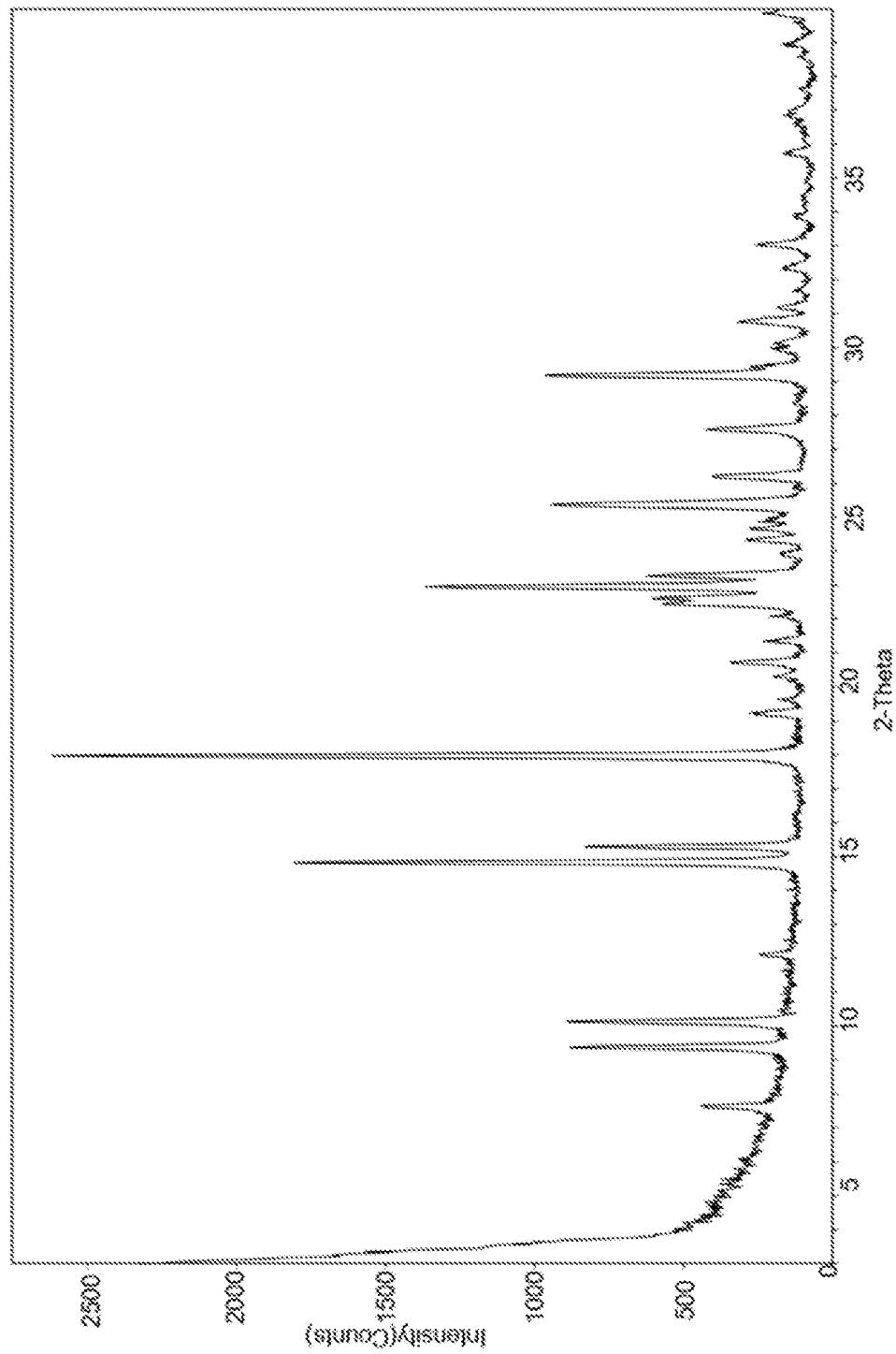
FIG. 19 shows XRPD pattern of maleate salt of Formula (I). (Pattern III)
Figure 20:
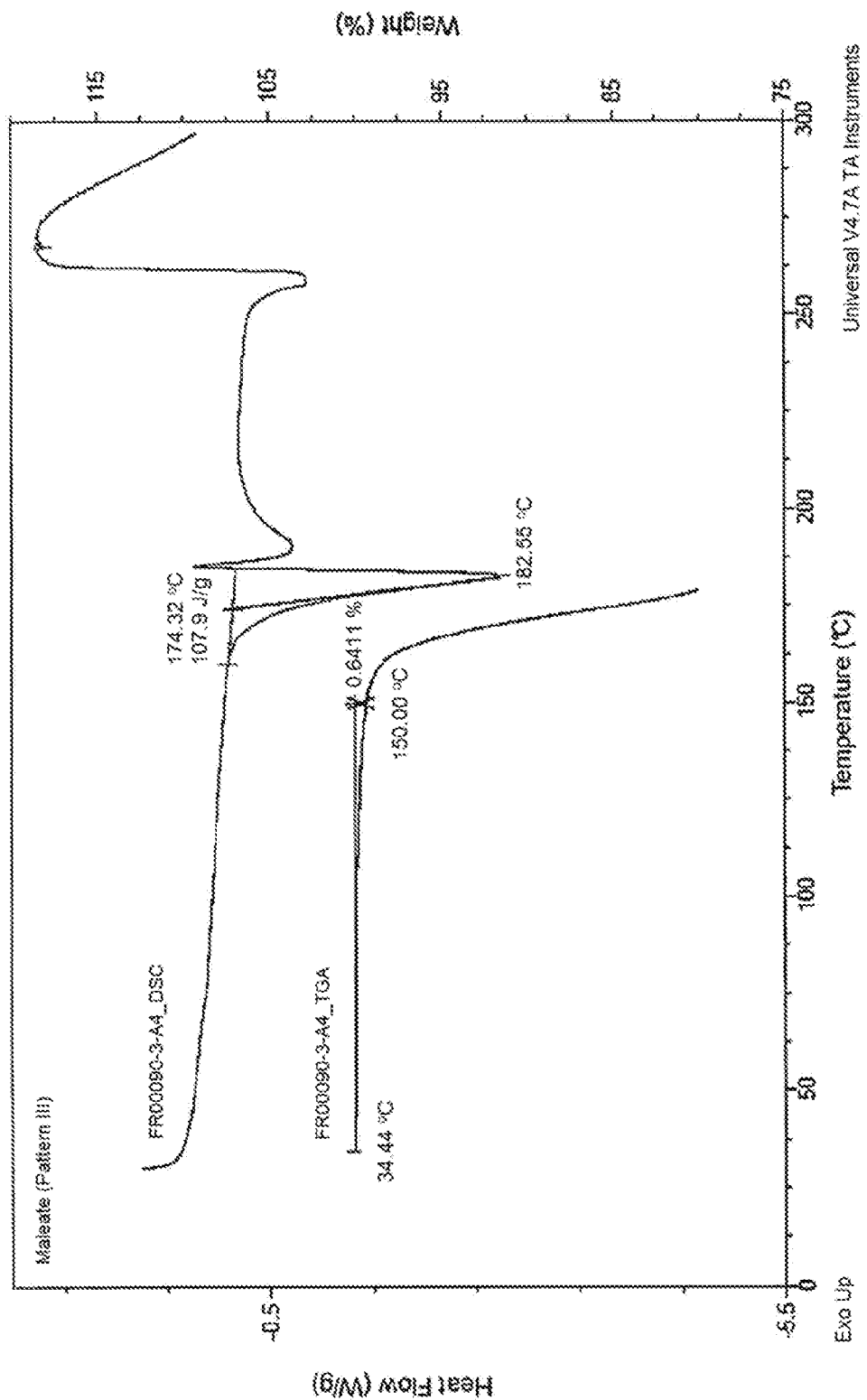
FIG. 20 shows an overlay of DSC and TGA spectra of maleate salt of Formula (I). (Pattern III)
Figure 21:
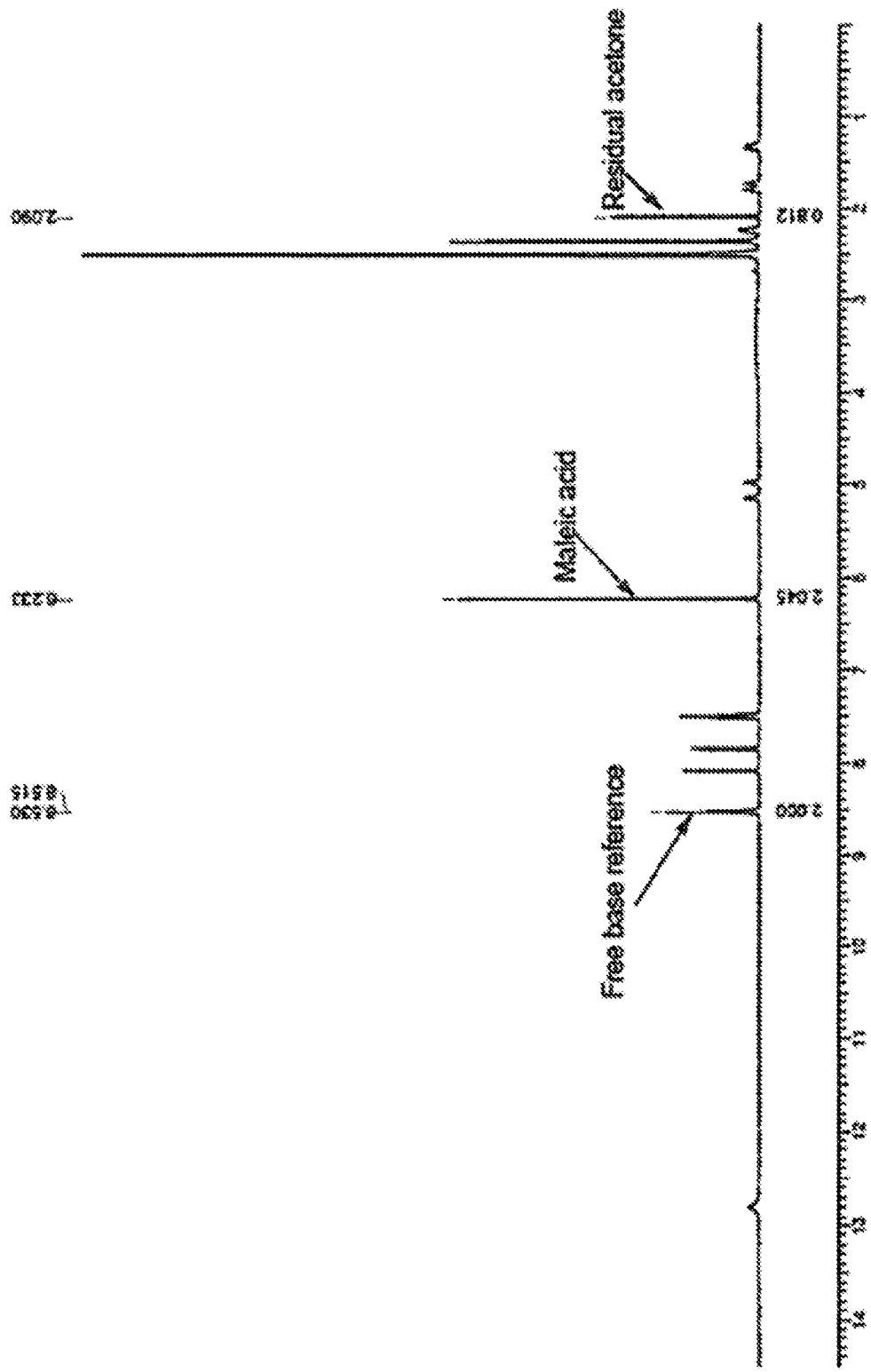
FIG. 21 shows a $^1$H-NMR spectrum of maleate salt of Formula (I). (Pattern III)
Figure 22:
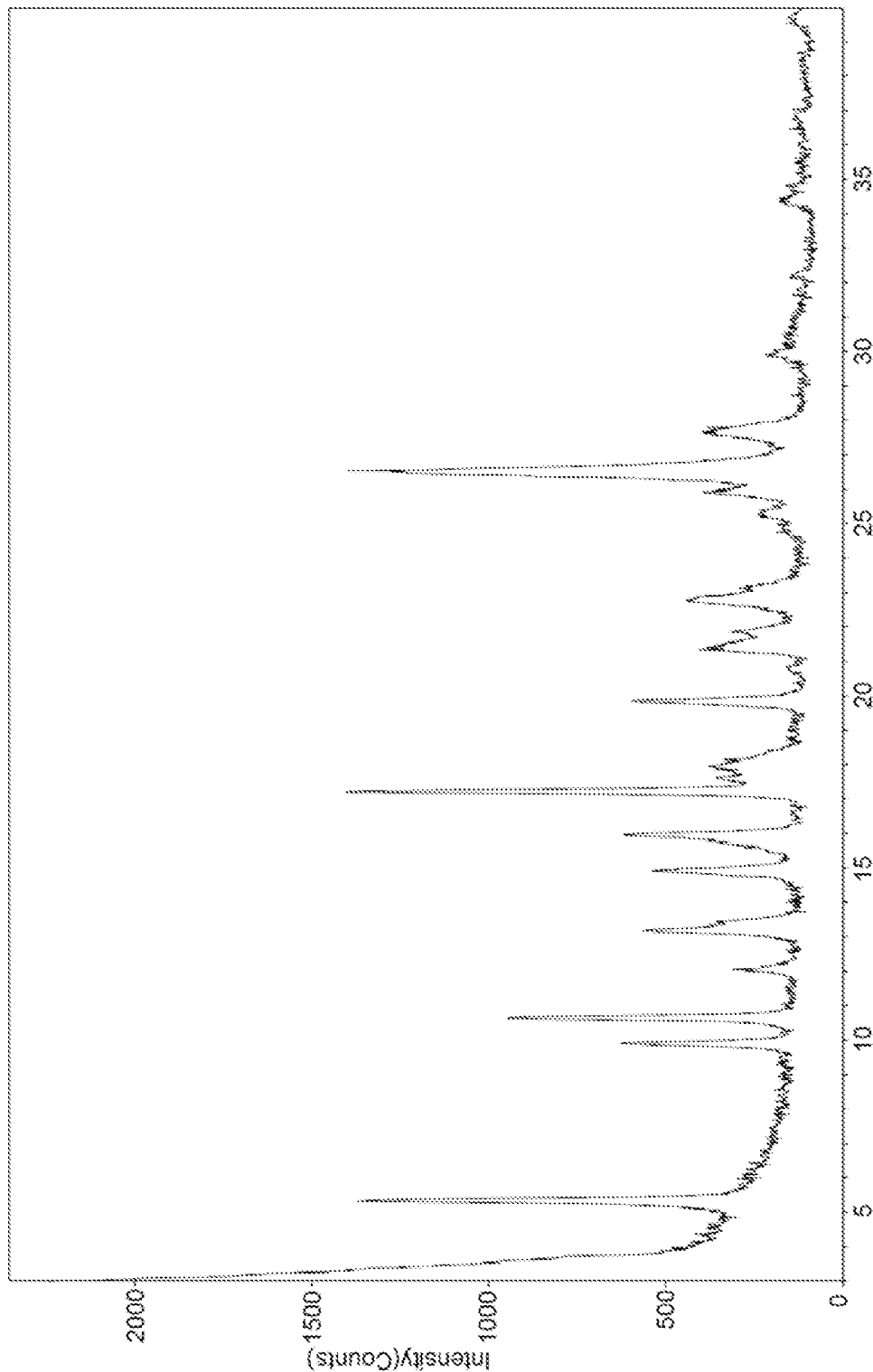
FIG. 22 shows XRPD pattern of fumarate salt of Formula (I). (Pattern IV)
Figure 23:
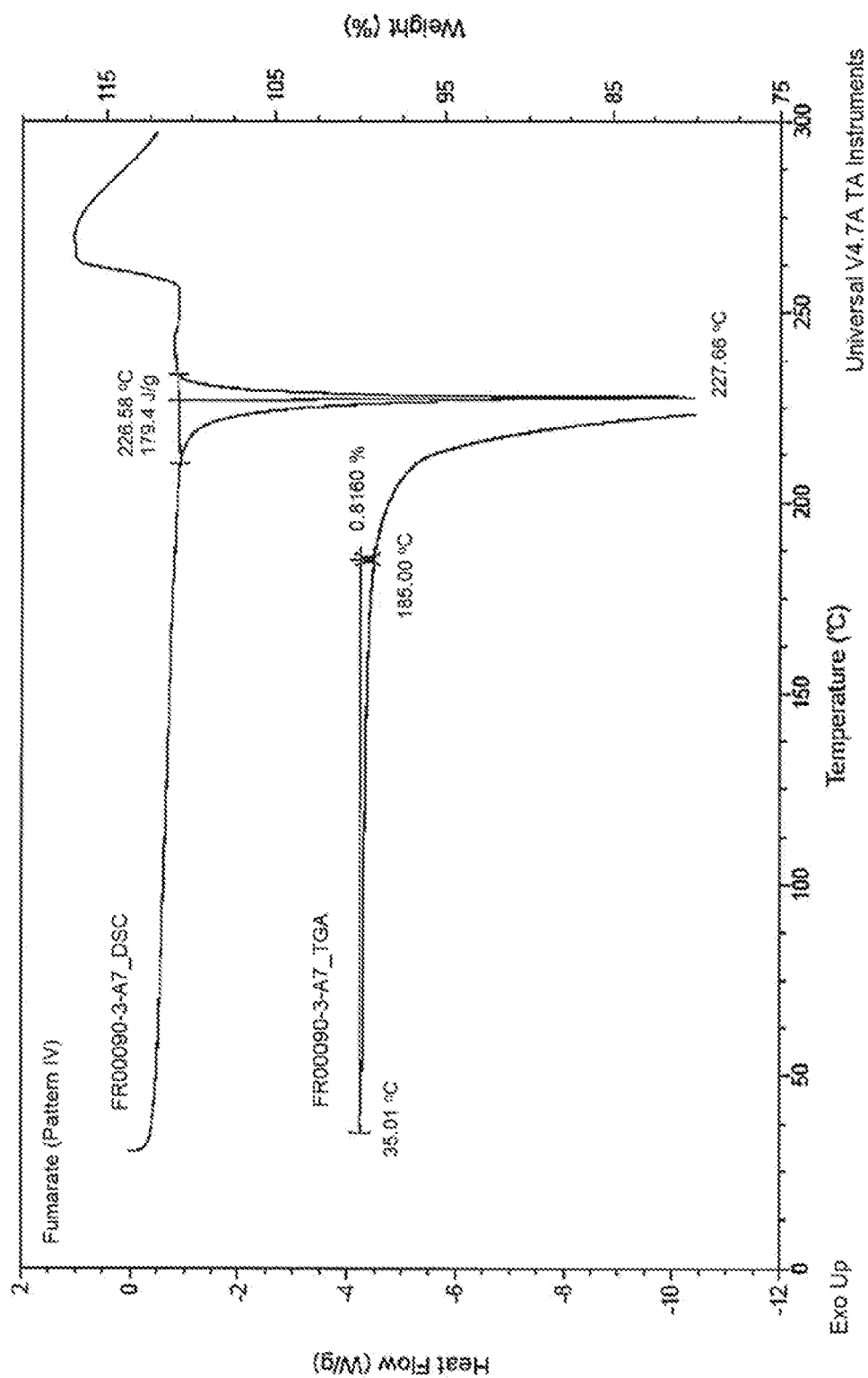
FIG. 23 shows an overlay of DSC and TGA spectra of fumarate salt of Formula (I). (Pattern IV)
Figure 24:
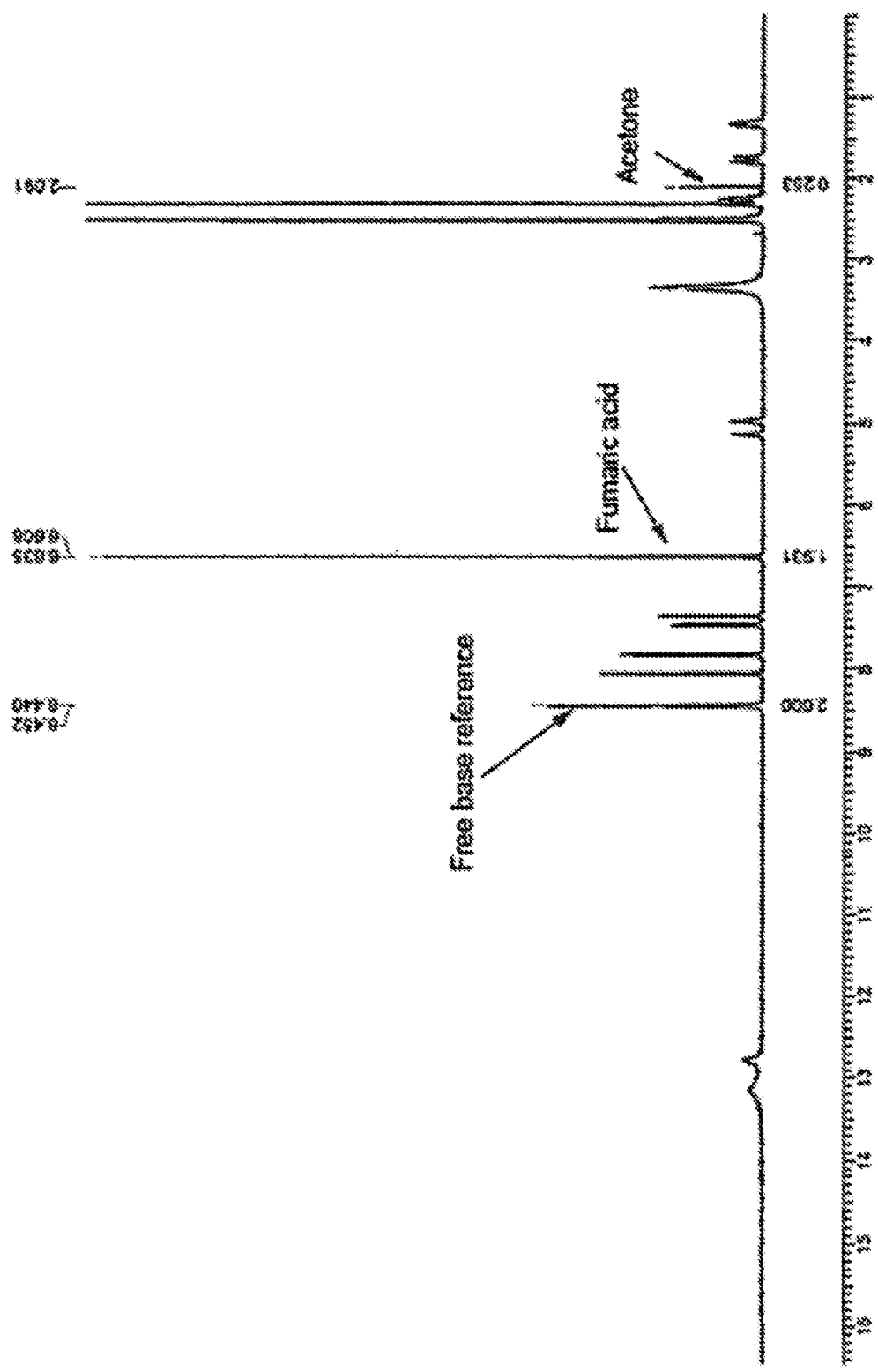
FIG. 24 shows a $^1$H-NMR spectrum of fumarate salt of Formula (I). (Pattern IV)
Figure 25:
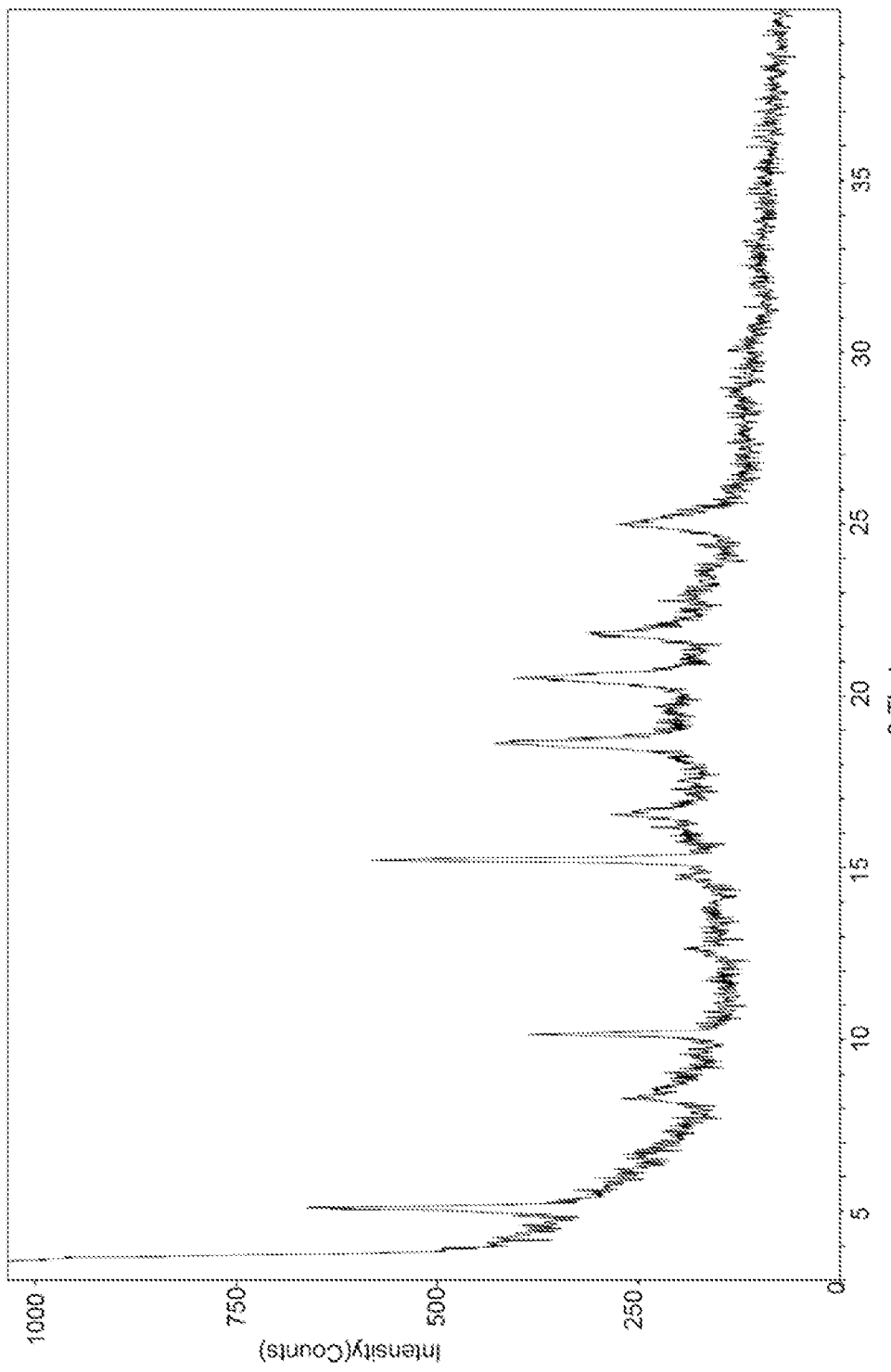
FIG. 25 shows XRPD pattern of mesylate salt of Formula (I). (Pattern V)
Figure 26:
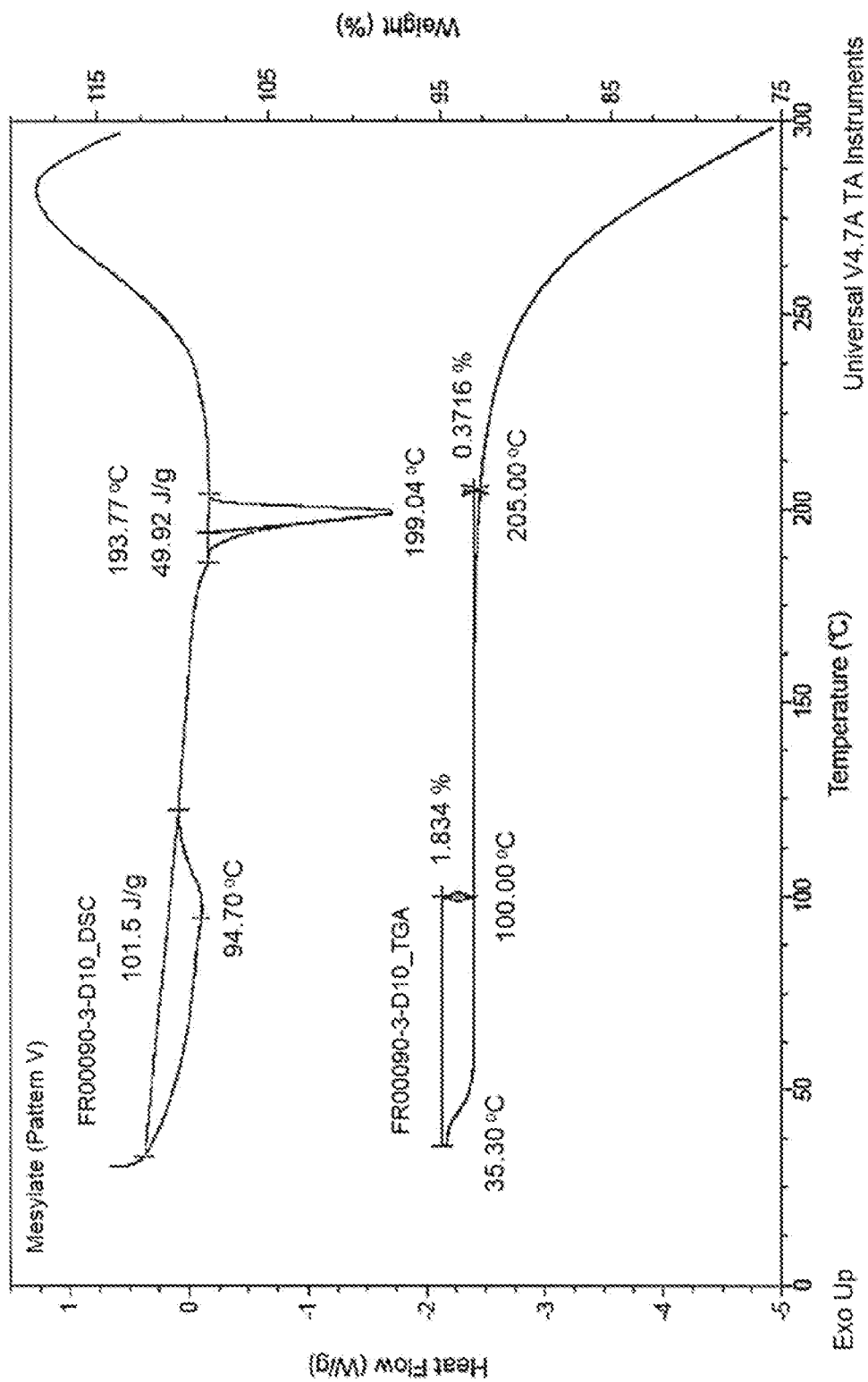
FIG. 26 shows an overlay of DSC and TGA spectra of mesylate salt of Formula (I). (Pattern V)
Figure 27:
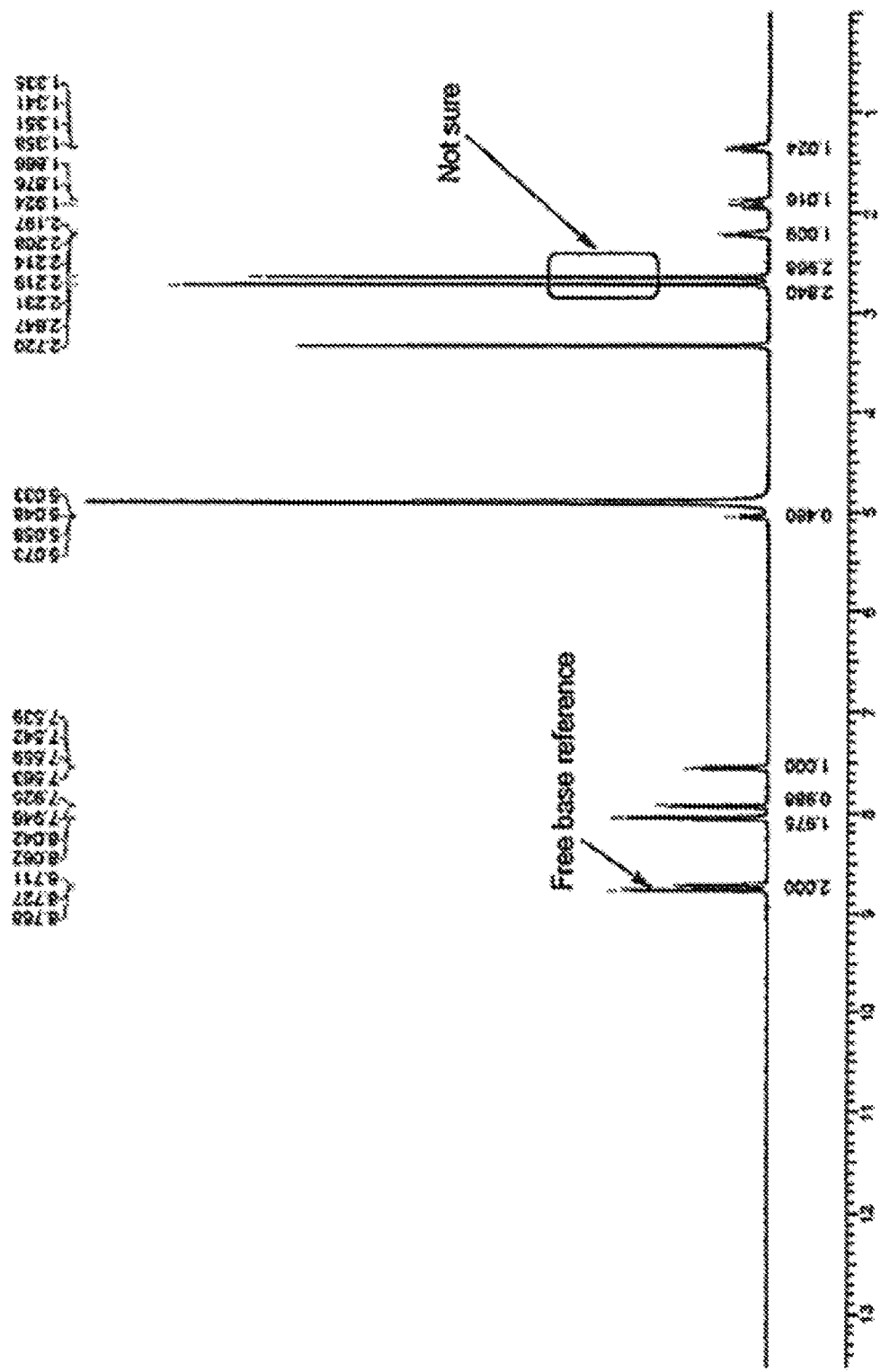
FIG. 27 shows a $^1$H-NMR spectrum of mesylate salt of Formula (I). (Pattern V)
Figure 28:
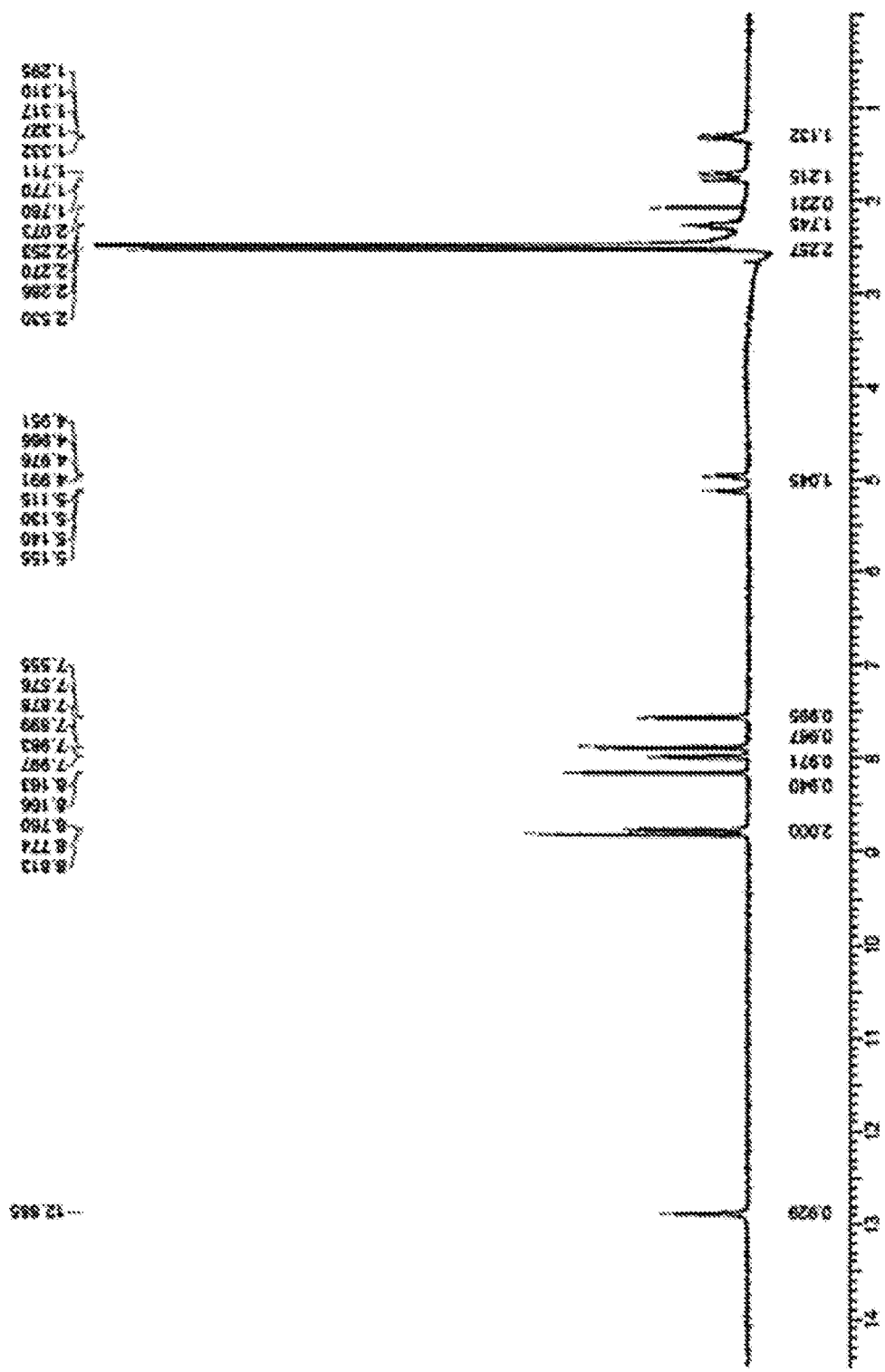
FIG. 28 shows a $^1$H-NMR spectrum of mono-hydrochloride salt of Formula (I). (Pattern I)
Figure 29:
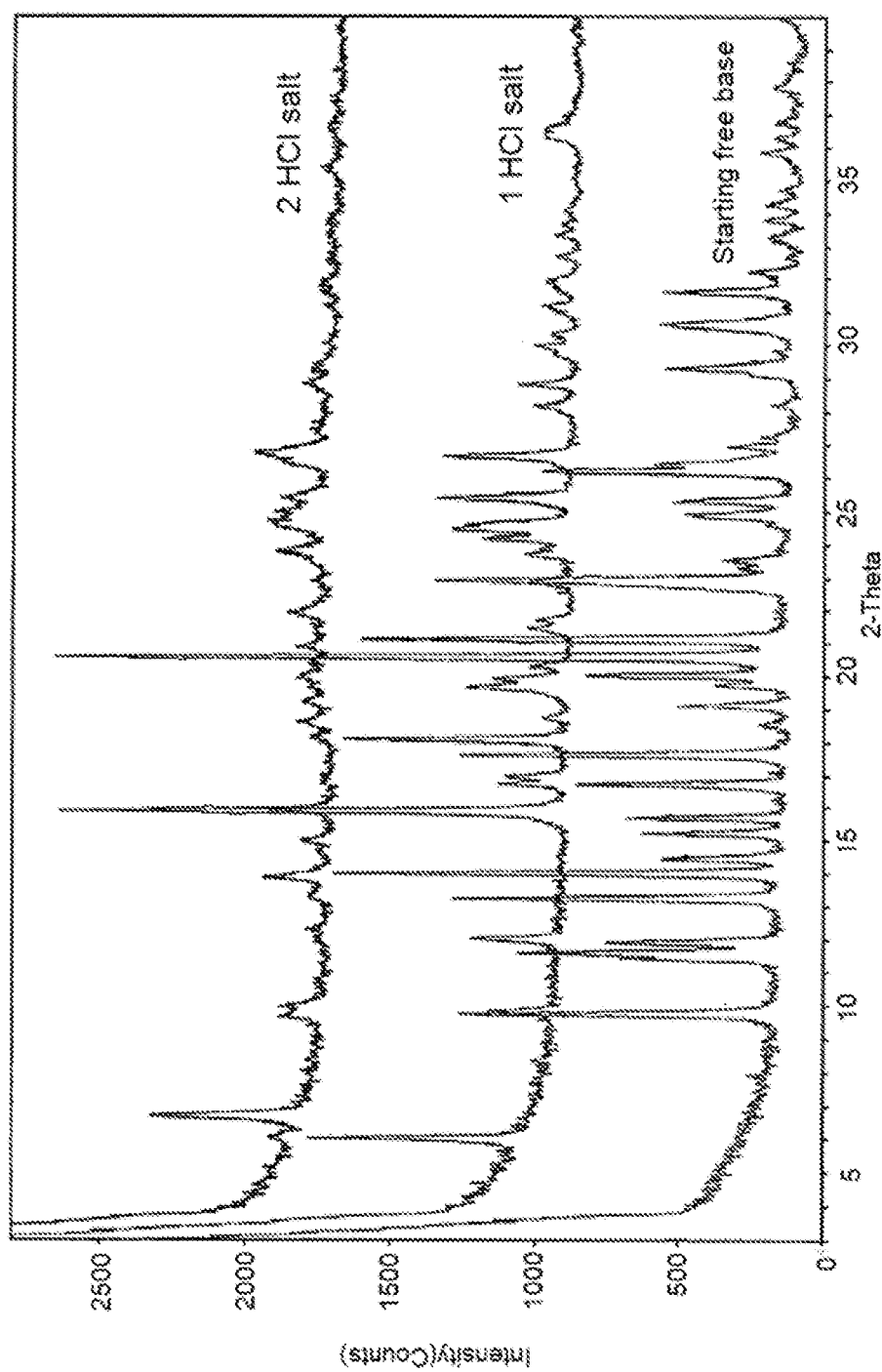
FIG. 29 shows an overlay of XRPD spectra of mono- and di-hydrochloride salt of Formula (I).
Figure 30:
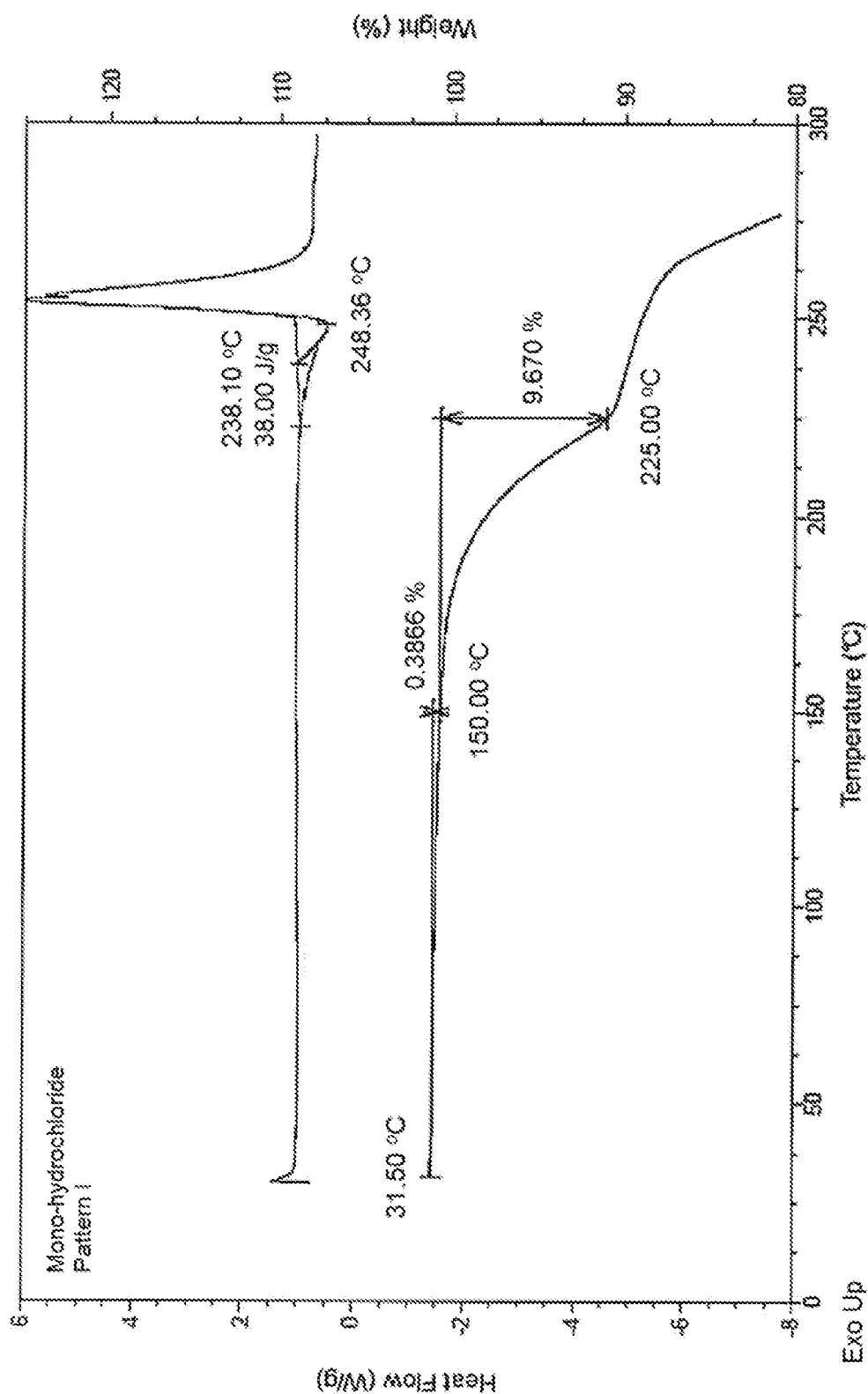
FIG. 30 shows an overlay of DSC and TGA spectra of monohydrochloride salt of Formula (I). (Pattern I)
Figure 31:
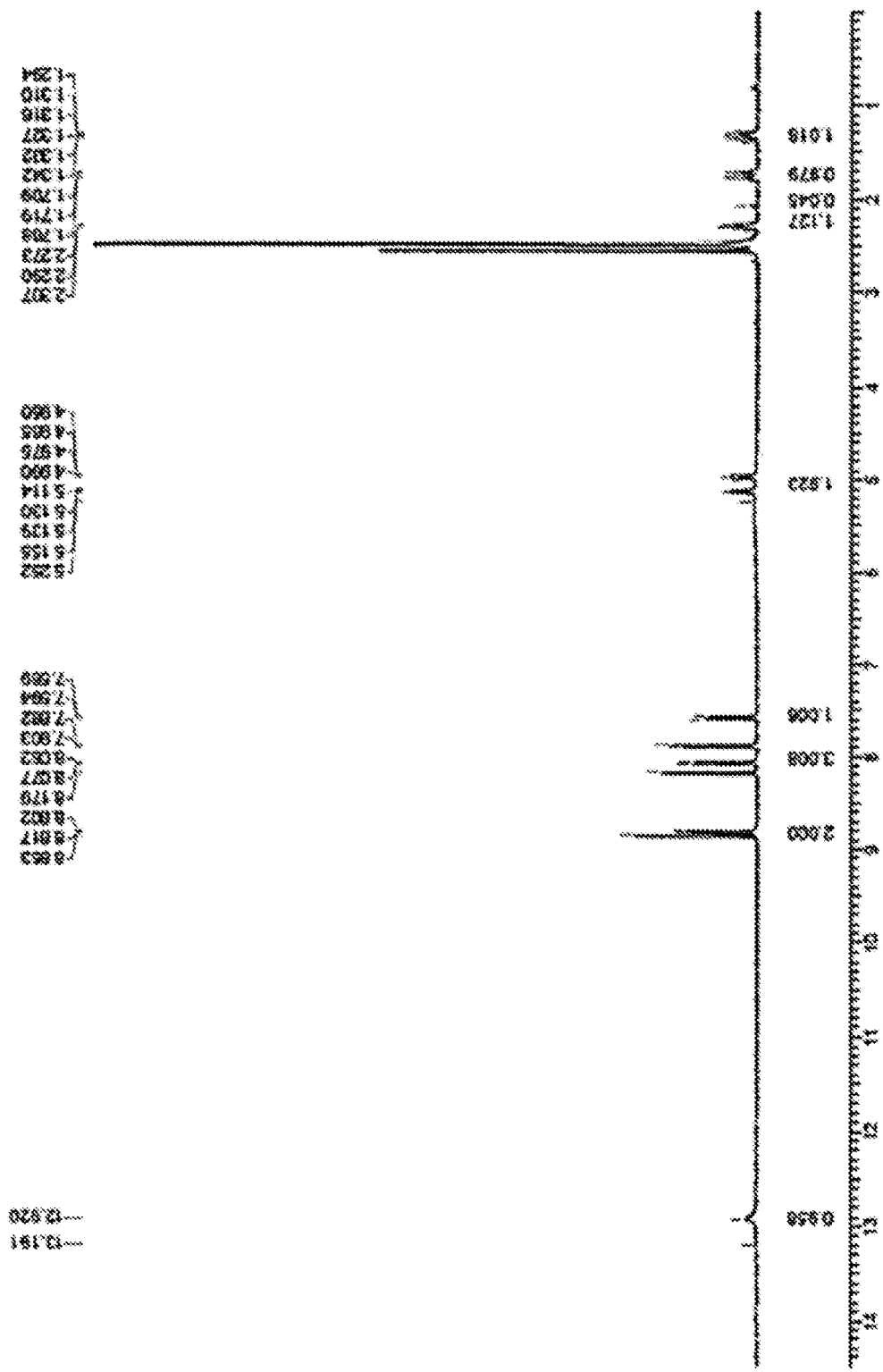
FIG. 31 shows a $^1$H-NMR spectrum of di-hydrochloride salt of Formula (I). (Pattern VI)
Figure 32:
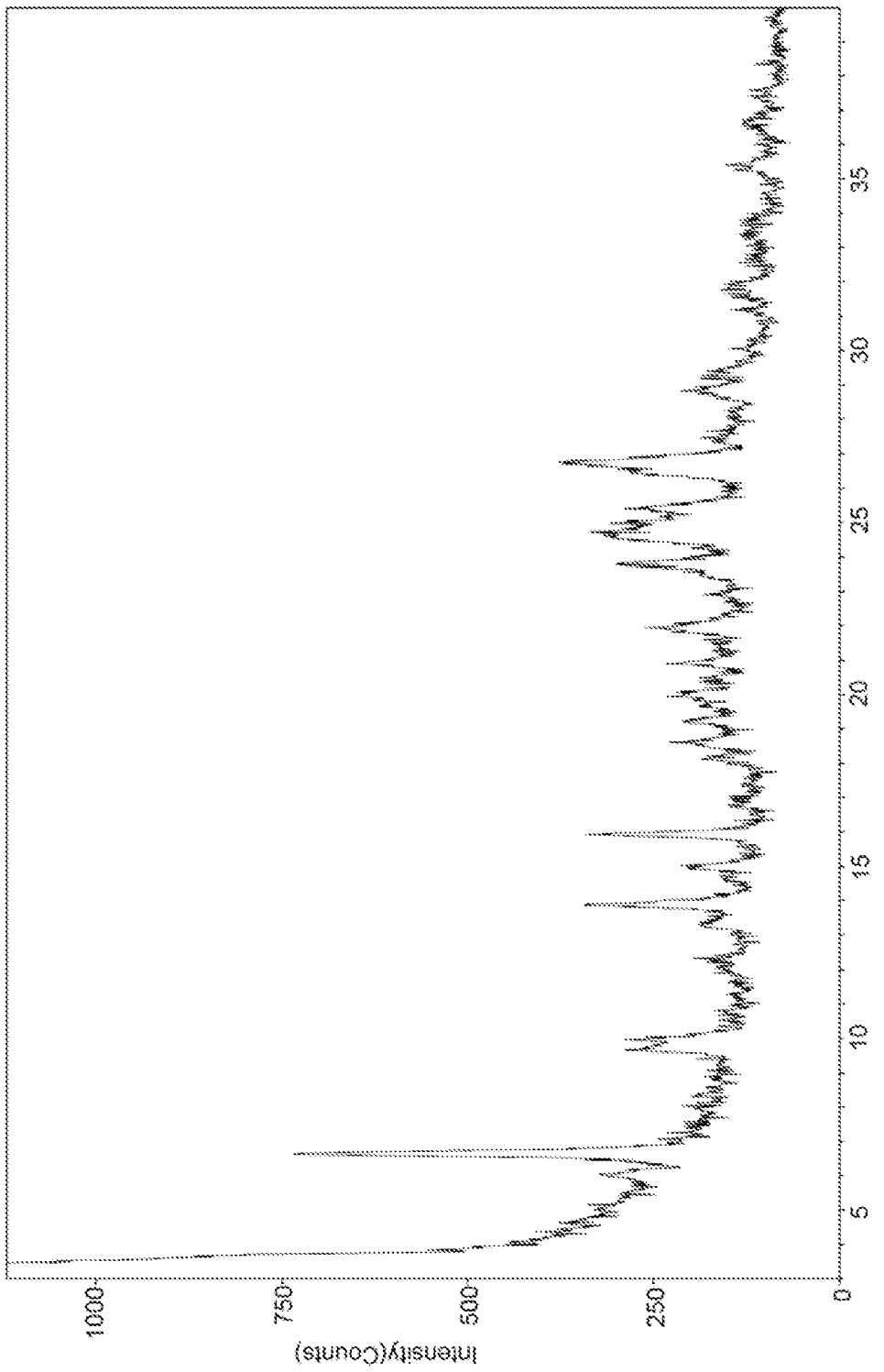
FIG. 32 shows XRPD pattern of di-hydrochloride salt of Formula (I). (Pattern VI)
Figure 33:
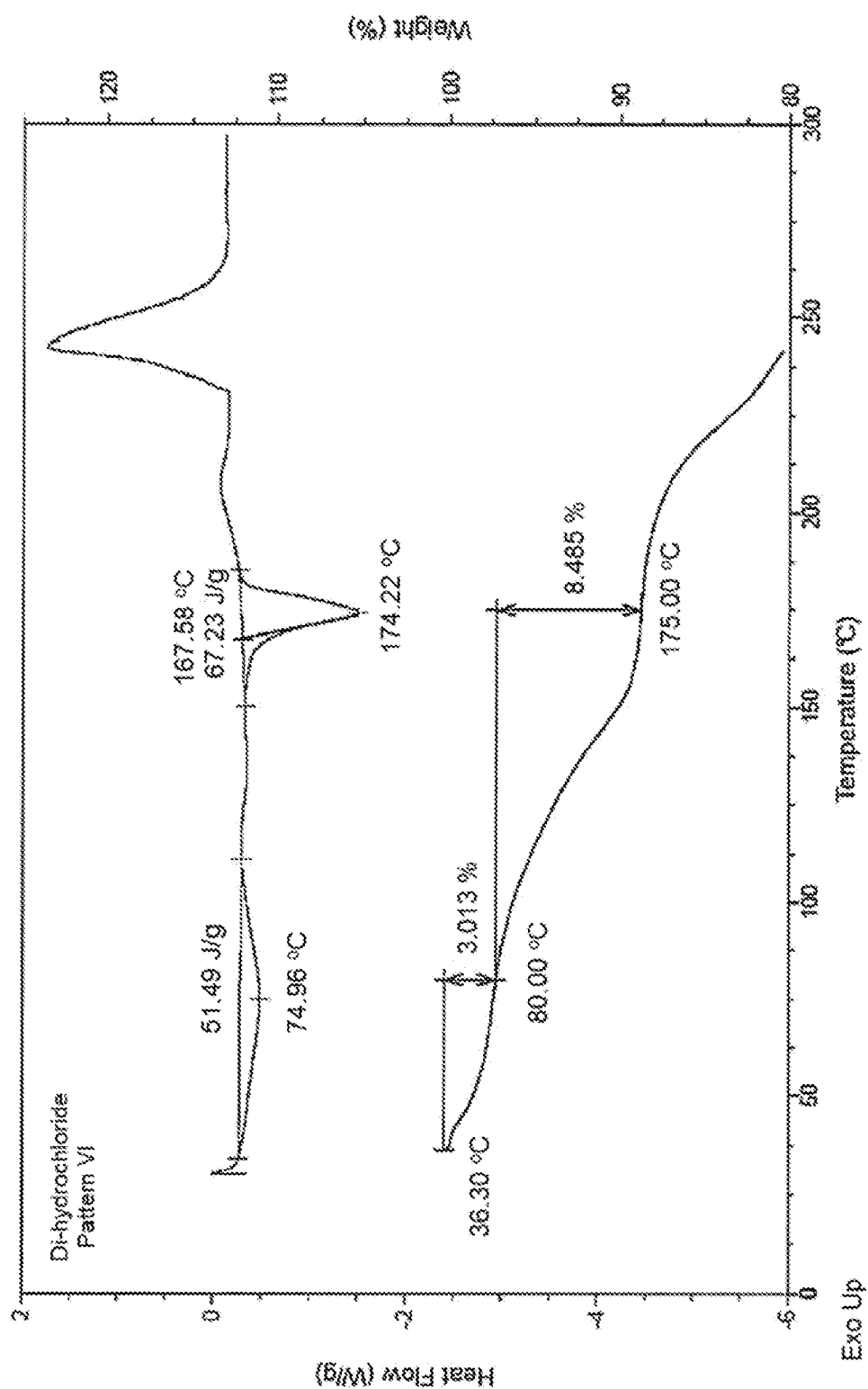
FIG. 33 shows an overlay of DSC and TGA spectra of di-hydrochloride salt of Formula (I). (Pattern VI)
Figure 34:
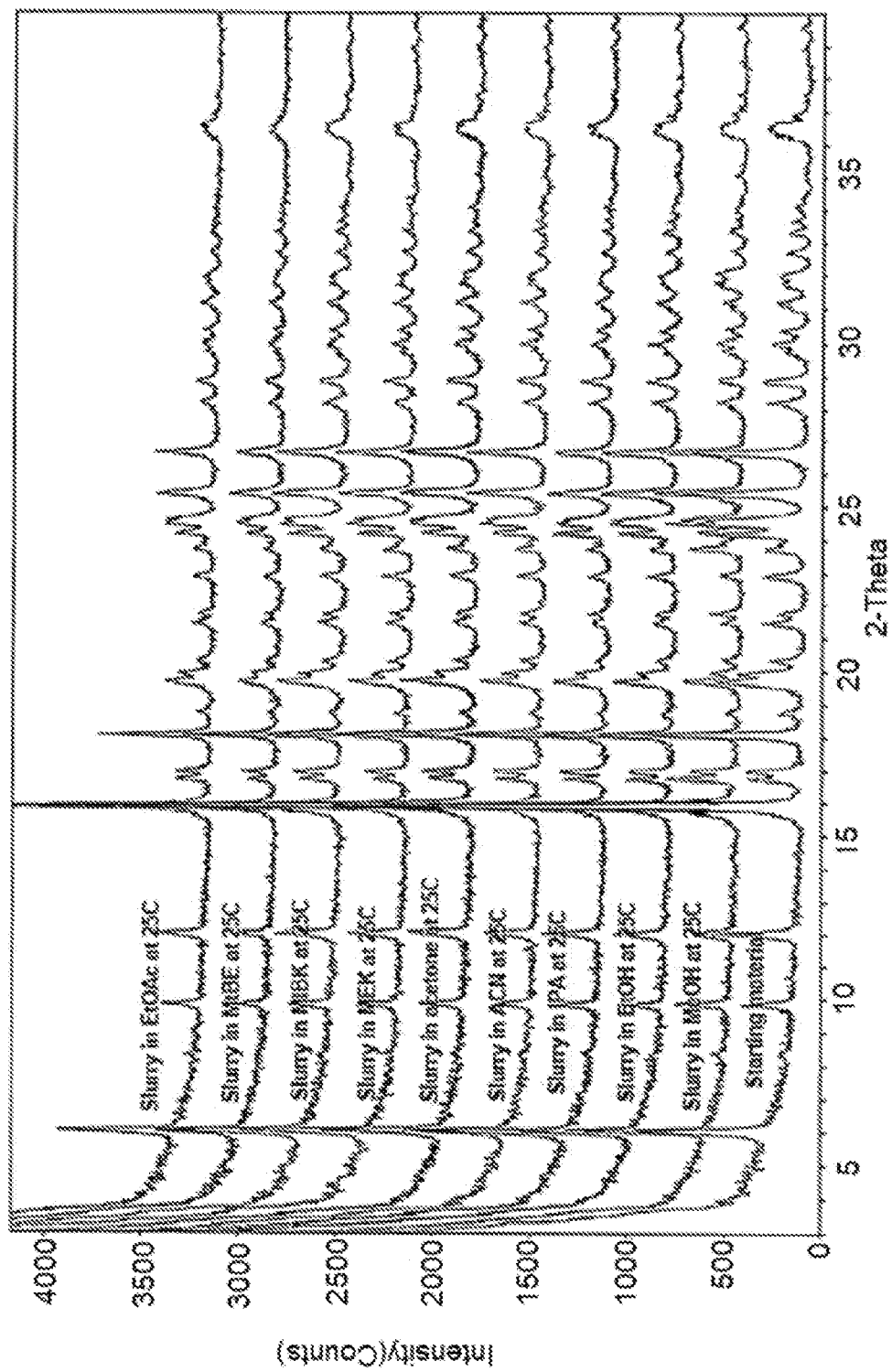
FIG. 34 shows an overlay of XRPD spectra of obtained solids from slurry experiment at 25° C. (Part I).
Figure 35:
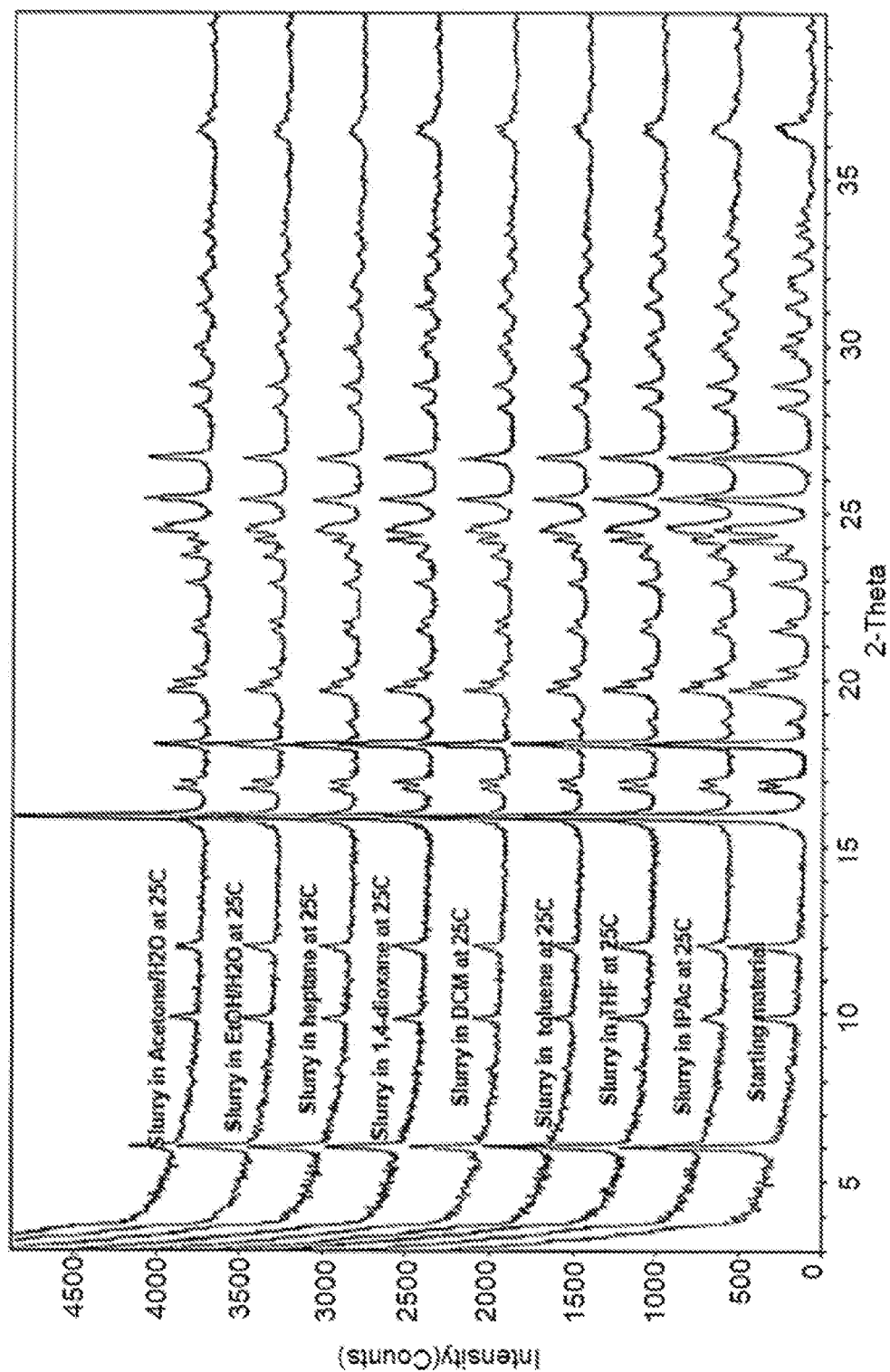
FIG. 35 shows an overlay of XRPD spectra of obtained solids from slurry experiment at 25° C. (Part II).
Figure 36:
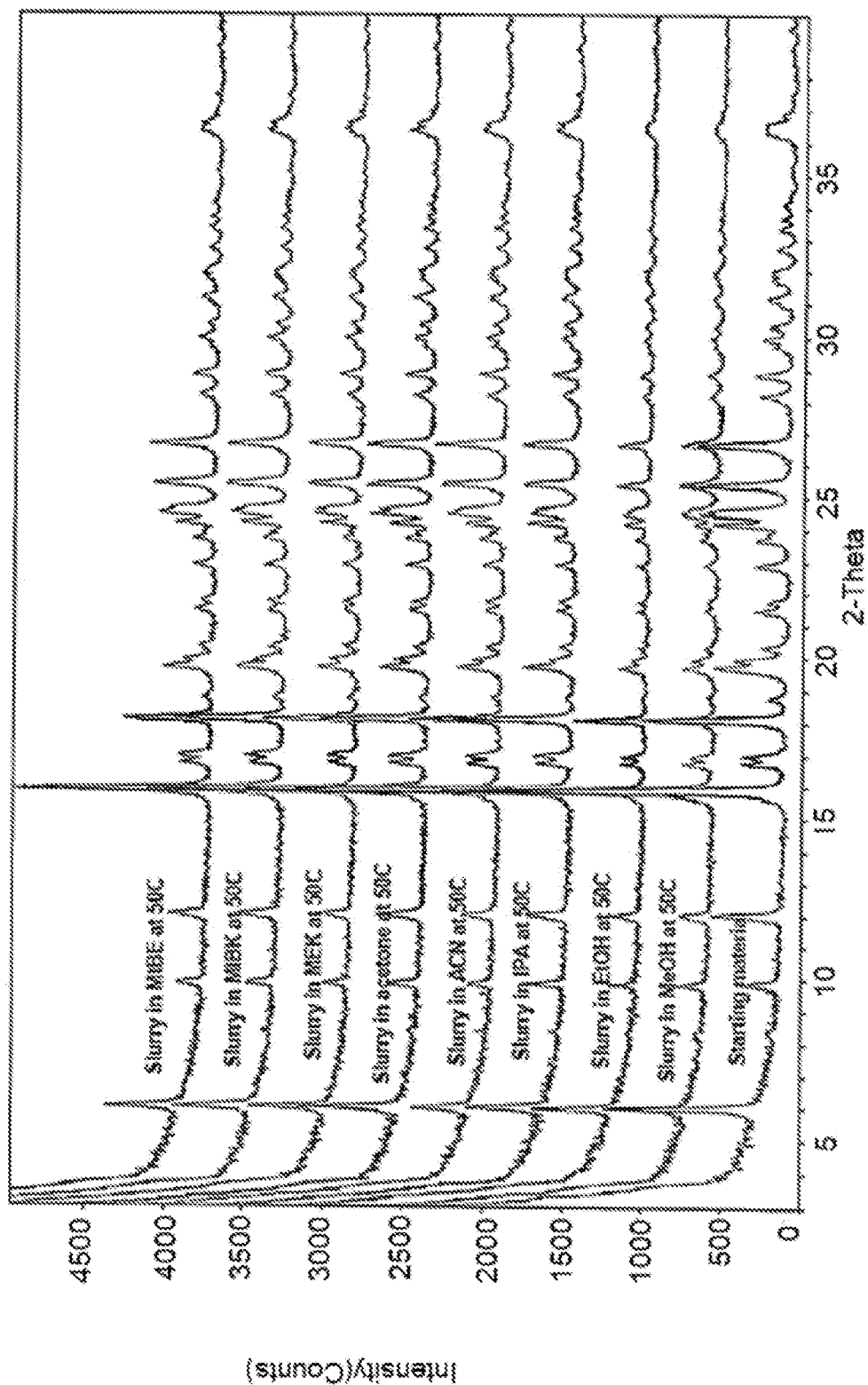
FIG. 36 shows an overlay of XRPD spectra of obtained solids from slurry experiment at 50° C. (Part I).
Figure 37:
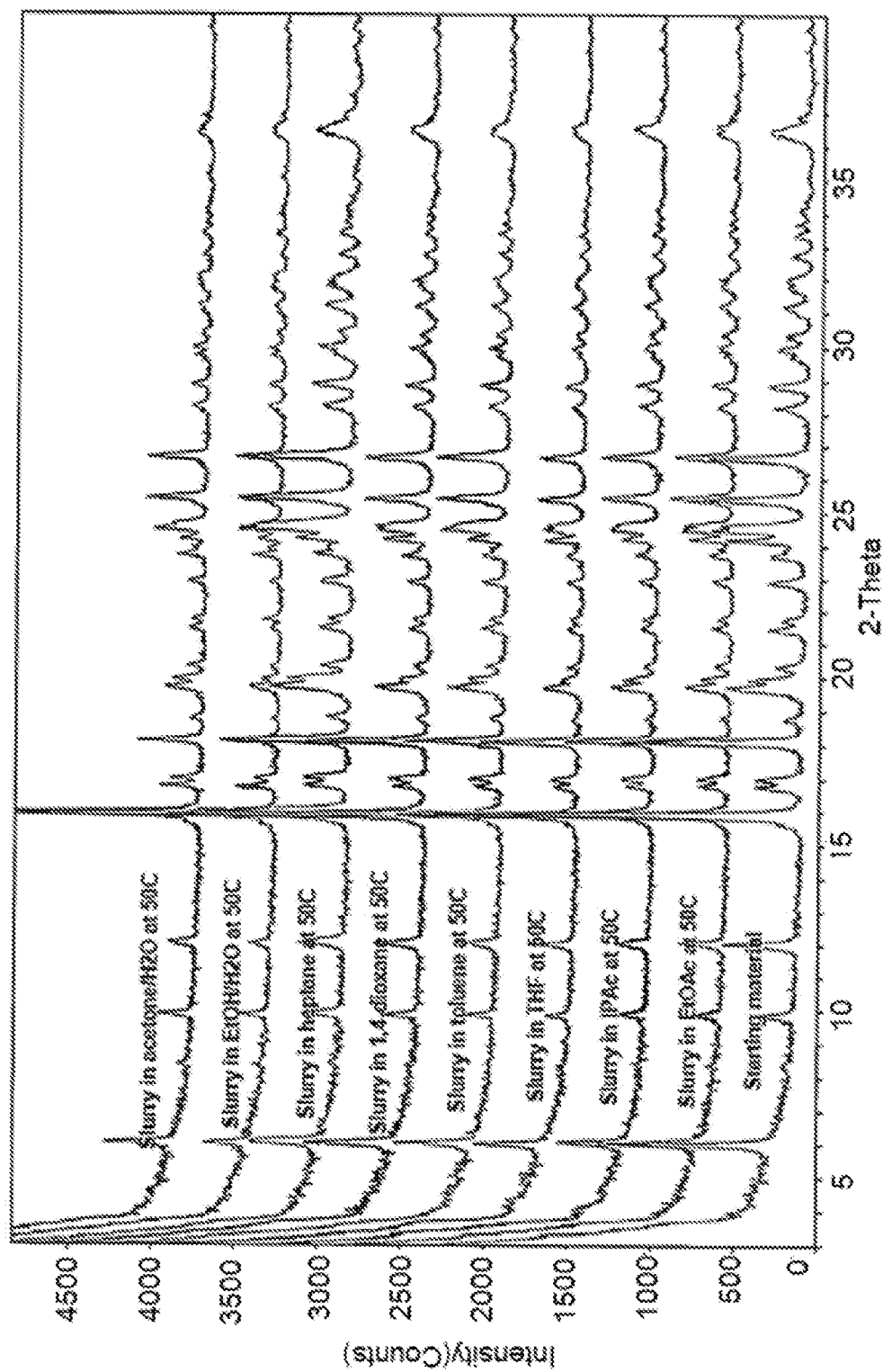
FIG. 37 shows an overlay of XRPD spectra of obtained solids from slurry experiment at 50° C. (Part II).

Physical Characterization (1S,2S)-2-fluoro-N-(6-(4-methylpyridin-3-yl)benzo[d]thiazol-2-yl)cyclopropane-1-carboxamide free base appears as light yellow powder. Subsequently, the physical and thermal properties of free base were characterized. Results were summarized in Table 1 and listed in FIG. 1-3, respectively. Free base of (1S,2S)-2-fluoro-N-(6-(4-methylpyridin-3-yl)benzo[d]thiazol-2-yl)cyclopropane-1-carboxamide displayed birefringence and cubic-like shape according to the polarized light microscope photo (FIG. 1). Meanwhile, according to XRPD result (FIG. 2), starting free base showed high degree of crystallinity. DSC scan (FIG. 3) showed a single endotherm at the onset of 265.94° C. Meanwhile, TGA scan showed ~1.07% weight loss from 23.5° C. to 240.0° C. This free base form was named as Pattern A.

TABLE 1

Physical characterization results of (1S,2S)-2-fluoro-N-(6-(4-methylpyridin-3-yl)benzo[d]thiazol-2-yl)cyclopropane-1-carboxamide free base

| | Compound Name (1S,2S)-2-fluoro-N-(6-(4-methylpyridin-3-yl)benzo[d]thiazol-2-yl)cyclopropane-1-carboxamide free base | | |
|---|---|---|---|
| | No. | 2-Theta (2θ) | Intensity |
| Crystallinity (XRPD) | 1 | 9.8° | 1258 |
| | 2 | 11.6° | 1056 |
| | 3 | 11.9° | 749 |
| | 4 | 13.2° | 1283 |
| | 5 | 14.0° | 1693 |
| | 6 | 14.4° | 557 |
| | 7 | 15.2° | 627 |
| | 8 | 15.7° | 684 |
| | 9 | 16.7° | 853 |
| | 10 | 17.6° | 1258 |
| | 11 | 18.6° | 203 |
| | 12 | 19.1° | 505 |
| | 13 | 19.7° | 376 |
| | 14 | 20.0° | 819 |

TABLE 1-continued

Physical characterization results of (1S,2S)-2-fluoro-N-(6-(4-methylpyridin-3-yl)benzo[d]thiazol-2-yl)cyclopropane-1-carboxamide free base

| | | |
|---|---|---|
| 15 | 20.6° | 2659 |
| 16 | 21.1° | 1601 |
| 17 | 22.9° | 1346 |
| 18 | 23.6° | 353 |
| 19 | 24.9° | 454 |
| 20 | 25.3° | 523 |
| 21 | 26.2° | 900 |
| 22 | 26.4° | 590 |
| 23 | 26.9° | 330 |
| 24 | 28.2° | 181 |
| 25 | 29.3° | 549 |
| 26 | 29.8° | 175 |
| 27 | 30.7° | 572 |
| 28 | 31.6° | 559 |
| 29 | 32.2° | 263 |
| 30 | 32.6° | 133 |
| 31 | 33.3° | 194 |
| 32 | 33.8° | 204 |
| 33 | 34.2° | 203 |
| 34 | 34.7° | 156 |
| 35 | 35.9° | 222 |
| 36 | 36.3° | 166 |
| 37 | 36.7° | 169 |
| 38 | 37.9° | 175 |

| | |
|---|---|
| Particle shape & Size (PLM, μm) | Cubic, ~10 μm |
| Melting Point (DSC, ° C.) | Onset: 265.94° C.; Peak: 267.73° C. |
| Enthalpy (DSC, J/g) | 95.33 J/g |
| Weight loss (TGA, %) | 1.07% (<240° C.) |
| DVS (ΔW %, 80% RH) | 2.30% |
| Form change (Yes/No, XRPD) | (No) |
| Hygroscopicity (DVS) | Hygroscopic |

Solubility Test of Free Base in Solvents

About 4 mg of (1S,2S)-2-fluoro-N-(6-(4-methylpyridin-3-yl)benzo[d]thiazol-2-yl)cyclopropane-1-carboxamide was weighed into a 2.0 mL glass vial and then selected solvents was added in the vial stepwise until all the solid was dissolved. The experiment was conducted by manual dilution combined with visual observation at 25° C. and 50° C. The total volume of solvent added was recorded.

The results are listed in Table 2. (1S,2S)-2-fluoro-N-(6-(4-methylpyridin-3-yl)benzo[d]thiazol-2-yl)cyclopropane-1-carboxamide showed relatively low solubility in mostly common use solvents and showed relatively high solubility in DMF and DMSO.

TABLE 2

Solubility results of free base at 25° C. and 50° C. in solvents

| | Solubility (mg/mL) | |
|---|---|---|
| Solvent | 25° C. | 50° C. |
| Methanol (MeOH) | S < 5 | 5 < S < 7 |
| Ethyl alcohol (EtOH) | S < 5 | S < 5 |
| 2-Propanol (IPA) | S < 5 | S < 5 |
| Acetonitrile (ACN) | S < 5 | S < 5 |
| Acetone | S < 5 | S < 5 |
| Methyl ethyl ketone (MEK) | S < 5 | S < 5 |
| Methyl isobutyl ketone (MIBK) | S < 5 | S < 5 |
| Ethyl acetate (EtOAc) | S < 5 | S < 5 |
| Isopropyl acetate (IPAc) | S < 5 | S < 5 |
| Tetrahydrofuran (THF) | 8 < S < 10 | 9 < S < 13 |
| Methyl tert-butyl ether (MtBE) | S < 5 | S < 5 |
| Toluene | S < 5 | S < 5 |
| Dichloromethane (DCM) | S < 5 | N/A* |
| N,N-Dimethylformamide (DMF) | 67 < S < 100 | S > 100 |

TABLE 2-continued

Solubility results of free base at 25° C. and 50° C. in solvents

| | Solubility (mg/mL) | |
|---|---|---|
| Solvent | 25° C. | 50° C. |
| Dimethylsulfoxide (DMSO) | S > 100 | — |
| 1,4-dioxane | S < 5 | 7 < S < 10 |
| Heptane | S < 5 | S < 5 |
| Water | S < 5 | S < 5 |
| EtOH/H$_2$O (1/1, v/v) | S < 5 | S < 5 |
| Acetone/H$_2$O (1/1, v/v) | S < 5 | S < 5 |

*The solubility in DCM at 50° C. was not measured because of the low boiling point of solvent.

Solubility Test of Free Base in Bio-Relevant Media and Buffers

About 5 mg starting free base were weighed in 2 mL vials. Then 1.0 mL biorelevant media (SGF, FaSSIF and FeSSIF) and buffers were added into the vials. All the vials were placed on the thermo-mixer and kept at 37° C. (700 r/m in). After shaking at 37° C. for 24 hrs, mother liquids obtained by filtration were analyzed by HPLC directly or after being diluted by ACN/water for 20-40 times. Solubility results were summarized in Table 3. According to the solubility results, freebase showed medium solubility (2.0-2.5 mg/mL) in SGF and pH 2.0 buffer.

TABLE 3

Solubility results of free base in bio-relevant media and buffers

| Bio-relevant media/ Buffers | Initial pH value | Final pH value | Solubility (µg/mL) |
|---|---|---|---|
| SGF | 1.92 | 2.28 | 2490 |
| FaSSIF | 6.52 | 6.50 | N.D. |
| FeSSIF | 5.07 | 5.09 | 45 |
| pH 2.0 buffer | 1.98 | 2.25 | 2060 |
| pH 4.0 buffer | 4.01 | 4.05 | 31 |
| pH 6.0 buffer | 5.90 | 5.88 | 2 |
| pH 8.0 buffer | 8.04 | 8.08 | N.D. |
| water | — | 8.84 | N.D. |

Example 2. Preliminary Salt Screening Experiments

Based on calculated pKa values for (1S,2S)-2-fluoro-N-(6-(4-methylpyridin-3-yl)benzo[d]thiazol-2-yl)cyclopropane-1-carboxamide free base of 5.53, −0.74 and −8.39, ten acids were selected as counterions for salt screening study initially. Meanwhile, acetone, EtOAc, ACN and IPA/water (95/5, v/v) were selected as salt screening solvents. Details of salt screening procedure were listed as below.

For solid counter-ions, 50 mg (1S,2S)-2-fluoro-N-(6-(4-methylpyridin-3-yl)benzo[d]thiazol-2-yl)cyclopropane-1-carboxamide free base and 1.1 e.q. counter ions were weighted into 2 mL vials individually, and then 1.0 mL solvents were added into the vials. For liquid counter-ions, 50 mg (1S,2S)-2-fluoro-N-(6-(4-methylpyridin-3-yl)benzo[d]thiazol-2-yl)cyclopropane-1-carboxamide free base were weighted into 2 mL vials, and 850 µL solvents were added in the vials subsequently. Then 1.1 e.q. counter-ions solutions of corresponding solvents (concentration: 0.1 g/mL) were added to the vials. At the same time, (1S,2S)-2-fluoro-N-(6-(4-methylpyridin-3-yl)benzo[d]thiazol-2-yl)cyclopropane-1-carboxamide free base slurried in 1.0 mL same solvents were used as control. All the vials were placed on the thermo-mixer and heated to 50° C. After keeping at 50° C. for 14 hrs, the vials were then cooled to 25° C. in 2 hrs. After keeping at 25° C. for 5 hrs, the solids in suspensions were isolated by centrifugation and dried in the vacuum oven at 30° C. for 3 days. Obtained dried solids were then characterized by XRPD. The salt screening results are listed in Table 4 and FIGS. 4 to 14.

The XRPD pattern of starting free base was named as Pattern A in this study initially. Totally 5 new XRPD patterns were found in salt formation experiments with five different counter-ions, including hydrochloric acid (Pattern I), sulfuric acid (Pattern II), maleic acid (Pattern III), fumaric acid (Pattern IV) and methane sulfonic acid (Pattern V). Amorphous solids were obtained after salt formation with phosphoric acid, which also indicated the formation of potential salt.

TABLE 4

Summary of XRPD results of salt screening experiments

| | Acetone | EtOAc | ACN | IPA/H$_2$O (95v/5v) |
|---|---|---|---|---|
| Hydrochloric acid | Pattern I | Pattern I | Pattern I | Pattern I |
| Sulfuric acid | Pattern II (LC) | Pattern II (LC) | Pattern II (LC) | Pattern II |
| L-Aspartic acid | Pattern A + acid | Pattern A + acid | Pattern A + acid | Pattern A |
| Maleic acid | Pattern III | Pattern III | Pattern III | Pattern III |
| Phosphoric acid | Amorphous | Amorphous | Amorphous | Amorphous + few Pattern A |
| L(+)-Tartaric acid | Pattern A | Pattern A | Amorphous + Pattern A | Pattern A |
| Fumaric acid | Pattern IV | Pattern IV | Pattern IV | Pattern A |
| Citric acid. H$_2$O | Pattern A | Pattern A | Amorphous + Pattern A | Pattern A |
| L-Malic acid | Pattern A | Pattern A | Pattern A | Pattern A |
| Methane sulfonic acid | Pattern V (LC) | Pattern V (LC) | Pattern V (LC) | Pattern V |

Roman numbers means the different XRPD patterns of the salt.
A means the XRPD pattern of free form.
LC means an abbreviation for low crystallinity The 5 new salt forms were further characterized by XRPD, DSC and TGA, especially, organic salts were also characterized by $^1$H-NMR to confirm the formation of the salts and the stoichiometry of acid/base ratios. The characterization results are listed in Table 5 and FIGS. 15 to 27

According to the characterization results, obtained sulfate showed low crystallinity and bad thermal properties.

2. Hold at 50° C. for 1 hr; (Suspension);
3. Add 1.1 e.q. hydrochloride acid of acetone solution (6.72 mL, 0.5 mmol/mL) into the suspension dropwise. (Suspension)
4. Hold at 50° C. for 3 hrs; (Suspension);
5. Cool to 25° C. and hold at 25° C. for 17 hrs; (Suspension);

TABLE 5

Summary of physical characterization of 5 new XRPD pattern salts

| | Hydrochloride Pattern 1 | | Sulfate Pattern II | | Maleate Pattern III | | Fumarate Pattern IV | | Mesylate Pattern V | |
|---|---|---|---|---|---|---|---|---|---|---|
| | 2θ | Intensity | 2θ | Intensity | 2θ | Intensity | 2θ | Intensity | 2θ | Intensity |
| XRPD | 6.0° | 646 | 8.7° | 466 | 7.7° | 437 | 5.3° | 1370 | 5.1° | 664 |
| | 9.8° | 307 | 10.9° | 245 | 9.4° | 877 | 9.9° | 623 | 8.3° | 271 |
| | 12.0° | 321 | 12.3° | 190 | 10.1° | 893 | 10.6° | 944 | 8.6° | 234 |
| | 15.9° | 1793 | 12.6° | 165 | 12.1° | 240 | 12.1° | 305 | 9.0° | 204 |
| | 16.8° | 309 | 12.9° | 242 | 14.8° | 1808 | 13.2° | 561 | 10.2° | 387 |
| | 17.0° | 298 | 14.1° | 198 | 15.3° | 827 | 13.5° | 351 | 12.7° | 186 |
| | 18.1° | 589 | 15.4° | 252 | 18.0° | 2623 | 14.9° | 534 | 14.7° | 205 |
| | 18.8° | 178 | 15.7° | 165 | 19.2° | 273 | 16.0° | 615 | 15.2° | 582 |
| | 19.7° | 466 | 16.2° | 219 | 19.6° | 179 | 17.2° | 1401 | 16.2° | 234 |
| | 19.9° | 370 | 16.4° | 260 | 20.3° | 194 | 17.6° | 354 | 16.6° | 284 |
| | 20.3° | 235 | 16.8° | 239 | 20.7° | 339 | 18.0° | 377 | 18.6° | 429 |
| | 21.5° | 226 | 17.6° | 307 | 21.3° | 229 | 19.8° | 592 | 20.5° | 406 |
| | 21.8° | 196 | 17.9° | 207 | 22.4° | 568 | 20.8° | 154 | 21.9° | 314 |
| | 22.9° | 243 | 18.6° | 173 | 22.6° | 606 | 21.3° | 403 | 22.8° | 227 |
| | 23.7° | 282 | 18.9° | 296 | 23.0° | 1362 | 21.9° | 314 | 25.0° | 276 |
| | 24.3° | 328 | 19.9° | 338 | 23.3° | 621 | 22.8° | 434 | 29.0° | 149 |
| | 24.6° | 576 | 20.3° | 567 | 24.0° | 169 | 23.2° | 271 | 30.1° | 138 |
| | 25.4° | 593 | 20.7° | 204 | 24.3° | 287 | 25.2° | 228 | | |
| | 26.7° | 542 | 21.3° | 189 | 24.7° | 275 | 25.9° | 393 | | |
| | 28.2° | 217 | 21.7° | 258 | 24.9° | 248 | 26.5° | 1399 | | |
| | 28.9° | 257 | 22.1° | 281 | 25.4° | 940 | 27.7° | 393 | | |
| | 29.7° | 169 | 22.7° | 274 | 26.2° | 400 | 29.9° | 212 | | |
| | 30.0° | 243 | 24.9° | 446 | 27.6° | 421 | 30.5° | 166 | | |
| | 30.4° | 137 | 25.4° | 205 | 29.2° | 962 | 32.2° | 142 | | |
| | 31.2° | 193 | 25.9° | 156 | 30.2° | 171 | 34.4° | 177 | | |
| | 32.1° | 195 | 26.2° | 146 | 30.8° | 304 | 34.8° | 149 | | |
| | 32.8° | 141 | 27.3° | 162 | 31.2° | 183 | 36.9° | 132 | | |
| | 33.3° | 160 | 28.5° | 175 | 31.7° | 128 | | | | |
| | 33.7° | 131 | 28.8° | 140 | 32.3° | 163 | | | | |
| | 34.2° | 119 | 30.3° | 116 | 33.0° | 253 | | | | |
| | 35.1° | 101 | 32.9° | 112 | 33.9° | 126 | | | | |
| | 36.4° | 265 | | | 35.7° | 159 | | | | |
| | | | | | 36.9° | 158 | | | | |
| | | | | | 37.6° | 112 | | | | |
| | | | | | 38.6° | 113 | | | | |
| | | | | | 38.9° | 151 | | | | |
| Melting point (DSC, ° C.) | 240.11° C. | | 1$^{st}$: 212.49° C.; 2$^{nd}$: 228.77° C.; | | 174.32° C. | | 226.58° C. | | 193.77° C. | |
| Enthalpy (DSC, J/g) | 57.84 J/g | | 1$^{st}$: 12.31 J/g; 2$^{nd}$: 11.76 J/g; | | 107.9 J/g | | 179.4 J/g | | 49.92 J/g | |
| Weight loss (TGA, %) | 0.44% (<150° C.); 10.42% (150-225° C.); | | 1.50% (<100° C.); 0.45% (100-175° C.); 2.45% (175-235° C.); | | 0.64% (<150° C.); | | 0.82% (<185° C.) | | 1.83% (<100° C.); 0.37% (100-205° C.); | |
| Counter-ion/ API ratio ($^1$H-NMR) | 240.11° C. | | 1$^{st}$: 212.49° C.; 2$^{nd}$: 228.77° C.; | | 174.32° C. | | 226.58° C. | | 193.77° C. | |

Example 3. Comparative Test of Mono-Hydrochloride and Di-Hydrochloride Salt

To investigate the influence of ratio of hydrochloric acid to compound on the salt formation process, salt formation experiments with different acid ratio (1.1 e.q. and 2.2 e.q.) were carried out. The details of operation procedures were described as below:

1) Procedures of mono-hydrochloride salt formation experiment comprising the steps of:
 1. Suspend 1.00 g (1S,2S)-2-fluoro-N-(6-(4-methylpyridin-3-yl)benzo[d]thiazol-2-yl)cyclopropane-1-carboxamide free base into 15.0 mL acetone at 50° C.;

6. Measure XRPD of wet solids;
7. Continue to slurry at 25° C. for 5 hrs;
8. Filter the suspension by funnel and wash the wet cake by 3.0 mL solvent;
9. Dry wet cake in the vacuum at 35° C. for 16 hrs;
10. Total 1.00 g dry solids were obtained.

2) Procedures of di-hydrochloride salt formation experiment comprising the steps of:
 1. Suspend 1.00 g API into 15.0 mL acetone at 50° C.;
 2. Hold at 50° C. for 1 hr; (Suspension);
 3. Add 2.2 e.q. hydrochloride acid of acetone solution (6.72 mL, 1.0 mmol/mL) into the suspension dropwise.

The system was frozen and the slurry was not very good. Add another 5.0 mL acetone into the system (Suspension);
4. Hold at 50° C. for 3 hrs; (Suspension);
5. Cool to 25° C. and hold at 25° C. for 17 hrs; (Suspension);
6. Measure XRPD of wet solids;
7. Continue to slurry at 25° C. for 5 hrs;
8. Filter the suspension by funnel and wash the wet cake by 3.0 mL solvent;
9. Dry wet cake in the vacuum at 35° C. for 16 hrs;
10. Total 1.13 g dry solids were obtained.

The comparison results between mono-hydrochloride and di-hydrochloride salt forms are listed in Table 6 and characterized by $^1$H-NMR, XRPD, DSC and TGA as shown in FIGS. 28 to 33. According to the XRPD results, di-hydrochloride salt showed low crystallinity as Pattern VI.

TABLE 6

The comparison results in mono-hydrochloride and Di-hydrochloride salt forms

| | Hydrochloride Pattern I | | Di-hydrochloride Pattern VI + Few Pattern I | |
|---|---|---|---|---|
| | 2-Theta (2θ) | Intensity | 2-Theta (2θ) | Intensity |
| XRPD (2θ) | 6.0° | 646 | 6.1° | 323 |
| | 9.8° | 307 | 6.6° | 733 |
| | 12.0° | 321 | 9.7° | 287 |
| | 15.9° | 1793 | 10.0° | 288 |
| | 16.8° | 309 | 12.3° | 174 |
| | 17.0° | 298 | 13.3° | 187 |
| | 18.1° | 589 | 13.9° | 343 |
| | 18.8° | 178 | 15.0° | 212 |
| | 19.7° | 466 | 15.9° | 340 |
| | 19.9° | 370 | 16.8° | 148 |
| | 20.3° | 235 | 18.1° | 159 |
| | 21.5° | 226 | 18.6° | 228 |
| | 21.8° | 196 | 19.2° | 209 |
| | 22.9° | 243 | 19.9° | 231 |
| | 23.7° | 282 | 20.9° | 233 |
| | 24.3° | 328 | 22.0° | 262 |
| | 24.6° | 576 | 22.9° | 181 |
| | 25.4° | 593 | 23.8° | 300 |
| | 26.7° | 542 | 24.6° | 316 |
| | 28.2° | 217 | 25.0° | 309 |
| | 28.9° | 257 | 25.4° | 288 |
| | 29.7° | 169 | 26.5° | 282 |
| | 30.0° | 243 | 26.8° | 377 |
| | 30.4° | 137 | 27.5° | 186 |
| | 31.2° | 193 | 28.8° | 212 |
| | 32.1° | 195 | 29.4° | 179 |
| | 32.8° | 141 | 31.7° | 152 |
| | 33.3° | 160 | 31.9° | 152 |
| | 33.7° | 131 | 33.4° | 136 |
| | 34.2° | 119 | 33.8° | 133 |
| | 35.1° | 101 | 35.4° | 152 |
| | 36.4° | 265 | 36.6° | 130 |
| | | | 37.6° | 120 |
| Melting point (DSC, ° C.) | 238.10° C. | | 167.58° C. | |
| Enthalpy (DSC, J/g) | 38.0 J/g | | 67.23 J/g | |
| Weight loss (TGA, %) | 0.38% (<150° C.); 9.67% (150-225° C.); | | 3.01% (<80° C.); 8.48% (80-175° C.); | |

3) Solubility tests in bio-relevant media

Solubilities of mono-hydrochloride and di-hydrochloride salt forms in biorelevant media were tested at 37° C. Details of procedures were listed as below:

About 15 mg obtained salts were weighed in 2 mL vials, respectively. Then 1.0 mL bio-relevant media (SGF, FaSSIF and FeSSIF) were added into the vials. All the vials were placed on the thermo-mixer and kept at 37° C. (700 r/min). After shaking at 37° C. for 17 hrs, clear solutions obtained by centrifugation were analyzed by HPLC after being diluted by ACN/water (1v/1v) for 10-50 times. And pH value of all systems were measured. The solubility results are summarized in Table 7.

TABLE 7 solubility results in bio-relevant media by HPLC

| | SGF (pH = 1.88) | | FaSSIF (pH = 6.62) | | FeSSIF (pH = 5.07) | |
|---|---|---|---|---|---|---|
| | Solubility (mg/mL) | pH | Solubility (mg/mL) | pH | Solubility (mg/mL) | pH |
| Mono-hydrochloride | >13.93 | 1.89 | 7.84 | 2.01 | 0.13 | 3.83 |
| Di-hydrochloride | >13.26 | 1.39 | 13.07 | 1.75 | 2.22 | 2.51 |

Example 4. Polymorph Screening Study of (1S,2S)-2-fluoro-N-(6-(4-methylpyridin-3-yl)benzo[d]thiazol-2-yl)cyclopropane-1-carboxamide Mono-hydrochloride A polymorph screening study of mono-hydrochloride with Pattern I was performed by slurry method, heating-cooling method, slow evaporation method and anti-solvent method. No new XRPD pattern was found by these methods. Dry grinding and wet milling were carried out to test physical stability of mono-hydrochloride in the milling process. XRPD results showed that the crystallinity of residual solids were decreased after dry grinding, while the crystalline form was not changed after dry grinding or wet granulation process.

One polymorph (pattern I) of mono-hydrochloride was observed in polymorph screening experiment.

1) Slurry Method

About 50 mg of (1S,2S)-2-fluoro-N-(6-(4-methylpyridin-3-yl)benzo[d]thiazol-2-yl)cyclopropane-1-carboxamide mono-hydrochloride was suspended into 1.0 mL selected pure or binary solvents in 2.0 mL glass vials. The suspensions were placed on the thermo-mixer with the speed of 700 r/m in at 25° C. and 50° C. After 4 days, slurries and suspensions were centrifuged (8,000 r/m in, 5 mins) and residual solids were dried in the vacuum oven at 35° C. for 4 hrs. Then obtained dried solids were characterized by XRPD and the results are summarized in Table 8.

As shown by the XRPD results of obtained solids after slurried at 25° C. and 50° C. for 4 days in FIGS. 34 to 37, all solids were still Pattern I and no new XRPD patterns were found.

TABLE 8

Results of slurry experiments at 25° C. and 50° C.

| | | XRPD results | |
|---|---|---|---|
| No. | Solvents | 25° C. | 50° C. |
| 1 | MeOH | Pattern I | Pattern I |
| 2 | EtOH | Pattern I | Pattern I |
| 3 | IPA | Pattern I | Pattern I |
| 4 | ACN | Pattern I | Pattern I |
| 5 | Acetone | Pattern I | Pattern I |
| 6 | MEK | Pattern I | Pattern I |
| 7 | MIBK | Pattern I | Pattern I |
| 8 | MtBE | Pattern I | Pattern I |

TABLE 8-continued

Results of slurry experiments at 25° C. and 50° C.

| | | XRPD results | |
|---|---|---|---|
| No. | Solvents | 25° C. | 50° C. |
| 9 | EtOAc | Pattern I | Pattern I |
| 10 | IPAc | Pattern I | Pattern I |
| 11 | THF | Pattern I | Pattern I |
| 12 | Toluene | Pattern I | Pattern I |
| 13 | DCM | Pattern I | N/A |
| 14 | 1,4-Dioxane | Pattern I | Pattern I |
| 15 | Heptane | Pattern I | Pattern I |
| 16 | EtOH/H$_2$O(95/5, v/v) | Pattern I | Pattern I |
| 17 | Acetone/H$_2$O(95/5, v/v) | Pattern I | Pattern I |

Heating-Cooling Method

Figure 38:
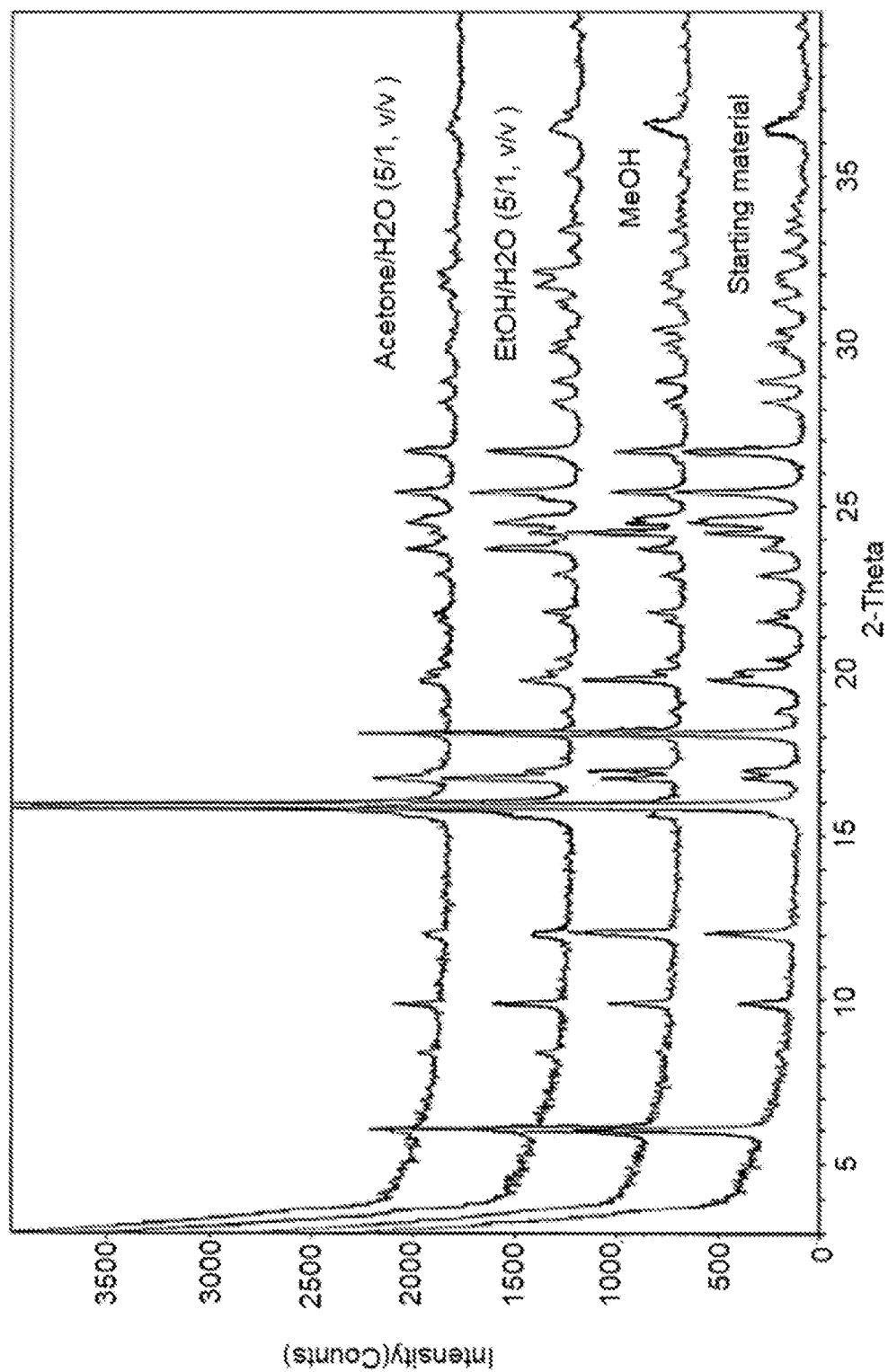
FIG. 38 shows an overlay of XRPD spectra of obtained solids from heating-cooling experiment.

About 50 mg of (1S,2S)-2-fluoro-N-(6-(4-methylpyridin-3-yl)benzo[d]thiazol-2-yl)cyclopropane-1-carboxamide mono-hydrochloride was suspended into 1.0 mL selected pure or binary solvents in 2.0 mL glass vials at 50° C. stirring with the speed of 500 r/min. Then the suspensions were filtered through 0.45 μm filters into clean 2.0 mL glass vials and placed on the hot-plate stirring with 500 r/m in at 50° C. After stirring at 50° C. for 1.5 hrs, the system was cooled to 25° C. After stirring at 25° C. for 16 hrs, some solids came out from MeOH, EtOH/H$_2$O (5/1, v/v) and acetone/H$_2$O (5/1, v/v) systems, while very few solids came out from EtOH system. Then MeOH, EtOH/H$_2$O (5/1, v/v) and acetone/H$_2$O (5/1, v/v) systems were centrifuged at 10000 r/min for 5 mins and residual solids were dried in the vacuum oven at 35° C. for 3 hrs. Obtained dry solids were then characterized by XRPD. The analysis results are summarized in Table 8 and FIG. 38. All resulted solids were Pattern I and no new XRPD patterns were obtained by heating-cooling method.

TABLE 9

Results of crystallization by heating-cooling method

| Solvent | Observations | XRPD results |
|---|---|---|
| MeOH | Some solids came out | Pattern I |
| EtOH | Few solids came out | N/A* |
| EtOH/H$_2$O(5/1, v/v) | Some solids came out | Pattern I |
| Acetone/H$_2$O(5/1, v/v) | Some solids came out | Pattern I |

*Obtained solids were too few to do XRPD test.

Slow Evaporation Method

Figure 39:
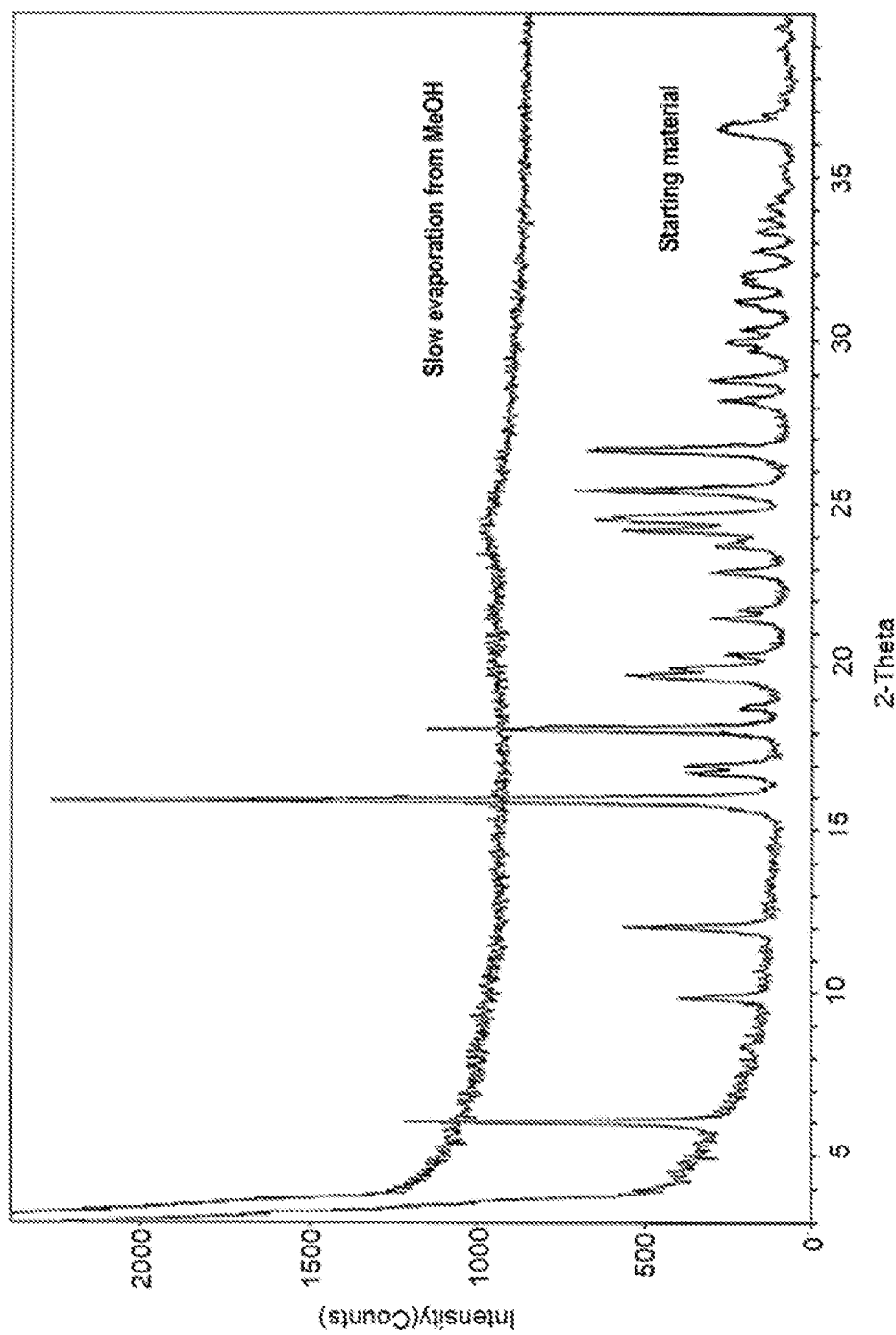
FIG. 39 shows an overlay of XRPD spectra of obtained solids from slow evaporation experiment.

About 30 mg of (1S,2S)-2-fluoro-N-(6-(4-methylpyridin-3-yl)benzo[d]thiazol-2-yl)cyclopropane-1-carboxamide mono-hydrochloride was weighted in 2.0 mL glass vials and then 1.5 mL MeOH was added. Then the solution was filtered into clean 4.0 mL glass vial through 0.45 μm filter. The vial was covered with aluminum film with pinhole and placed in the fumehood. After 4 days, evaporation, the obtained solids were dried in the vacuum oven at 35° C. for 4 hrs and then characterized by XRPD. As shown by the XRPD results of obtained solids in FIG. 39, amorphous solid was obtained from MeOH system by evaporation method.

Anti-Solvent Method

Based on the solubility results of (1S,2S)-2-fluoro-N-(6-(4-methylpyridin-3-yl)benzo[d]thiazol-2-yl)cyclopropane-1-carboxamide mono-hydrochloride, MeOH, DMF, DMSO, and water were selected as good solvents to dissolve the compound because the (1S,2S)-2-fluoro-N-(6-(4-methylpyridin-3-yl)benzo[d]thiazol-2-yl)cyclopropane-1-carboxamide mono-hydrochloride showed relatively high solubility in these solvents, while MtBE, IPA and acetone were selected as anti-solvents.

Figure 40:
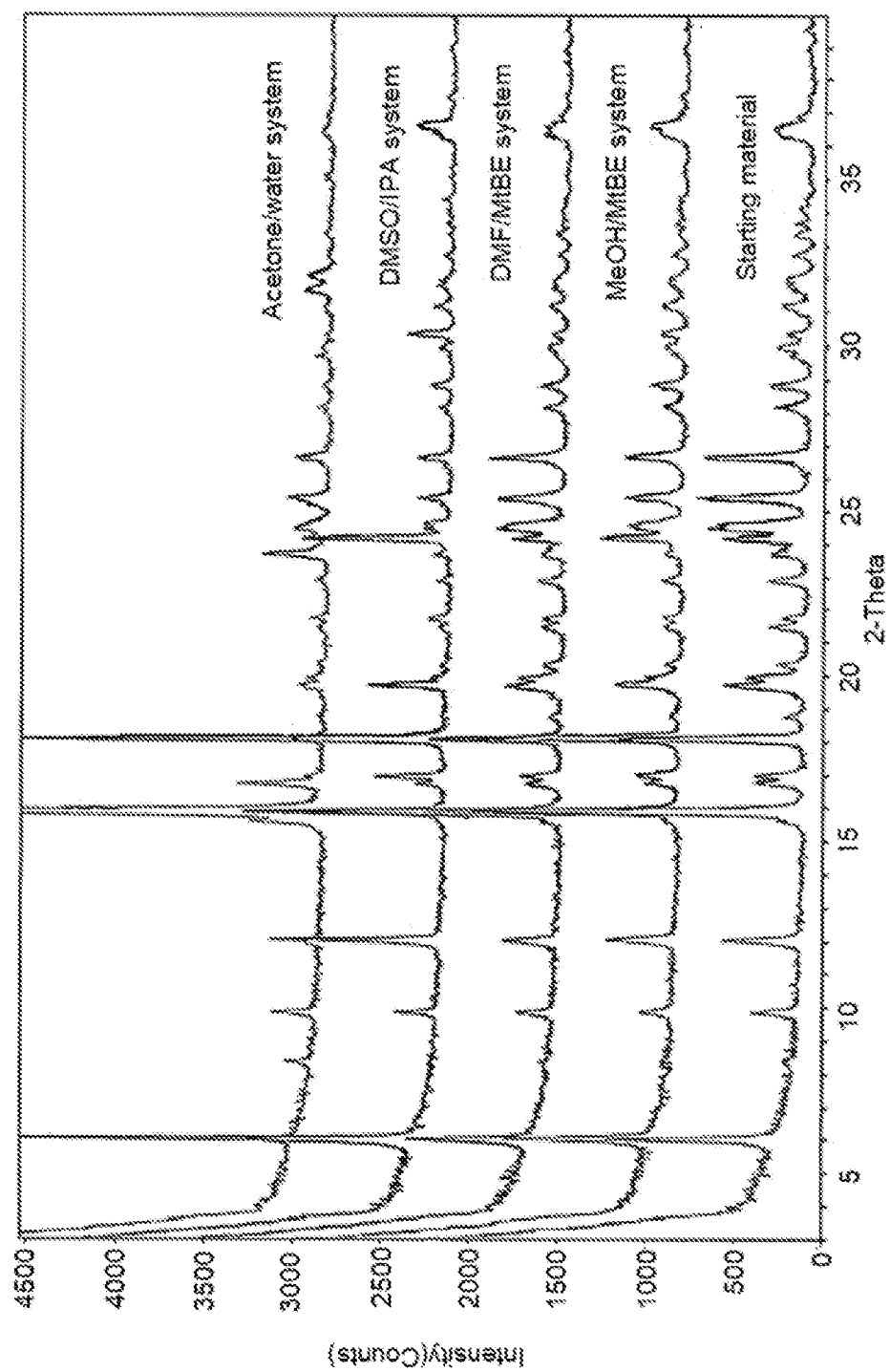
FIG. 40 shows an overlay of XRPD spectra of obtained solids from anti-solvent experiment.

About 50 mg of (1S,2S)-2-fluoro-N-(6-(4-methylpyridin-3-yl)benzo[d]thiazol-2-yl)cyclopropane-1-carboxamide mono-hydrochloride was weighted in 8.0 mL glass vials and then 0.5-2.0 mL selected good solvents were added. All the vials were placed on the hot-plate and stirred with the speed of 500 r/m in at 50° C. After stirring at 50° C. for 30 min, all the systems were clear. Then selected anti-solvents were added stepwise until solids came out or the volume ratio of anti-solvent/good solvent reached 10:1. All the systems were holding at 50° C. for 1 hr, and then cooled to 25° C. After holding at 25° C. for 16 hrs or 3 days, the suspensions were centrifuged. Wet solids were then dried in the vacuum oven and the resulted dry solids were further characterized by XRPD. The results are summarized in Table 10 and FIG. 40. All resulted solids were Pattern I and no new XRPD pattern was found by anti-solvent method.

TABLE 10

Results of crystallization by anti-solvent experiment

| Good solvent | Anti-solvent | Anti-solvent/good solvent ratio (v/v) | Observations | XRPD results |
|---|---|---|---|---|
| THF | MtBE | 2/1 | Solids came out at 50° C. | Pattern I |
| DMF | MtBE | 2/1 | Solids came out at 50° C. | Pattern I |
| DMSO | IPA | 5/1 | Solids came out at 50° C. | Pattern I |
| Water | Acetone | 10/1 | Solids came out at 50° C. | Pattern I |

Grinding Method

Dry grinding and wet granulation were carried out to test physical stability of (1S,2S)-2-fluoro-N-(6-(4-methylpyridin-3-yl)benzo[d]thiazol-2-yl)cyclopropane-1-carboxamide mono-hydrochloride in the milling process.

For dry grinding experiment, about 50 mg of (1S,2S)-2-fluoro-N-(6-(4-methylpyridin-3-yl)benzo[d]thiazol-2-yl)cyclopropane-1-carboxamide mono-hydrochloride was added into mortar and grinded by pestle for about 5 mins. Residual solids were then characterized by XRPD.

For wet granulation experiment, about 50 mg of (1S,2S)-2-fluoro-N-(6-(4-methylpyridin-3-yl)benzo[d]thiazol-2-yl) cyclopropane-1-carboxamide mono-hydrochloride was added into mortar and then several drops of solvent EtOH were added until the solids were fully wetted. Wet solids were grinded by pestle for about 5 mins manually and residual solids were then characterized by XRPD.

Figure 41:
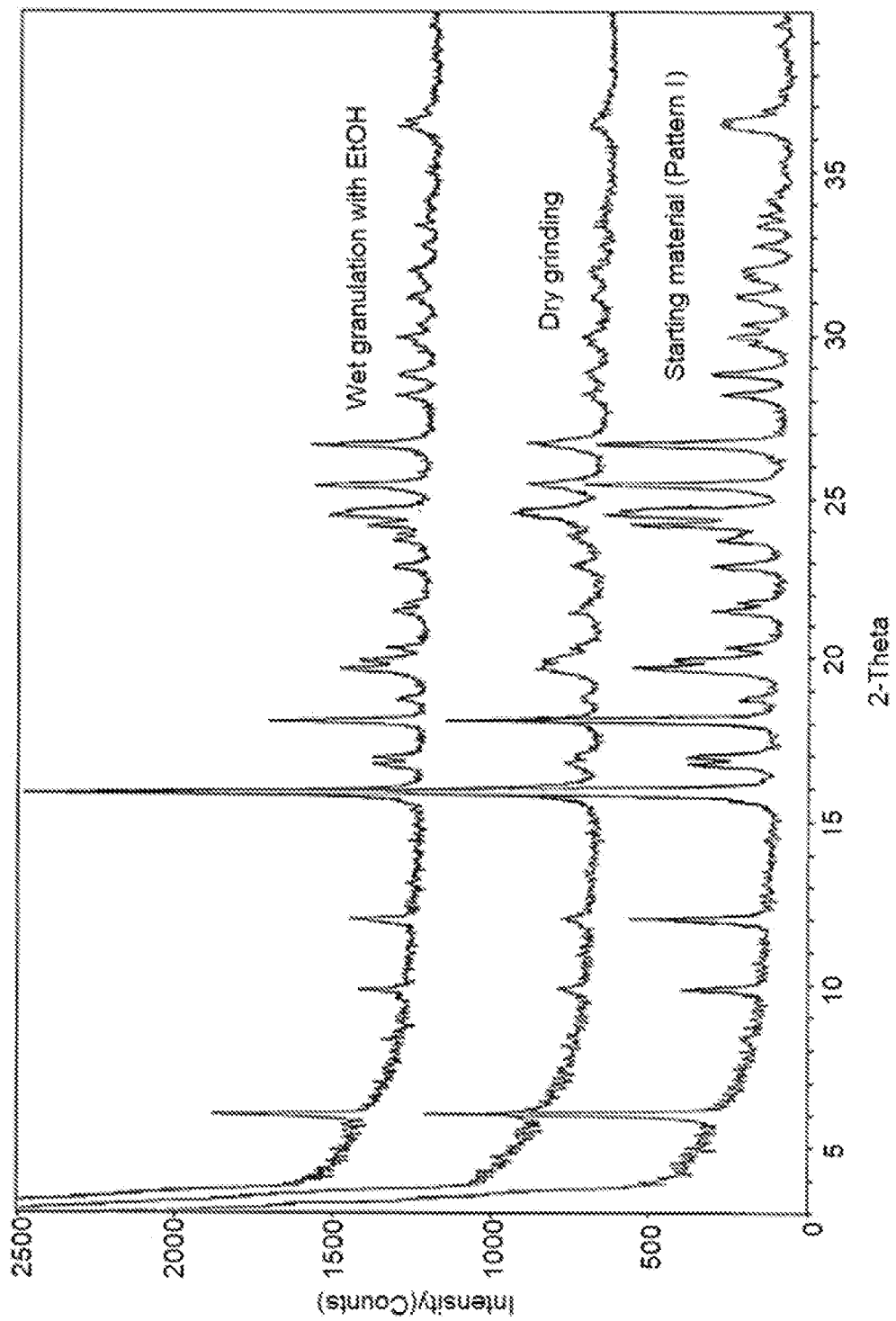
FIG. 41 shows an overlay of XRPD spectra of obtained solids from dry or wet grinding.

As shown by the XRPD results of obtained solids after grinding in FIG. 41, the crystallinity of residual solids were decreased after dry grinding, while the crystalline form was not changed after dry grinding and wet grinding process.

What is claimed is:

1. A crystalline form of (1S,2S)-2-fluoro-N-(6-(4-methylpyridin-3-yl)benzo[d]thiazol-2-yl) cyclopropane-1-carboxamide or a pharmaceutically acceptable salt thereof,
wherein the crystalline form is selected from the group consisting of:
a crystalline form having peaks at diffraction angle (2θ) of 9.8±0.2, 11.6±0.2, 13.2±0.2, 14.0±0.2, 16.7±0.2, 17.6±0.2, 20.6±0.2, 22.9±0.2, 26.2±0.2, 29.3±0.2, 30.7±0.2, 31.6±0.2;
a crystalline form having peaks at diffraction angle (2θ) of 6.0±0.2, 15.9±0.2, 18.1±0.2, 19.7±0.2, 24.6±0.2, 25.4±0.2, 26.7±0.2;

a crystalline form having peaks at diffraction angle (2θ) of 8.7±0.2, 10.9±0.2, 12.9±0.2, 15.4±0.2, 16.4±0.2, 18.9±0.2, 20.3±0.2, 22.1±0.2, 22.7±0.2, 24.9±0.2;

a crystalline form having peaks at diffraction angle (2θ) of 9.4±0.2, 10.1±0.2, 14.8±0.2, 18.0±0.2, 23.0±0.2, 25.4±0.2, 29.2±0.2;

a crystalline form having peaks at diffraction angle (2θ) of 5.3±0.2, 10.6±0.2, 17.2±0.2, 19.8±0.2, 26.5±0.2;

a crystalline form having peaks at diffraction angle (2θ) of 5.1±0.2, 10.2±0.2, 15.2±0.2, 18.6±0.2, 20.5±0.2, 21.9±0.2; and a crystalline form having peaks at diffraction angle (2θ) of 6.6±0.2, 13.9±0.2, 15.9±0.2, 22.0±0.2, 23.8±0.2, 24.6±0.2, 26.8±0.2.

2. The crystalline form of claim 1, wherein the crystalline form has peaks at diffraction angle (2θ) of 9.8±0.2, 11.6±0.2, 13.2±0.2, 14.0±0.2, 16.7±0.2, 17.6±0.2, 20.6±0.2, 22.9±0.2, 26.2±0.2, 29.3±0.2, 30.7±0.2, 31.6±0.2; and wherein the crystalline form has an onset melting point of about 267° C. and a peak temperature of about 268° C.

3. The crystalline form of claim 1, wherein the crystalline form has peaks at diffraction angle (2θ) of 6.0±0.2, 15.9±0.2, 18.1±0.2, 19.7±0.2, 24.6±0.2, 25.4±0.2, 26.7±0.2; and wherein the crystalline form has a melting point of about 240° C.

4. The crystalline form of claim 1, wherein the crystalline form has peaks at diffraction angle (2θ) of 8.7±0.2, 10.9±0.2, 12.9±0.2, 15.4±0.2, 16.4±0.2, 18.9±0.2, 20.3±0.2, 22.1±0.2, 22.7±0.2, 24.9±0.2, and wherein the crystalline form has a first melting point of about 212° C. and second melting point of about 229° C.

5. The crystalline form of claim 1, wherein the crystalline form has peaks at diffraction angle (2θ) of 9.4±0.2, 10.1±0.2, 14.8±0.2, 18.0±0.2, 23.0±0.2, 25.4±0.2, 29.2±0.2, and wherein the crystalline form has a melting point of about 174° C.

6. The crystalline form of claim 1, wherein the crystalline form has peaks at diffraction angle (2θ) of 5.3±0.2, 10.6±0.2, 17.2±0.2, 19.8±0.2, 26.5±0.2, and wherein the crystalline form has a melting point of about 227° C.

7. The crystalline form of claim 1, wherein the crystalline form has peaks at diffraction angle (2θ) of 5.1±0.2, 10.2±0.2, 15.2±0.2, 18.6±0.2, 20.5±0.2, 21.9±0.2, and wherein the crystalline form has a melting point of about 194° C.

8. The crystalline form of claim 1, wherein the crystalline form has peaks at diffraction angle (2θ) of 6.6±0.2, 13.9±0.2, 15.9±0.2, 22.0±0.2, 23.8±0.2, 24.6±0.2, 26.8±0.2, and wherein the crystalline form has a melting point of about 168° C.

9. A composition comprising the crystalline form of claim 1 and at least one pharmaceutically acceptable carrier.

10. The composition of claim 9, wherein the crystalline form has peaks at diffraction angle (2θ) of 6.0±0.2, 15.9±0.2, 18.1±0.2, 19.7±0.2, 24.6±0.2, 25.4±0.2, 26.7±0.2; and wherein the crystalline form has a melting point of about 240° C.

* * * * *